(12) United States Patent
Hibner et al.

(10) Patent No.: US 10,327,796 B2
(45) Date of Patent: Jun. 25, 2019

(54) ULTRASONIC SURGICAL INSTRUMENT WITH DUAL MODES

(71) Applicant: Ethicon Endo-Surgery, LLC, Guaynabo, PR (US)

(72) Inventors: John A. Hibner, Mason, OH (US); Jeffrey D. Messerly, Cincinnati, OH (US); Richard W. Timm, Cincinnati, OH (US); Paul F. Riestenberg, North Bend, OH (US); Craig N. Faller, Batavia, OH (US); Richard C. Smith, Milford, OH (US); David A. Witt, Maineville, OH (US); Benjamin D. Dickerson, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 625 days.

(21) Appl. No.: 14/966,260

(22) Filed: Dec. 11, 2015

(65) Prior Publication Data

US 2016/0175001 A1 Jun. 23, 2016

Related U.S. Application Data

(60) Provisional application No. 62/094,244, filed on Dec. 19, 2014.

(51) Int. Cl.
*A61B 18/14* (2006.01)
*A61B 17/32* (2006.01)
(Continued)

(52) U.S. Cl.
CPC ............... *A61B 17/320092* (2013.01); *A61B 17/320068* (2013.01); *A61N 7/02* (2013.01);
(Continued)

(58) Field of Classification Search
CPC .... A61B 17/320068; A61B 17/320092; A61B 2017/2936; A61B 2017/2939;
(Continued)

(56) References Cited

U.S. PATENT DOCUMENTS 5,322,055 A 6/1994 Davison et al.
5,324,299 A 6/1994 Davison et al.
(Continued)

FOREIGN PATENT DOCUMENTS

WO WO 2002/085218 10/2002
WO WO 2007/143439 12/2007

OTHER PUBLICATIONS

International Search Report and Written Opinion dated May 24, 2016 for Application No. PCT/US15/66042, 6 pages.
(Continued)

*Primary Examiner* — Daniel W Fowler
(74) *Attorney, Agent, or Firm* — Frost Brown Todd LLC

(57) ABSTRACT

A surgical apparatus comprises a body, a shaft assembly, and an end effector. The end effector comprises a clamp arm and an ultrasonic blade in acoustic communication with an ultrasonic transducer via an acoustic waveguide that extends through the shaft assembly. The clamp arm is configured to pivot about a first pivot point toward and away from the ultrasonic blade along a first angular path from a first position to a second position to thereby provide a tissue sealing mode of operation. The clamp arm is further configured to pivot about a second pivot point toward and away from the ultrasonic blade along second angular path from the second position to a third position to thereby provide a tissue cutting and sealing mode of operation. The second pivot point is proximal to the first pivot point.

20 Claims, 38 Drawing Sheets

(51) Int. Cl.
*A61N 7/02* (2006.01)
*A61B 18/00* (2006.01)
*A61B 17/29* (2006.01)

(52) U.S. Cl.
CPC ............... *A61B 2017/2936* (2013.01); *A61B 2017/2939* (2013.01); *A61B 2018/0019* (2013.01); *A61B 2018/0063* (2013.01); *A61B 2018/00607* (2013.01); *A61B 2018/00619* (2013.01)

(58) Field of Classification Search
CPC ........ A61B 18/1442; A61B 2018/0019; A61B 2018/00607; A61B 2018/00619; A61B 2018/0063; A61N 7/02
See application file for complete search history.

(56) References Cited

U.S. PATENT DOCUMENTS

| | | | |
|---|---|---|---|
| 5,827,323 A * | 10/1998 | Klieman | ............... A61B 17/29 606/205 |
| 5,873,873 A | 2/1999 | Smith et al. | |
| 5,893,835 A * | 4/1999 | Witt | ............... A61B 17/32 601/2 |
| 5,980,510 A | 11/1999 | Tsonton et al. | |
| 6,283,981 B1 | 9/2001 | Beaupre | |
| 6,309,400 B2 | 10/2001 | Beaupre | |
| 6,325,811 B1 | 12/2001 | Messerly | |
| 6,423,082 B1 | 7/2002 | Houser et al. | |
| 6,773,444 B2 | 8/2004 | Messerly | |
| 6,783,524 B2 | 8/2004 | Anderson et al. | |
| 8,057,498 B2 | 11/2011 | Robertson | |
| 8,409,200 B2 | 4/2013 | Holcomb et al. | |
| 8,461,744 B2 | 5/2013 | Wiener et al. | |
| 8,591,536 B2 | 11/2013 | Robertson | |
| 8,623,027 B2 | 1/2014 | Price et al. | |
| 8,911,460 B2 | 12/2014 | Neurohr et al. | |
| 8,986,302 B2 | 3/2015 | Aldridge et al. | |
| 9,023,071 B2 | 5/2015 | Miller et al. | |
| 9,095,367 B2 | 8/2015 | Olson et al. | |
| 2006/0079874 A1 | 4/2006 | Faller et al. | |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2010/0185232 A1 * | 7/2010 | Hughett, Sr. | ...... A61B 18/1445 606/207 |
| 2012/0022584 A1 * | 1/2012 | Donnigan | ............... A61B 17/29 606/206 |
| 2012/0112687 A1 | 5/2012 | Houser et al. | |
| 2012/0116265 A1 | 5/2012 | Houser et al. | |
| 2014/0005701 A1 | 1/2014 | Olson et al. | |
| 2014/0194915 A1 | 3/2014 | Johnson et al. | |
| 2015/0080924 A1 | 3/2015 | Stulen et al. | |

OTHER PUBLICATIONS

U.S. Appl. No. 61/410,603, filed Nov. 5, 2010.
U.S. Appl. No. 62/094,244, filed Dec. 19, 2014.
European Examination Report dated May 15, 2018 for Application No. EP 15823871.7, 4 pgs.

* cited by examiner

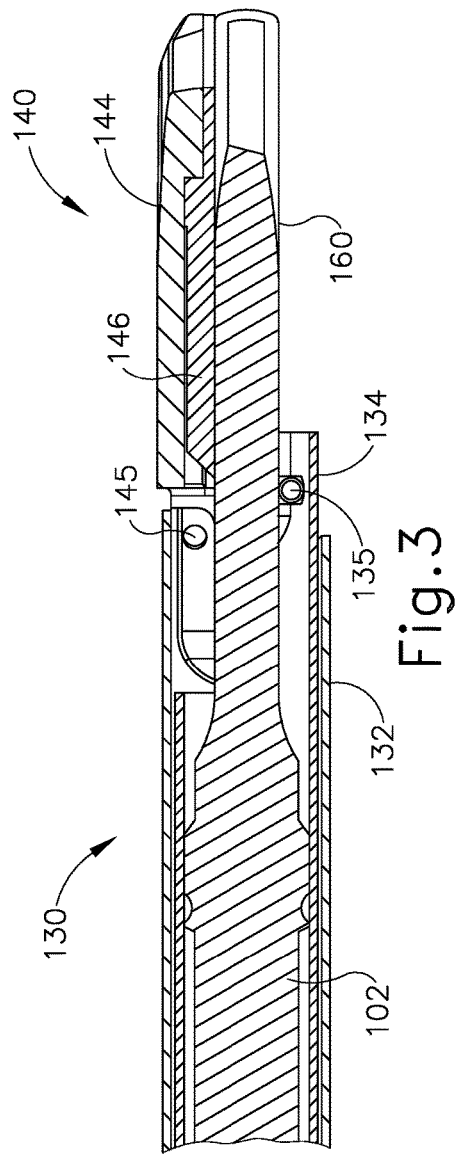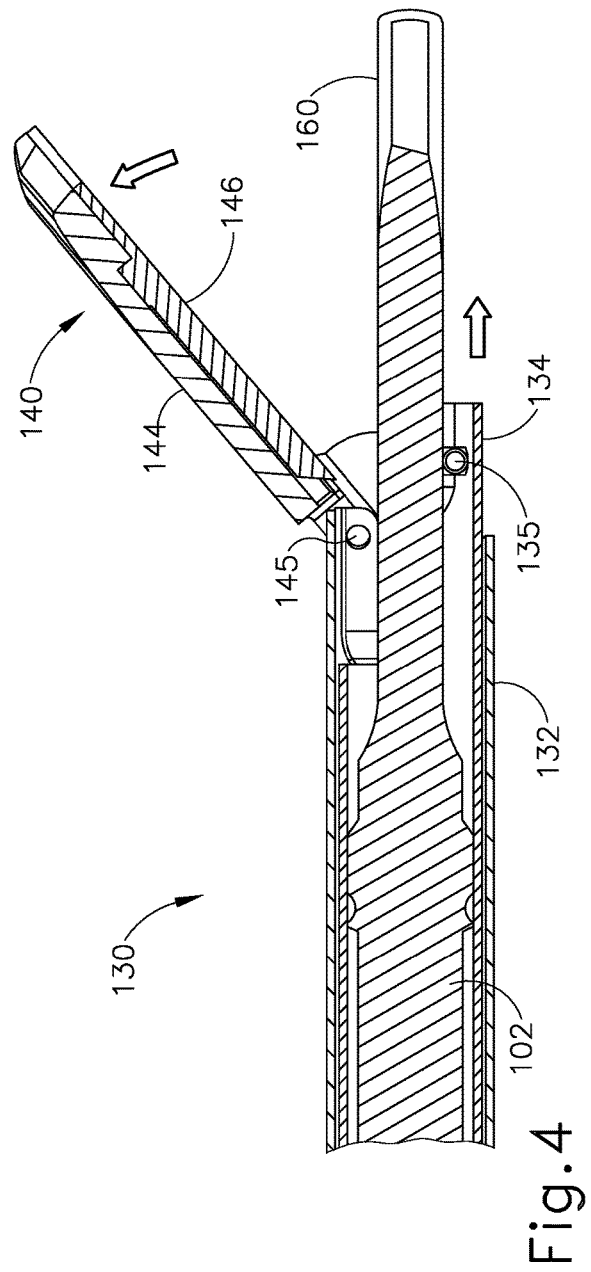
Fig.3
Fig.4

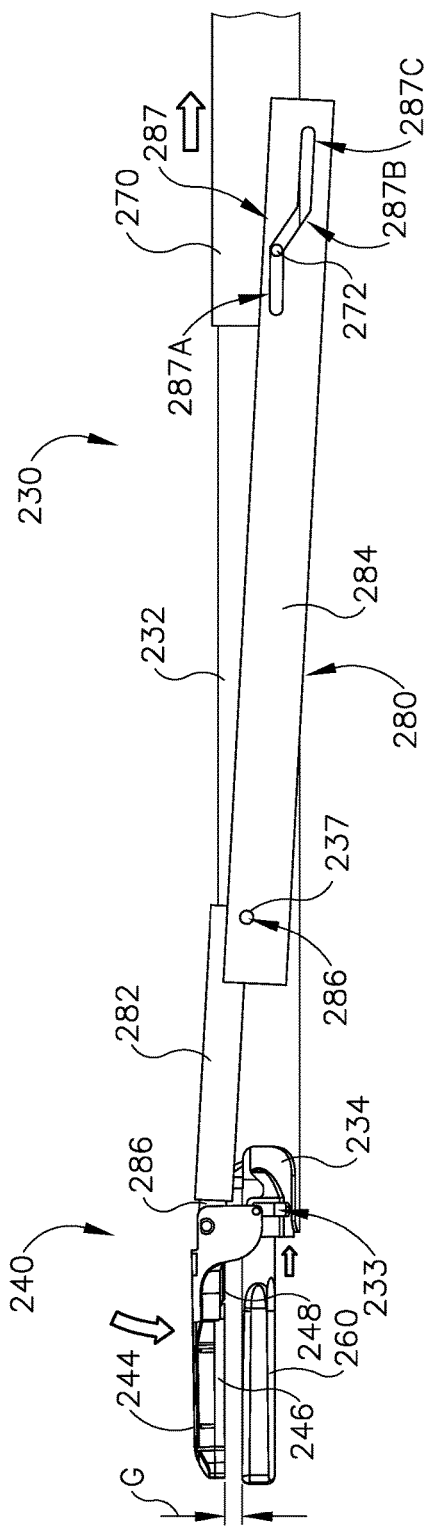
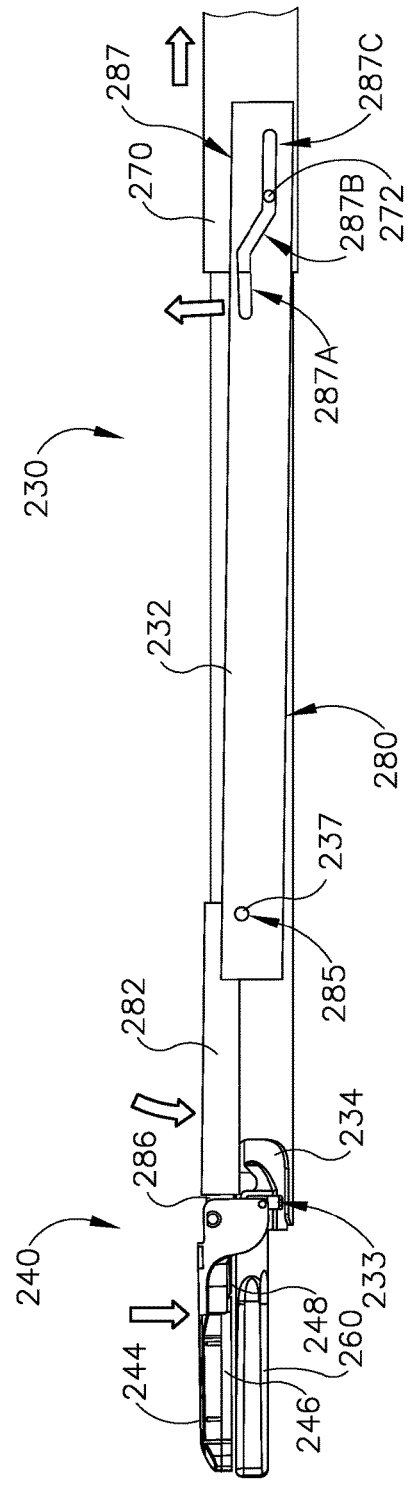
Fig. 17B
Fig. 17C

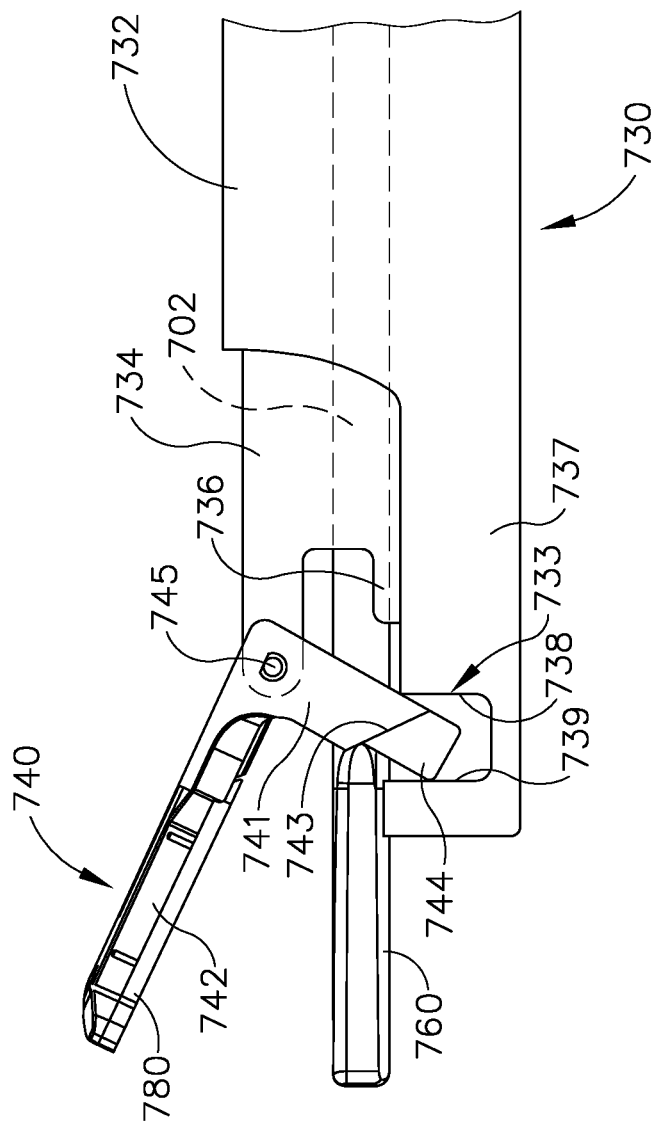

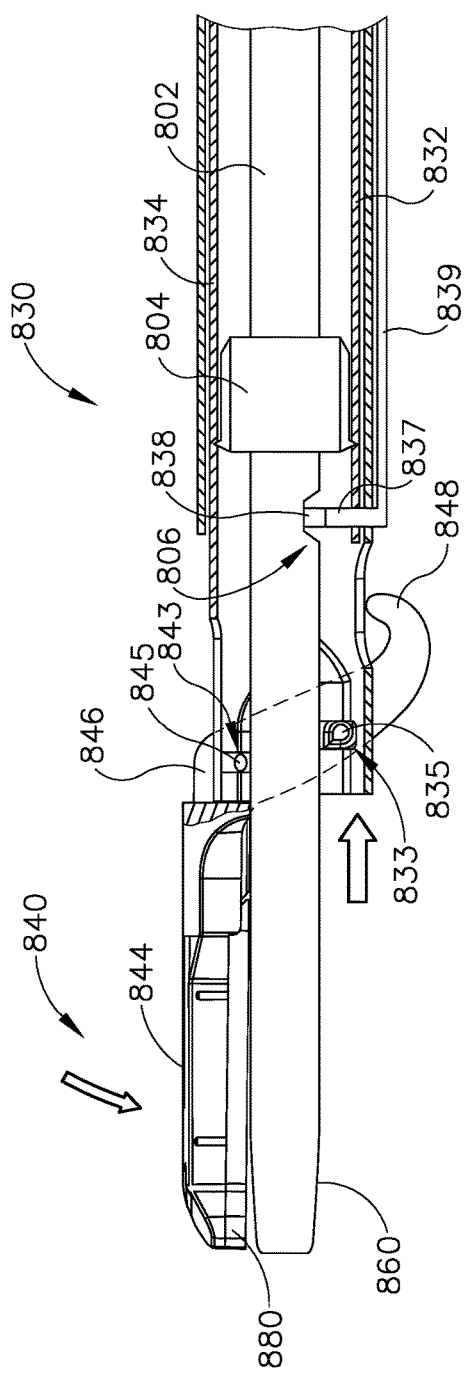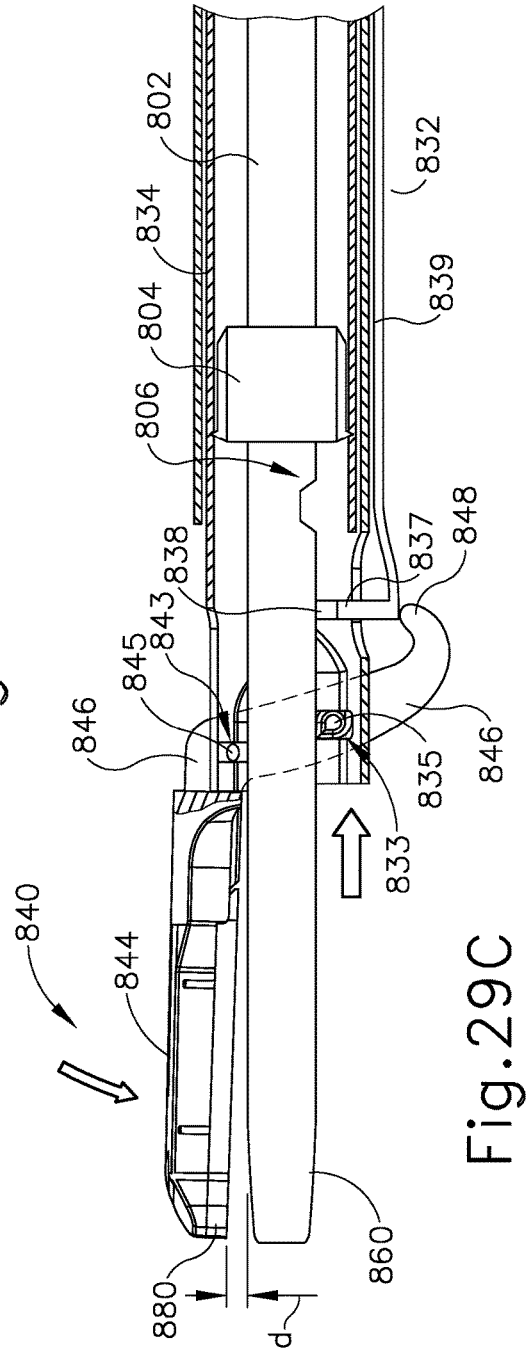
Fig.29B
Fig.29C

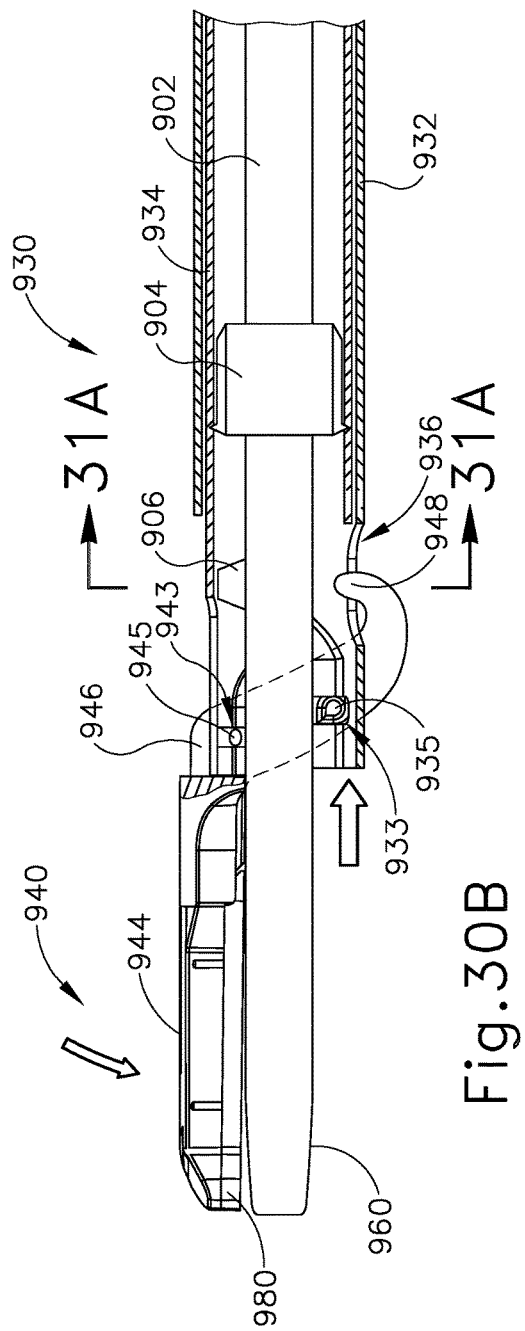
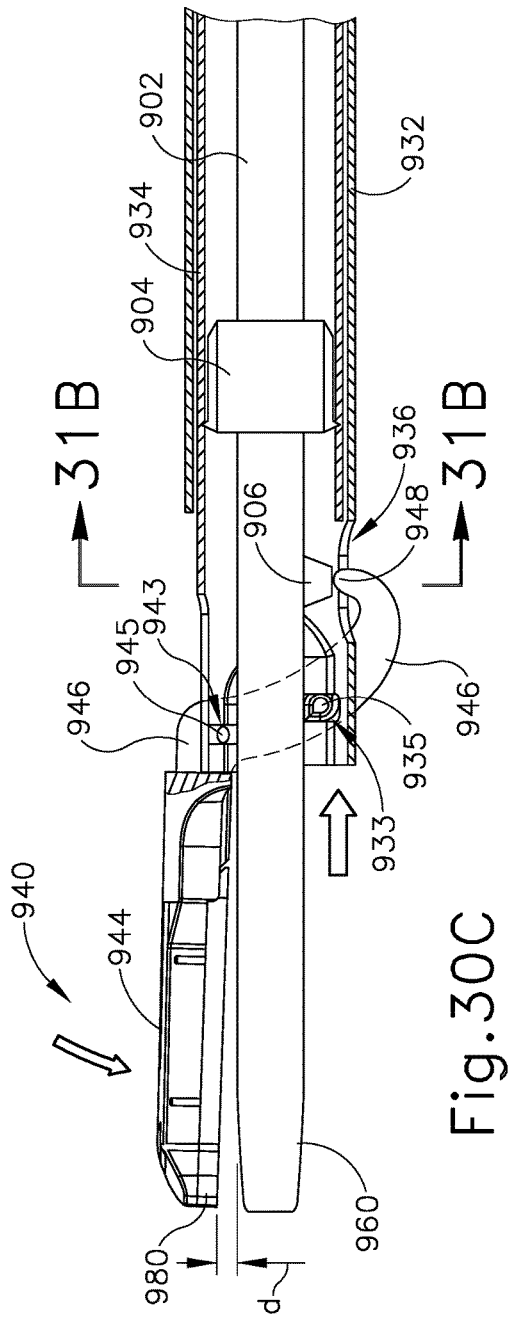
Fig.30B
Fig.30C

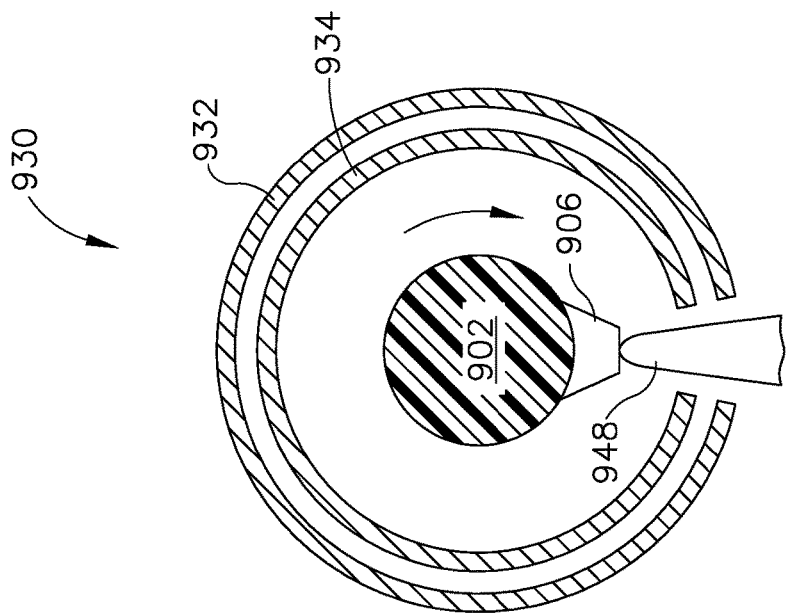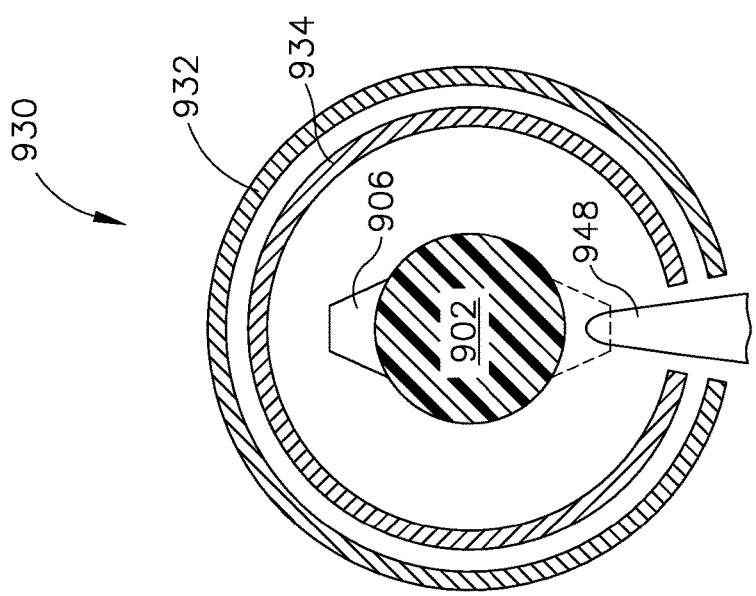

ULTRASONIC SURGICAL INSTRUMENT WITH DUAL MODES

PRIORITY

This Application claims priority to U.S. Patent App. No. 62/094,244, entitled "Ultrasonic Surgical Instrument with Dual Modes," filed Dec. 19, 2014, the disclosure of which is incorporated by reference herein.

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2008/0234710, entitled "Ultrasonic Surgical Instruments," published Sep. 25, 2008, issued as U.S. Pat. No. 8,911,460 on Dec. 16, 2014, the disclosure of which is incorporated by reference herein; and U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, published Jan. 2, 2014, issued as U.S. Pat. No. 9,393,037 on Jul. 19, 2016, entitled "Surgical Instruments with Articulating Shafts," the disclosure of which is incorporated by reference herein; and U.S. Pub. No. 2014/0114334, published Apr. 24, 2014, issued as U.S. Pat. No. 9,095,367 on Aug. 4, 2015, entitled "Flexible Harmonic Waveguides/Blades for Surgical Instruments," the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 3 depicts a cross-sectional side view of an end effector of the instrument of FIG. 2 in a closed position;

FIG. 4 depicts a cross-sectional side view of the end effector of FIG. 3 in an open position;

FIG. 17B depicts a side elevational view of the shaft assembly and end effector of FIG. 8 with the pivot tube of FIG. 13 moved to a second longitudinal position, and with the clamp arm of FIG. 17A moved to a second rotational position by movement of the inner tube of FIG. 15 to a second longitudinal position;

FIG. 17C depicts a side elevational view of the shaft assembly and end effector of FIG. 8 with the clamp arm of FIG. 17A moved to a second vertical position by movement of the pivot arm of FIG. 11 to a second rotational position by movement of the pivot tube of FIG. 13 to a third longitudinal position;

FIG. 27A depicts a side elevational view of an exemplary alternative end effector and an exemplary alternative shaft assembly that may be incorporated into the instrument of FIG. 2, with the end effector in an open position;

FIG. 29B depicts a cross-sectional side view of the end effector and the shaft assembly of FIG. 29A, with the end effector in a first closed position;

FIG. 29C depicts a cross-sectional side view of the end effector and the shaft assembly of FIG. 29A, with the end effector in a second closed position;

FIG. 30B depicts a cross-sectional side view of the end effector and shaft assembly of FIG. 30A, with the end effector in a first closed position;

FIG. 30C depicts a cross-sectional side view of the end effector and shaft assembly of FIG. 30A, with the end effector in a second closed position;

FIG. 31A depicts a cross-sectional front view of the end effector and shaft assembly of FIG. 30A taken along line 31A-31A of FIG. 30B;

FIG. 31B depicts a cross-sectional front view of the end effector and shaft assembly of FIG. 30A taken along line 31B-31B of FIG. 30C;

Figure 1:
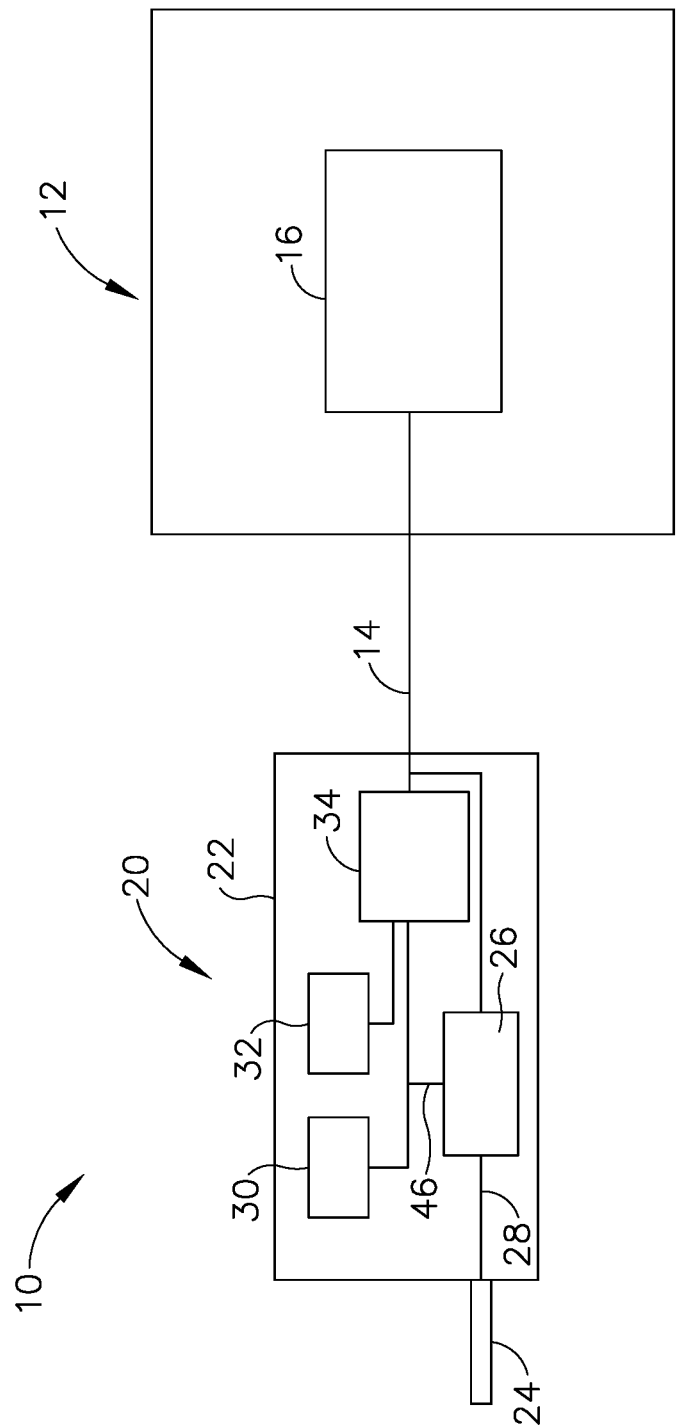
FIG. 1 depicts a block schematic view of an exemplary surgical system.
Figure 2:
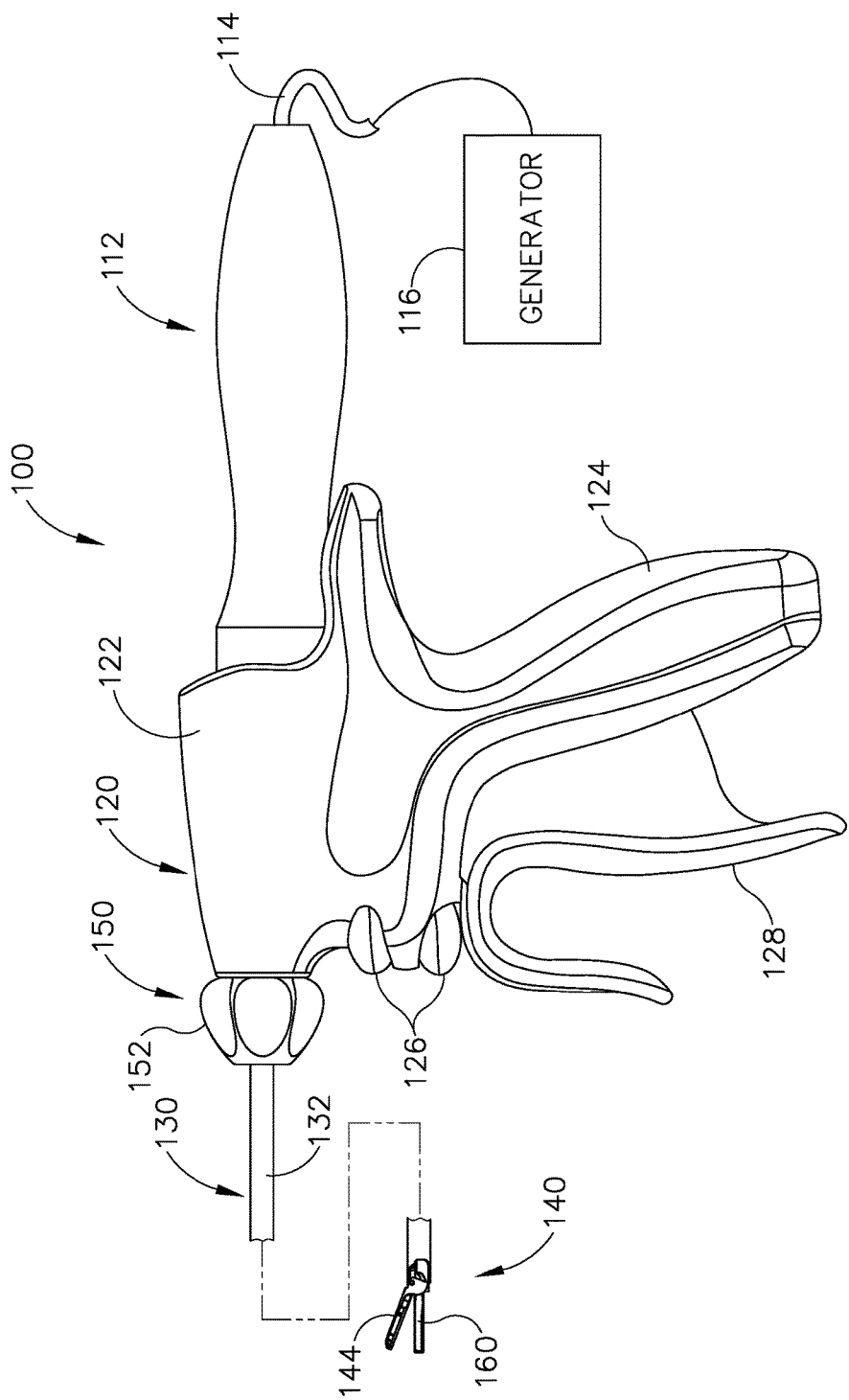
FIG. 2 depicts a side elevational view of an exemplary surgical instrument operable for use with the system of FIG. 1.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator or other operator grasping a surgical instrument having a distal surgical end effector. The term "proximal" refers the position of an element closer to the operator or other operator and the term "distal" refers to the position of an element closer to the surgical end effector of the surgical instrument and further away from the operator or other operator.

I. Overview of Exemplary Ultrasonic Surgical System

FIG. 1 shows components of an exemplary surgical system (10) in diagrammatic block form. As shown, system (10) comprises an ultrasonic generator (12) and an ultrasonic surgical instrument (20). As will be described in greater detail below, instrument (20) is operable to cut tissue and seal or weld tissue (e.g., a blood vessel, etc.) substantially simultaneously, using ultrasonic vibrational energy. Generator (12) and instrument (20) are coupled together via cable (14). Cable (14) may comprise a plurality of wires; and may provide unidirectional electrical communication from generator (12) to instrument (20) and/or bidirectional electrical communication between generator (12) and instrument (20). By way of example only, cable (14) may comprise a "hot" wire for electrical power to surgical instrument (20), a ground wire, and a signal wire for transmitting signals from surgical instrument (20) to ultrasonic generator (12), with a shield surrounding the three wires. In some versions, separate "hot" wires are used for separate activation voltages (e.g., one "hot" wire for a first activation voltage and another "hot" wire for a second activation voltage, or a variable voltage between the wires proportional to the power requested, etc.). Of course, any other suitable number or configuration of wires may be used. It should also be understood that some versions of system (10) may incorporate generator (12) into instrument (20), such that cable (14) may simply be omitted.

By way of example only, generator (12) may comprise the GEN04, GEN11, or GEN 300 sold by Ethicon Endo-Surgery, Inc. of Cincinnati, Ohio. In addition or in the alternative, generator (12) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. Alternatively, any other suitable generator (12) may be used. As will be described in greater detail below, generator (12) is operable to provide power to instrument (20) to perform ultrasonic surgical procedures.

Instrument (20) comprises a handle assembly (22), which is configured to be grasped in one hand (or two hands) of an operator and manipulated by one hand (or two hands) of the operator during a surgical procedure. For instance, in some versions, handle assembly (22) may be grasped like a pencil by the operator. In some other versions, handle assembly (22) may include a scissor grip that may be grasped like scissors by the operator. In some other versions, handle assembly (22) may include a pistol grip that may be grasped like a pistol by the operator. Of course, handle assembly (22) may be configured to be gripped in any other suitable fashion. Furthermore, some versions of instrument (20) may substitute handle assembly (22) with a body that is coupled to a robotic surgical system that is configured to operate instrument (20) (e.g., via remote control, etc.). In the present example, a blade (24) extends distally from the handle assembly (22). Handle assembly (22) includes an ultrasonic transducer (26) and an ultrasonic waveguide (28), which couples ultrasonic transducer (26) with blade (24). Ultrasonic transducer (26) receives electrical power from generator (12) via cable (14). By virtue of its piezoelectric properties, ultrasonic transducer (26) is operable to convert such electrical power into ultrasonic vibrational energy.

Ultrasonic waveguide (28) may be flexible, semi-flexible, rigid, or have any other suitable properties. As noted above, ultrasonic transducer (26) is integrally coupled with blade (24) via ultrasonic waveguide (28). In particular, when ultrasonic transducer (26) is activated to vibrate at ultrasonic frequencies, such vibrations are communicated through ultrasonic waveguide (28) to blade (24), such that blade (24) will also vibrate at ultrasonic frequencies. When blade (24) is in an activated state (i.e., vibrating ultrasonically), blade (24) is operable to effectively cut through tissue and seal tissue. Ultrasonic transducer (26), ultrasonic waveguide (28), and blade (24) together thus form an acoustic assembly providing ultrasonic energy for surgical procedures when powered by generator (12). Handle assembly (22) is configured to substantially isolate the operator from the vibrations of the acoustic assembly formed by transducer (26), ultrasonic waveguide (28), and blade (24).

In some versions, ultrasonic waveguide (28) may amplify the mechanical vibrations transmitted through ultrasonic waveguide (28) to blade (24). Ultrasonic waveguide (28) may further have features to control the gain of the longitudinal vibration along ultrasonic waveguide (28) and/or features to tune ultrasonic waveguide (28) to the resonant frequency of system (10). For instance, ultrasonic waveguide (28) may have any suitable cross-sectional dimensions/configurations, such as a substantially uniform cross-section, be tapered at various sections, be tapered along its entire length, or have any other suitable configuration. Ultrasonic waveguide (28) may, for example, have a length substantially equal to an integral number of one-half system wavelengths ($n\lambda/2$). Ultrasonic waveguide (28) and blade (24) may be fabricated from a solid core shaft constructed out of a material or combination of materials that propagates ultrasonic energy efficiently, such as titanium alloy (i.e., Ti-6Al-4V), aluminum alloys, sapphire, stainless steel, or any other acoustically compatible material or combination of materials.

In the present example, the distal end of blade (24) is located at a position corresponding to an anti-node associated with resonant ultrasonic vibrations communicated through waveguide (28) (i.e., at an acoustic anti-node), in order to tune the acoustic assembly to a preferred resonant frequency $f_o$ when the acoustic assembly is not loaded by tissue. When transducer (26) is energized, the distal end of blade (24) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer (26) of the present example is activated, these mechanical oscillations are transmitted through waveguide (28) to reach blade (24), thereby providing oscillation of blade (24) at the resonant ultrasonic frequency. Thus, the ultrasonic oscillation of blade (24) may simultaneously sever the tissue and denature the proteins in adjacent tissue cells, thereby providing a coagulative effect with relatively little thermal spread. In some versions, an electrical current may also be provided through blade (24) to also cauterize the tissue.

By way of example only, ultrasonic waveguide (28) and blade (24) may comprise components sold under product codes SNGHK and SNGCB by Ethicon Endo-Surgery, Inc. of Cincinnati, Ohio. By way of further example only, ultrasonic waveguide (28) and/or blade (24) may be constructed and operable in accordance with the teachings of U.S. Pat. No. 6,423,082, entitled "Ultrasonic Surgical Blade with Improved Cutting and Coagulation Features," issued Jul. 23, 2002, the disclosure of which is incorporated by reference herein. As another merely illustrative example, ultrasonic waveguide (28) and/or blade (24) may be constructed and operable in accordance with the teachings of U.S. Pat. No. 5,324,299, entitled "Ultrasonic Scalpel Blade and Methods of Application," issued Jun. 28, 1994, the disclosure of which is incorporated by reference herein. Other suitable properties and configurations of ultrasonic waveguide (28) and blade (24) will be apparent to those of ordinary skill in the art in view of the teachings herein.

Handle assembly (22) of the present example also includes a control selector (30) and an activation switch (32), which are each in communication with a circuit board (34). By way of example only, circuit board (34) may comprise a conventional printed circuit board, a flex circuit, a rigid-flex circuit, or may have any other suitable configuration. Control selector (30) and activation switch (32) may be in communication with circuit board (34) via one or more wires, traces formed in a circuit board or flex circuit, and/or in any other suitable fashion. Circuit board (34) is coupled with cable (14), which is in turn coupled with control circuitry (16) within generator (12). Activation switch (32) is operable to selectively activate power to ultrasonic transducer (26). In particular, when switch (32) is activated, such activation provides communication of appropriate power to ultrasonic transducer (26) via cable (14). By way of example only, activation switch (32) may be constructed in accordance with any of the teachings of the various references cited herein. Other various forms that activation switch (32) may take will be apparent to those of ordinary skill in the art in view of the teachings herein.

In the present example, surgical system (10) is operable to provide at least two different levels or types of ultrasonic energy (e.g., different frequencies and/or amplitudes, etc.) at blade (24). To that end, control selector (30) is operable to permit the operator to select a desired level/amplitude of ultrasonic energy. By way of example only, control selector (30) may be constructed in accordance with any of the teachings of the various references cited herein. Other various forms that control selector (30) may take will be apparent to those of ordinary skill in the art in view of the teachings herein. In some versions, when an operator makes a selection through control selector (30), the operator's selection is communicated back to control circuitry (16) of generator (12) via cable (14), and control circuitry (16) adjusts the power communicated from generator (12) accordingly the next time the operator actuates activation switch (32).

It should be understood that the level/amplitude of ultrasonic energy provided at blade (24) may be a function of characteristics of the electrical power communicated from generator (12) to instrument (20) via cable (14). Thus, control circuitry (16) of generator (12) may provide electrical power (via cable (14)) having characteristics associated with the ultrasonic energy level/amplitude or type selected through control selector (30). Generator (12) may thus be operable to communicate different types or degrees of electrical power to ultrasonic transducer (26), in accordance with selections made by the operator via control selector (30). In particular, and by way of example only, generator (12) may increase the voltage and/or current of the applied signal to increase the longitudinal amplitude of the acoustic assembly. As a merely illustrative example, generator (12) may provide selectability between a "level 1" and a "level 5," which may correspond with a blade (24) vibrational resonance amplitude of approximately 50 microns and approximately 90 microns, respectively. Various ways in which control circuitry (16) may be configured will be apparent to those of ordinary skill in the art in view of the teachings herein. It should also be understood that control selector (30) and activation switch (32) may be substituted with two or more activation switches (32). In some such versions, one activation switch (32) is operable to activate blade (24) at one power level/type while another activation switch (32) is operable to activate blade (24) at another power level/type, etc.

In some alternative versions, control circuitry (16) is located within handle assembly (22). For instance, in some such versions, generator (12) only communicates one type of electrical power (e.g., just one voltage and/or current available) to handle assembly (22), and control circuitry (16) within handle assembly (22) is operable to modify the electrical power (e.g., the voltage of the electrical power), in accordance with selections made by the operator via control selector (30), before the electrical power reaches ultrasonic transducer (26). Furthermore, generator (12) may be incorporated into handle assembly (22) along with all other components of surgical system (10). For instance, one or more batteries (not shown) or other portable sources of power may be provided in handle assembly (22). Still other suitable ways in which the components depicted in FIG. 1 may be rearranged or otherwise configured or modified will be apparent to those of ordinary skill in the art in view of the teachings herein.

II. Overview of Exemplary Ultrasonic Surgical Instrument

The following discussion relates to various exemplary components and configurations of instrument (20). It should be understood that the various examples of instrument (20) described below may be readily incorporated into surgical system (10) as described above. It should also be understood that the various components and operabilities of instrument (20) described above may be readily incorporated into the exemplary versions of instrument (20) described below. Various suitable ways in which the above and below teachings may be combined will be apparent to those of ordinary skill in the art in view of the teachings herein. It should also be understood that the below teachings may be readily combined with the various teachings of the references that are cited herein.

FIGS. 2-5 illustrate an exemplary ultrasonic surgical instrument (100). At least part of instrument (100) may be constructed and operable in accordance with at least some of the teachings of U.S. Pat. Nos. 5,322,055; 5,873,873; 5,980,510; 6,325,811; 6,773,444; 6,783,524; 8,461,744; 8,623,027; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2010/0069940, issued as U.S. Pat. No. 9,023,071 on May 5, 2015; U.S. Pub. No. 2012/0112687, issued as U.S. Pat. No. 9,381,058 on Jul. 5, 2016; U.S. Pub. No. 2012/0116265, now abandoned; U.S. Pub. No. 2014/0005701, issued as U.S. Pat. No. 9,393,037 on Jul. 19, 2016; U.S. Pub. No. 2014/0114334, issued as U.S. Pat. No. 9,095,367 on Aug. 4, 2015; U.S. Pat. App. No. 61/410,603; and/or U.S. patent application Ser. No. 14/028,717, issued as U.S. Pat. No. 10,172,636 on Jan. 8, 2019. The disclosures of each of the foregoing patents, publications, and applications are incorporated by reference herein. As described therein and as will be described in greater detail below, instrument (100) is operable to cut tissue and seal or weld tissue (e.g., a blood vessel, etc.) substantially simultaneously. It should also be understood that instrument (100) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (100) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (100), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Instrument (100) of the present example comprises a handle assembly (120), a shaft assembly (130), and an end effector (140). Handle assembly (120) comprises a body (122) including a pistol grip (124) and a pair of buttons (126). Handle assembly (120) also includes a trigger (128) that is pivotable toward and away from pistol grip (124). It should be understood, however, that various other suitable configurations may be used, including but not limited to a pencil-grip configuration or a scissor-grip configuration. End effector (140) includes an ultrasonic blade (160) and a pivoting clamp arm (144). Clamp arm (144) is coupled with trigger (128) such that clamp arm (144) is pivotable toward ultrasonic blade (160) in response to pivoting of trigger (128) toward pistol grip (124); and such that clamp arm (144) is pivotable away from ultrasonic blade (160) in response to pivoting of trigger (128) away from pistol grip (124). Various suitable ways in which clamp arm (144) may be coupled with trigger (128) will be apparent to those of ordinary skill in the art in view of the teachings herein. In some versions, one or more resilient members are used to bias clamp arm (144) and/or trigger (128) to the open position shown in FIG. 4.

An ultrasonic transducer assembly (112) extends proximally from body (122) of handle assembly (120). Transducer assembly (112) is coupled with a generator (116) via a cable (114). Transducer assembly (112) receives electrical power from generator (116) and converts that power into ultrasonic vibrations through piezoelectric principles. Generator (116) may include a power source and control module that is configured to provide a power profile to transducer assembly (112) that is particularly suited for the generation of ultrasonic vibrations through transducer assembly (112). By way of example only, generator (116) may comprise a GEN 300 sold by Ethicon Endo-Surgery, Inc. of Cincinnati, Ohio. In addition or in the alternative, generator (116) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. It should also be understood that at least some of the functionality of generator (116) may be integrated into handle assembly (120), and that handle assembly (120) may even include a battery or other on-board power source such that cable (114) is omitted. Still other suitable forms that generator (116) may take, as well as various features and operabilities that generator (116) may provide, will be apparent to those of ordinary skill in the art in view of the teachings herein.

Blade (160) of the present example is operable to vibrate at ultrasonic frequencies in order to effectively cut through and seal tissue, particularly when the tissue is being clamped between clamp arm (144) and blade (160). Blade (160) is positioned at the distal end of an acoustic drivetrain. This acoustic drivetrain includes transducer assembly (112) and an acoustic waveguide (102). Transducer assembly (112) includes a set of piezoelectric discs (not shown) located proximal to a horn (not shown) of rigid acoustic waveguide (102). The piezoelectric discs are operable to convert electrical power into ultrasonic vibrations, which are then transmitted along acoustic waveguide (102), which extends through shaft assembly (130), to blade (160) in accordance with known configurations and techniques. By way of example only, this portion of the acoustic drivetrain may be configured in accordance with various teachings of various references that are cited herein.

Waveguide (102) is secured within shaft assembly (130) via a pin (133), which passes through waveguide (102) and shaft assembly (130). Pin (133) is located at a position along the length of waveguide (102) corresponding to a node associated with resonant ultrasonic vibrations communicated through waveguide (102). When ultrasonic blade (160) is in an activated state (i.e., vibrating ultrasonically), ultrasonic blade (160) is operable to effectively cut through and seal tissue, particularly when the tissue is being clamped between clamp arm (144) and ultrasonic blade (160). It should be understood that waveguide (102) may be configured to amplify mechanical vibrations transmitted through waveguide (102). Furthermore, waveguide (102) may include features operable to control the gain of the longitudinal vibrations along waveguide (102) and/or features to tune waveguide (102) to the resonant frequency of the system.

In the present example, the distal end of blade (160) is located at a position corresponding to an anti-node associated with resonant ultrasonic vibrations communicated through waveguide (102), in order to tune the acoustic assembly to a preferred resonant frequency $f_o$ when the acoustic assembly is not loaded by tissue. When transducer assembly (112) is energized, the distal end of blade (160) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (112) of the present example is activated, these mechanical oscillations are transmitted through waveguide (102) to reach blade (160), thereby providing oscillation of blade (160) at the resonant ultrasonic frequency. Thus, when tissue is secured between blade (160) and clamp arm (144), the ultrasonic oscillation of blade (160) may simultaneously sever the tissue and denature the proteins in adjacent tissue cells, thereby providing a coagulative effect with relatively little thermal spread. In some versions, an electrical current may also be provided through blade (160) and clamp arm (144) to also cauterize the tissue. While some configurations for an acoustic transmission assembly and transducer assembly (112) have been described, still other suitable configurations for an acoustic transmission assembly and transducer assembly (112) will be apparent to one or ordinary skill in the art in view of the teachings herein. Similarly, other suitable configurations for end effector (140) will be apparent to those of ordinary skill in the art in view of the teachings herein.

An operator may activate buttons (126) to selectively activate transducer assembly (112) to activate blade (160). In the present example, two buttons (126) are provided—one for activating blade (160) at a low power and another for activating blade (160) at a high power. However, it should be understood that any other suitable number of buttons and/or otherwise selectable power levels may be provided. For instance, a foot pedal may be provided to selectively activate transducer assembly (112). Buttons (126) of the present example are positioned such that an operator may readily fully operate instrument (100) with a single hand. For instance, the operator may position their thumb about pistol grip (124), position their middle, ring, and/or little finger about trigger (128), and manipulate buttons (126) using their index finger. Of course, any other suitable techniques may be used to grip and operate instrument (100); and buttons (126) may be located at any other suitable positions.

Shaft assembly (130) of the present example comprises an outer sheath (132), an inner tube (134) slidably disposed within outer sheath (132), and a waveguide (102) disposed within inner tube (134). As will be discussed in more detail below inner tube (134) is operable to translate longitudinally within outer sheath (132) relative to outer sheath (132) to selectively pivot clamp arm (144) toward and away from blade (160). Shaft assembly (130) of the present example further includes a rotation assembly (150). Rotation assembly (150) is operable to rotate the entire shaft assembly (130) and end effector (140) relative to handle assembly (120) about a longitudinal axis of shaft assembly (130). In some versions, rotation assembly (150) is operable to selectively lock the angular position of shaft assembly (130) and end effector (140) relative to handle assembly (120) about the longitudinal axis of shaft assembly (130). For instance, a rotation knob (152) of rotation assembly (150) may be translatable between a first longitudinal position, in which shaft assembly (130) and end effector (140) are rotatable relative to handle assembly (120) about the longitudinal axis of shaft assembly (130); and a second longitudinal position, in which shaft assembly (130) and end effector (140) are not rotatable relative to handle assembly (120) about the longitudinal axis of shaft assembly (130). Of course, shaft assembly (130) may have a variety of other components, features, and operabilities, in addition to or in lieu of any of those noted above. Other suitable configurations for shaft assembly (130) will be apparent to those of ordinary skill in the art in view of the teachings herein.

As shown in FIGS. 3 and 4, end effector (140) includes ultrasonic blade (160) and clamp arm (144). Clamp arm (144) includes a clamp pad (146) secured to an underside of clamp arm (144), facing blade (160). Clamp arm (144) is pivotably coupled with a distal end of outer sheath (132) of shaft assembly (130) above ultrasonic blade (160) via a pin (145). As best seen in FIG. 4, a distal end of inner tube (134) is rotatably coupled with a proximal end of clamp arm (144) below ultrasonic blade (160) via a pin (135) such that longitudinal translation of inner tube (134) causes rotation of clamp arm (144) about pin (145) toward and away from ultrasonic blade (160) to thereby clamp tissue between clamp arm (144) and ultrasonic blade (160) to cut and/or seal the tissue. In particular, proximal longitudinal translation of inner tube (134) relative to outer sheath (132) and handle assembly (120) causes clamp arm (144) to move toward ultrasonic blade (160); and distal longitudinal translation of inner tube (134) relative to outer sheath (132) and handle assembly (120) causes clamp arm (144) to move away from ultrasonic blade (160).

Figure 5:
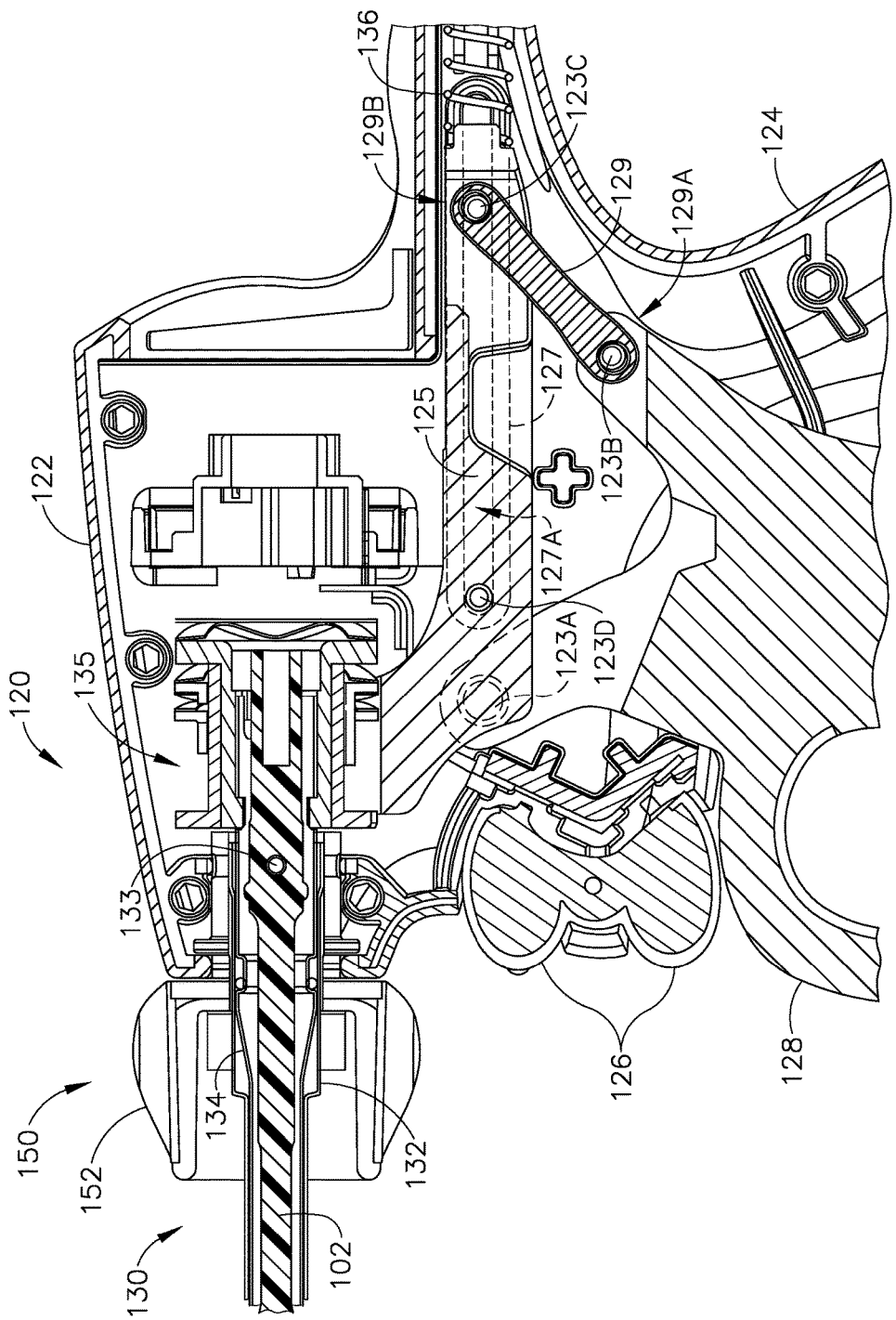
FIG. 5 depicts a cross-sectional side view of a handle assembly of the instrument of FIG. 2.
Figure 6:
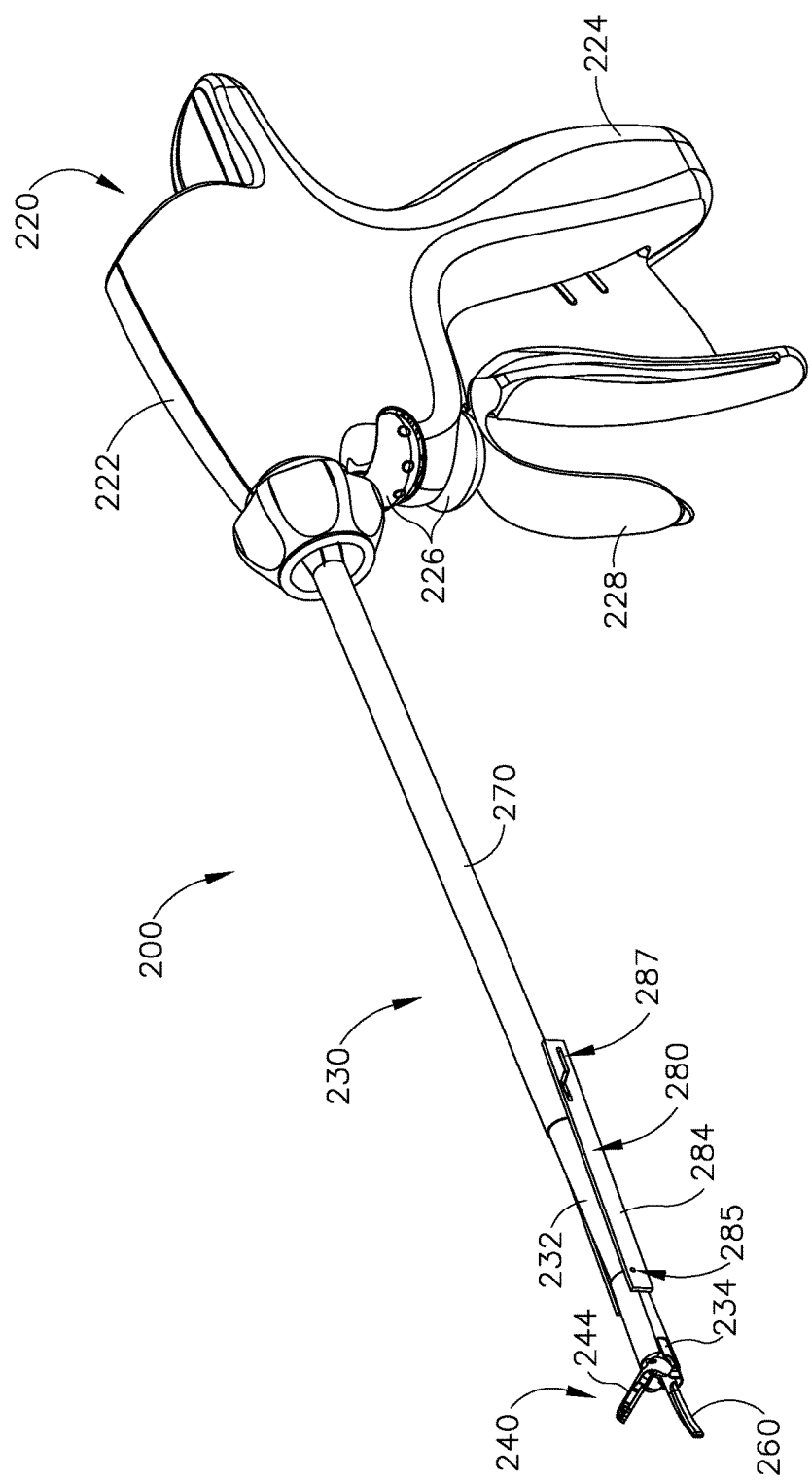
FIG. 6 depicts a perspective view of an exemplary alternative ultrasonic surgical instrument operable for use with the system of FIG. 1.

As shown in FIG. 5, and as discussed above, trigger (128) is pivotably coupled to handle assembly (120) via a pin (123A) such that trigger (128) is operable to rotate about pin (123A). As will be described in more detail below, trigger (128) is coupled with a yoke (125) via a linkage (129) such that rotation of trigger (128) about pin (123A) causes longitudinal translation of yoke (125). A first end (129A) of linkage (129) is rotatably coupled with a proximal portion of trigger (128) via a pin (123B). A second end (129B) of linkage (129) is rotatably coupled with a proximal portion of yoke (125) via a pin (123C). A pair of elongate oval-shaped projections (127) extend inwardly from interior surfaces of body (122). An interior surface of each oval-shaped projection (127) defines an elongate oval-shaped slot (127A). Pin (123C) passes completely through the proximal portion of yoke (125) and second end (129B) of linkage (129) such that ends of pin (123C) extend from opposite sides of yoke (125). These ends of pin (123C) are slidably and rotatably disposed within oval-shaped slots (127A). A pin (123D) passes completely through a distal portion of yoke (125) such that ends of pin (123D) extend from opposite sides of yoke (125). These ends of pin (123D) are slidably and rotatably disposed within oval-shaped slots (127A). It should therefore be understood that yoke (125) is longitudinally translatable within oval-shaped slots (127A) via pins (123C, 123D) between a proximal longitudinal position and a distal longitudinal position. Furthermore, because the proximal portion of trigger (128) is coupled with yoke (125) via linkage (129), pivoting of trigger (128) toward and away from pistol grip (124) will cause longitudinal translation of yoke (125) within oval-shaped slots (127A). In particular, pivoting of trigger (128) toward pistol grip (124) will cause proximal longitudinal translation of yoke (125) within oval-shaped slots (127A); and that pivoting of trigger (128) away from pistol grip (124) will cause distal longitudinal translation of yoke (125) within oval-shaped slots (127A).

A distal portion of yoke (125) is coupled with inner tube (134) of shaft assembly (130) via a coupling assembly (135). As discussed above, inner tube (134) is longitudinally translatable within outer sheath (132), such that inner tube (134) is configured to longitudinally translate concurrently with yoke (125). Furthermore, because pivoting of trigger (128) toward pistol grip (124) causes proximal longitudinal translation of yoke (125), it should be understood that pivoting of trigger (128) toward pistol grip (124) will cause proximal longitudinal translation of inner tube (134) relative to outer sheath (132) and handle assembly (120); and because pivoting of trigger (128) away from pistol grip (124) causes distal longitudinal translation of yoke (125), it should be understood that and that pivoting of trigger (128) away from pistol grip (124) will cause distal longitudinal translation of inner tube (134) relative to outer sheath (132) and handle assembly (120). Finally, because longitudinal translation of inner tube (134) causes rotation of clamp arm (144) toward and away from blade (160) as discussed above, it should be understood that pivoting of trigger (128) toward pistol grip (124) will cause clamp arm (144) to move toward ultrasonic blade (160); and that pivoting of trigger (128) away from pistol grip (124) will cause clamp arm (144) to move away from ultrasonic blade (160).

In some versions, one or more resilient members are used to bias clamp arm (144) and/or trigger (128) to the open position shown in FIG. 4. For instance, as shown in FIG. 5, a spring (136) is positioned within a proximal end of body (122) of handle assembly (120). Spring (136) bears against body (122) and a proximal end of yoke (125) to thereby bias yoke (125) toward the distal position. Biasing of yoke (125) toward the distal position causes inner tube (134) to be biased distally and further causes trigger (128) to be biased away from pistol grip (124).

The foregoing components and operabilities of instrument (100) are merely illustrative. Instrument (100) may be configured in numerous other ways as will be apparent to those of ordinary skill in the art in view of the teachings herein. By way of example only, at least part of instrument (100) may be constructed and/or operable in accordance with at least some of the teachings of any of the following, the disclosures of which are all incorporated by reference herein: U.S. Pat. No. 5,322,055; 5,873,873; 5,980,510; 6,325,811; 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2010/0069940, issued as U.S. Pat. No. 9,023,071 on May 5, 2015; U.S. Pub. No. 2011/0015660, issued as U.S. Pat. No. 8,461,744 on Jun. 11, 2013; U.S. Pub. No. 2012/0112687, issued as U.S. Pat. No. 9,381,058 on Jul. 5, 2016; U.S. Pub. No. 2012/0116265, now abandoned; U.S. Pub. No. 2014/0005701, issued as U.S. Pat. No. 9,393,037 on Jul. 19, 2016; and/or U.S. Pub. No. 2014/0114334, issued as U.S. Pat. No. 9,095,367 on Aug. 4, 2015. Additional merely illustrative variations for instrument (100) will be described in greater detail below. It should be understood that the below described variations may be readily applied to instrument (100) described above and any of the instruments referred to in any of the references that are cited herein, among others.

III. Exemplary Ultrasonic Surgical Instrument with Dual Modes

In some instances, it may be desirable to provide instruments (20, 100) with features configured to allow an operator to selectively seal or weld tissue (e.g., a blood vessel, etc.) without cutting the tissue ("seal-only" mode) or cut tissue and seal or weld tissue substantially simultaneously ("cut-and-seal" mode). One merely exemplary way in which to provide such selective operation to instruments (20, 100) is to provide instrument (100) with features operable to selectively increase and/or decrease a pressure applied to tissue by blades (24, 160). For instance, instrument (100) may be provided with features operable to selectively increase and/or decrease a clamping pressure applied to tissue between clamp arm (144) and blade (160). The examples described below provide various examples of features and techniques configured to allow an operator to selectively seal or weld tissue without cutting the tissue or cut tissue and seal or weld tissue substantially simultaneously. In other words, the examples described below provide various examples of features and techniques that enable an operator to selectively switch a variation of instrument (20, 100) between two modes of operation—a seal-only mode and a cut-and-seal mode. While various examples of features operable to provide such selective operation in instruments (20, 100) will be described in greater detail below, other examples will be apparent to those of ordinary skill in the art according to the teachings herein. Similarly, various suitable ways in which the below teachings may be combined with the teachings of the various references cited herein will be apparent to those of ordinary skill in the art.

The examples provided below are directed mainly to mechanical features that provide two modes of operation—a seal-only mode and a cut-and-seal mode. In addition to the mechanical aspects of these two modes as described below, it should be understood that the below described variations of instrument (20, 100) may also provide different ultrasonic activation based on whether the instrument is in a seal-only mode or a cut-and-seal mode. For instance, if the instrument is in a seal-only mode, generator (116) may activate transducer assembly (112) to cause blade (24, 160) to vibrate with ultrasonic characteristics that are tuned or optimized to just sealing tissue. If the instrument is in a cut-and-seal mode, generator (116) may activate transducer assembly (112) to cause blade (24, 160) to vibrate with ultrasonic characteristics that are tuned or optimized to cut tissue. In versions where movement of one or more mechanical features provide a transition between the seal-only mode and the cut-and-seal mode, one or more sensors may detect such movement to thereby detect the transitions between the seal-only mode and the cut-and-seal mode. Generator (116) may be in communication with such sensors, such that generator (116) may alter the ultrasonic characteristics of blade (24, 160) based on information from such sensors. Various suitable ways in which the operation of generator (116) and/or blade (24, 160) may vary in accordance with transitions between a seal-only mode and a cut-and-seal mode will be apparent to those of ordinary skill in the art in view of the teachings herein. Similarly, various suitable ways in which feedback may be provided to generator (116) to indicate transitions between a seal-only mode and a cut-and-seal mode will be apparent to those of ordinary skill in the art in view of the teachings herein.

A. Exemplary Ultrasonic Surgical Instrument with Elongate Pivot Arm

FIGS. 6-19C illustrate an exemplary ultrasonic surgical instrument (200) that is configured to operate substantially similar to instrument (100) discussed above except for the differences discussed below. Instrument (200) of the present example comprises a handle assembly (220), a shaft assembly (230), and an end effector (240). Handle assembly (220) comprises a body (222) including a pistol grip (224) and a pair of buttons (226). Handle assembly (220) also includes a trigger (228) that is pivotable toward and away from pistol grip (224). End effector (240) includes an ultrasonic blade (260) and a pivoting clamp arm (244). Blade (260) is positioned at the distal end of an acoustic waveguide (202), which mechanically and acoustically couples an ultrasonic transducer (not shown) with blade (260). Waveguide (202) is secured within shaft assembly (230) via a pin (231), which passes through waveguide (202) and shaft assembly (230). Pin (231) is located at a position along the length of waveguide (202) corresponding to a node associated with resonant ultrasonic vibrations communicated through waveguide (202). Clamp arm (244) is coupled with trigger (228) such that clamp arm (244) is pivotable toward ultrasonic blade (260) in response to pivoting of trigger (228) toward pistol grip (224); and such that clamp arm (244) is pivotable away from ultrasonic blade (260) in response to pivoting of trigger (228) away from pistol grip (224). In some versions, one or more resilient members are used to bias clamp arm (244) and/or trigger (228) to an open position.

Figure 18A:
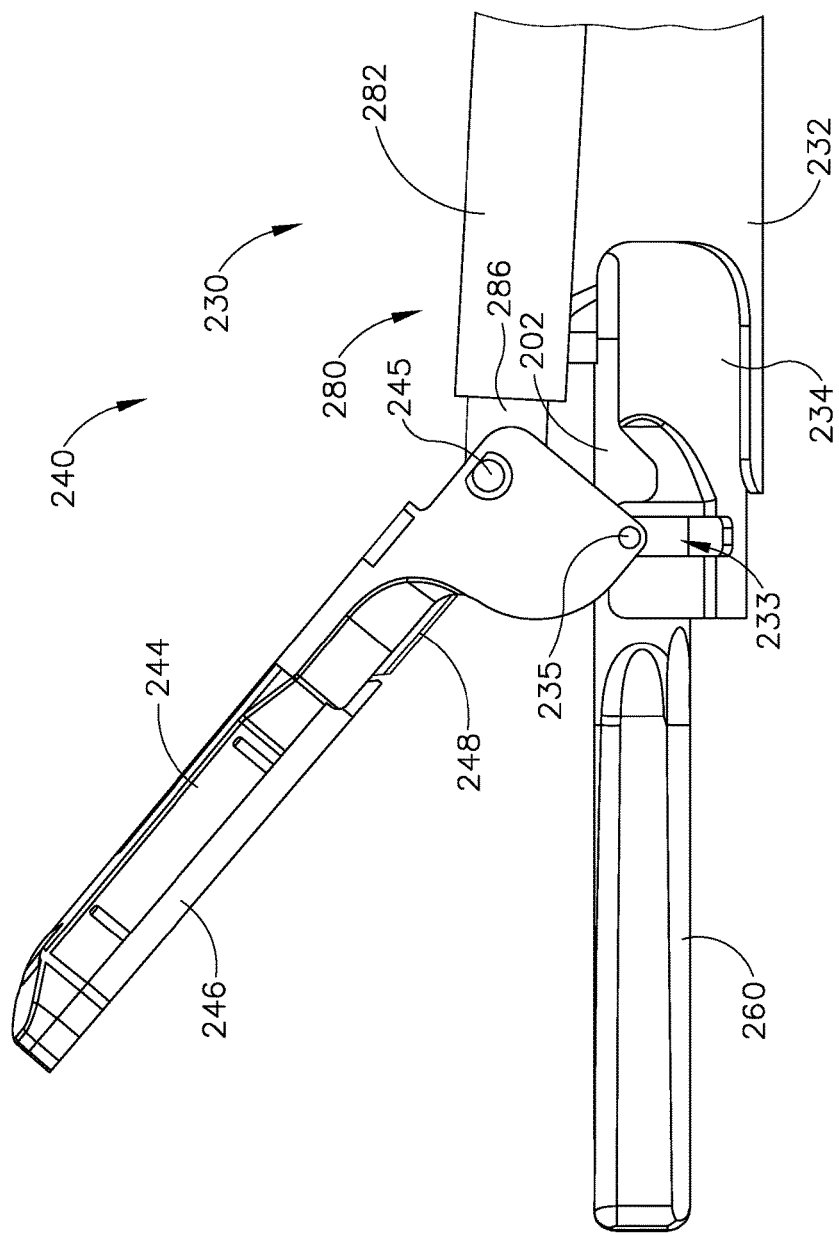
FIG. 18A depicts a side elevational view of the end effector of FIG. 8 with the pivot arm of FIG. 11 in the first rotational position, with the inner tube of FIG. 15 in the first longitudinal position, and with the clamp arm of FIG. 17A in the first vertical position and the first rotational position.
Figure 18B:
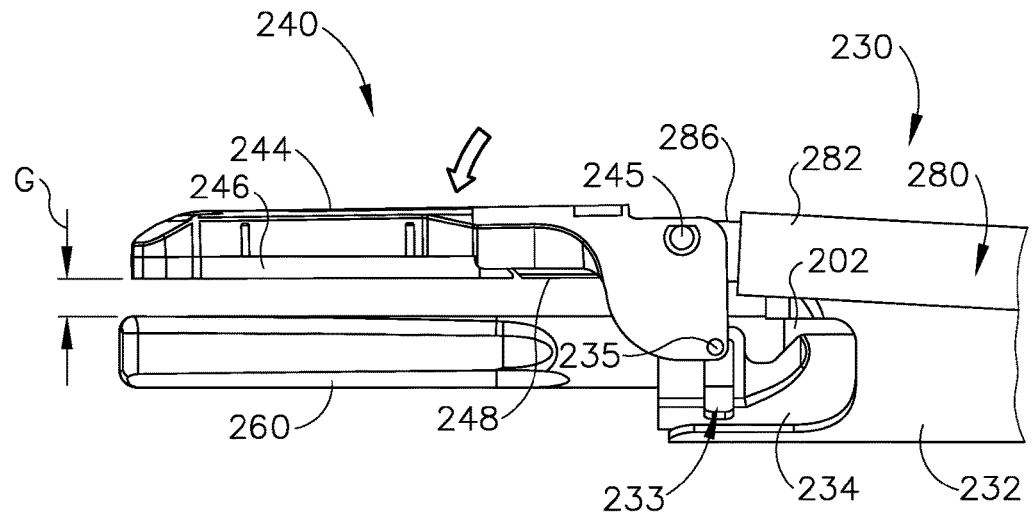
FIG. 18B depicts a side elevational view of the end effector of FIG. 8 with the clamp arm of FIG. 17A moved to the second rotational position by movement of the inner tube of FIG. 15 to the second longitudinal position.
Figure 18C:
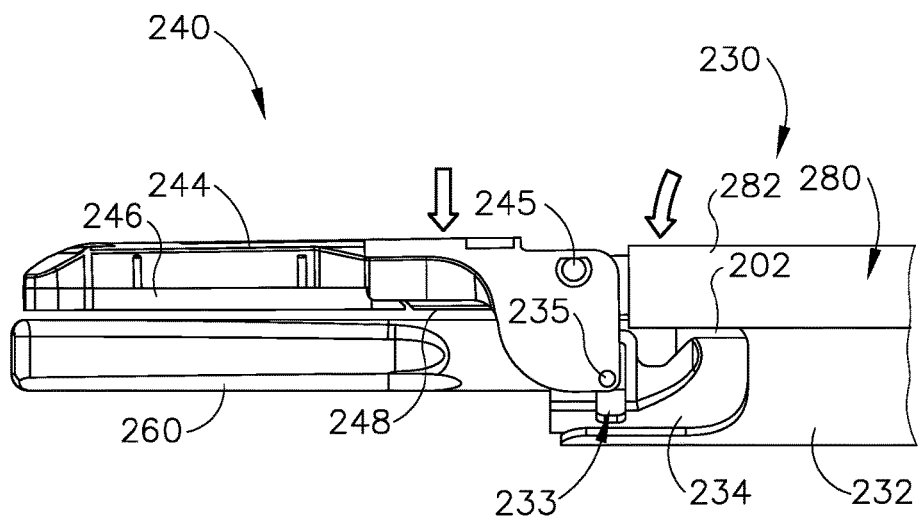
FIG. 18C depicts a side elevational view of the end effector of FIG. 8 with the clamp arm of FIG. 17A moved to the second vertical position by movement of the pivot arm of FIG. 11 to the second rotational position.

Shaft assembly (230) of the present example comprises an outer sheath (232), an inner tube (234), and a pivot tube (270). Outer sheath (232) is secured to waveguide (202) via pin (231). Inner tube (234) is slidably disposed within outer sheath (232). As with shaft assembly (130) discussed above, inner tube (234) is operable to translate longitudinally within outer sheath (232) relative to outer sheath (232) to selectively pivot clamp arm (244) toward and away from blade (260). Pivot tube (270) is slidably disposed about outer sheath (232) such that pivot tube (270) is operable to translate longitudinally about outer sheath (232) relative to outer sheath (232) and handle assembly (220). Shaft assembly (230) further comprises a pivot arm assembly (280). Pivot arm assembly (280) is pivotably coupled with outer sheath (232). Pivot arm assembly (280) is further pivotably and slidably coupled with pivot tube (270). As will be discussed in more detail below, pivot tube (270) is operable to translate longitudinally about outer sheath (232) relative to outer sheath (232) and handle assembly (220) to selectively rotate pivot arm assembly (280) about outer sheath (232) to thereby translate clamp arm (244) vertically toward and away from blade (260). As will also be discussed in more detail below, a transition from (i) pivotal movement of clamp arm (244) about pin (245) toward blade (260) to (ii) pivotal movement of clamp arm (244) about pins (237) toward blade (260) will selectively change instrument (200) between a (i) "seal-only" operation and a (ii) "cut-and-seal" operation. FIGS. 18A-18B show a sequence where clamp arm (244) pivots about pin (245) toward blade (260). FIGS. 18B-18C show a sequence where clamp arm (244) pivots about pins (237) toward blade (260). When viewed so closely to end effector (240) as shown in FIGS. 18B-18C, this pivotal movement of clamp arm (244) about pins (237)

may appear to be simply vertical translational movement of clamp arm (244) toward pins (237). This is due to pins (237) providing fulcrum/pivot points that are substantially spaced away from clamp arm (244). It should be understood that this pivotal movement about pins (237), or "apparent vertical translation," of clamp arm (244) toward and away from blade (260) is along a path that is substantially perpendicular to a longitudinal axis defined by shaft assembly (230).

Figure 9:
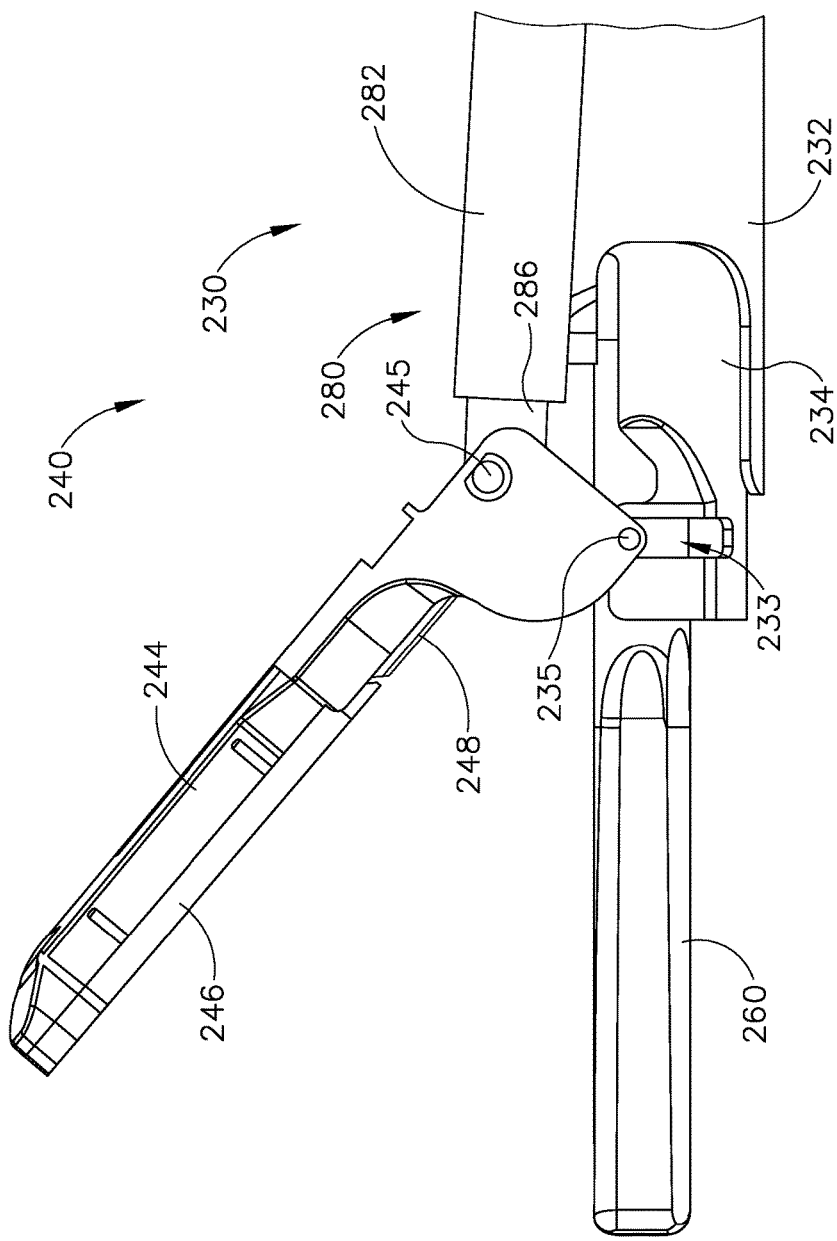
FIG. 9 depicts a side elevational view of the end effector of FIG. 8.
Figure 10:
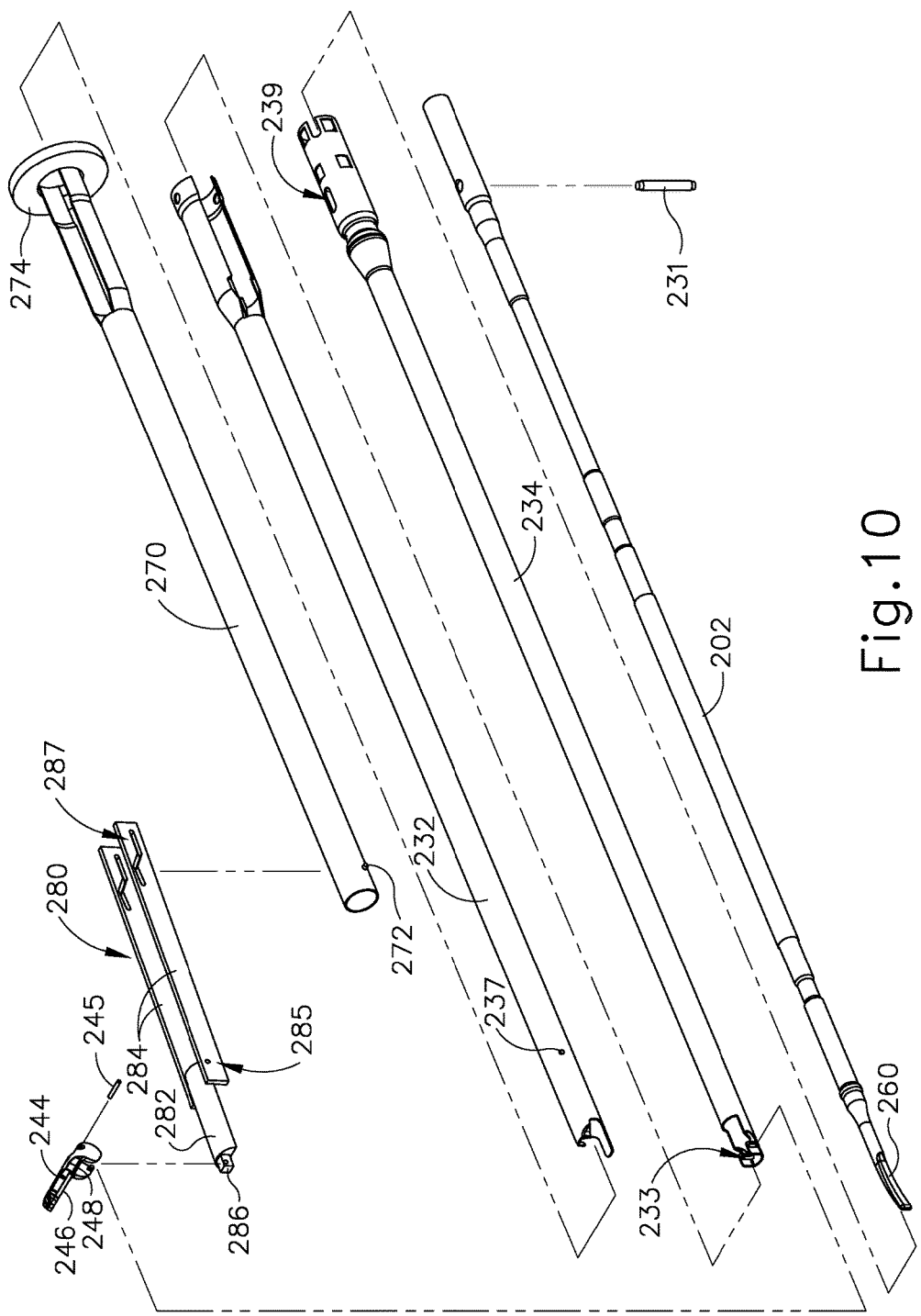
FIG. 10 depicts an exploded perspective view of the shaft assembly and end effector of FIG. 8.

As best seen in FIG. 9, end effector (240) of the present example comprises clamp arm (244) and ultrasonic blade (260). Clamp arm (244) includes a primary clamp pad (246) and a secondary clamp pad (248) that are secured to an underside of clamp arm (244), facing blade (260). Clamp arm (244) is operable to selectively pivot toward and away from blade (260) to selectively clamp tissue between clamp pads (246, 248) and blade (260). As will be discussed in more detail below, clamp arm (244) is pivotably coupled with a distal end of a semi-cylindrical member (282), which is a portion of clamp arm assembly (280) positioned adjacent to a top surface of outer sheath (232), via a pin (245). Clamp arm (244) is operable to rotate about pin (245). A distal end of inner tube (234) is rotatably and slidably coupled with a proximal end of clamp arm (244) via a pair of pins (235). Each pin (235) is disposed within a respective slot (233) formed in a distal end of inner tube (234) such that longitudinal translation of inner tube (234) relative to outer sheath (232) and pivot arm assembly (280) causes rotation of clamp arm (244) about pin (245) toward and away from ultrasonic blade (260) to thereby clamp tissue between clamp pads (246, 248) and ultrasonic blade (260) to cut and/or seal the tissue. In particular, proximal longitudinal translation of inner tube (234) relative to outer sheath (232) and pivot arm assembly (280) causes clamp arm (244) to rotate about pin (245) toward ultrasonic blade (260); and distal longitudinal translation of inner tube (234) relative to outer sheath (232) and pivot arm assembly (280) causes clamp arm (244) to rotate about pin (245) away from ultrasonic blade (260).

As mentioned above, the distal end of inner tube (234) is slidably coupled with the proximal end of clamp arm (244) via pins (235) disposed within slots (233). Pins (235) are operable to translate vertically within the respective slots (233) such that clamp arm (244) is operable to pivot about pins (237) between an upward vertical position (FIGS. 18A-18B) and a downward vertical position (FIG. 18C). As will be discussed in more detail below, rotation of pivot arm assembly (280) causes this pivotal movement of clamp arm (244) about pins (237) to thereby clamp tissue between clamp pads (246, 248) and ultrasonic blade (260) to cut and/or seal the tissue. In particular, counter-clockwise rotation of pivot arm assembly (280) relative to outer sheath (232) and inner tube (234) causes clamp arm (244) to pivot about pins (237) downwardly toward ultrasonic blade (260); and clockwise rotation of pivot arm assembly (280) relative to outer sheath (232) and inner tube (234) causes clamp arm (244) to pivot about pins (237) upwardly away from ultrasonic blade (260). As noted above, this motion of clamp arm (244) is nearly vertical, such that it may appear that clamp arm (244) is translating vertically relative to blade (260).

Figure 8:
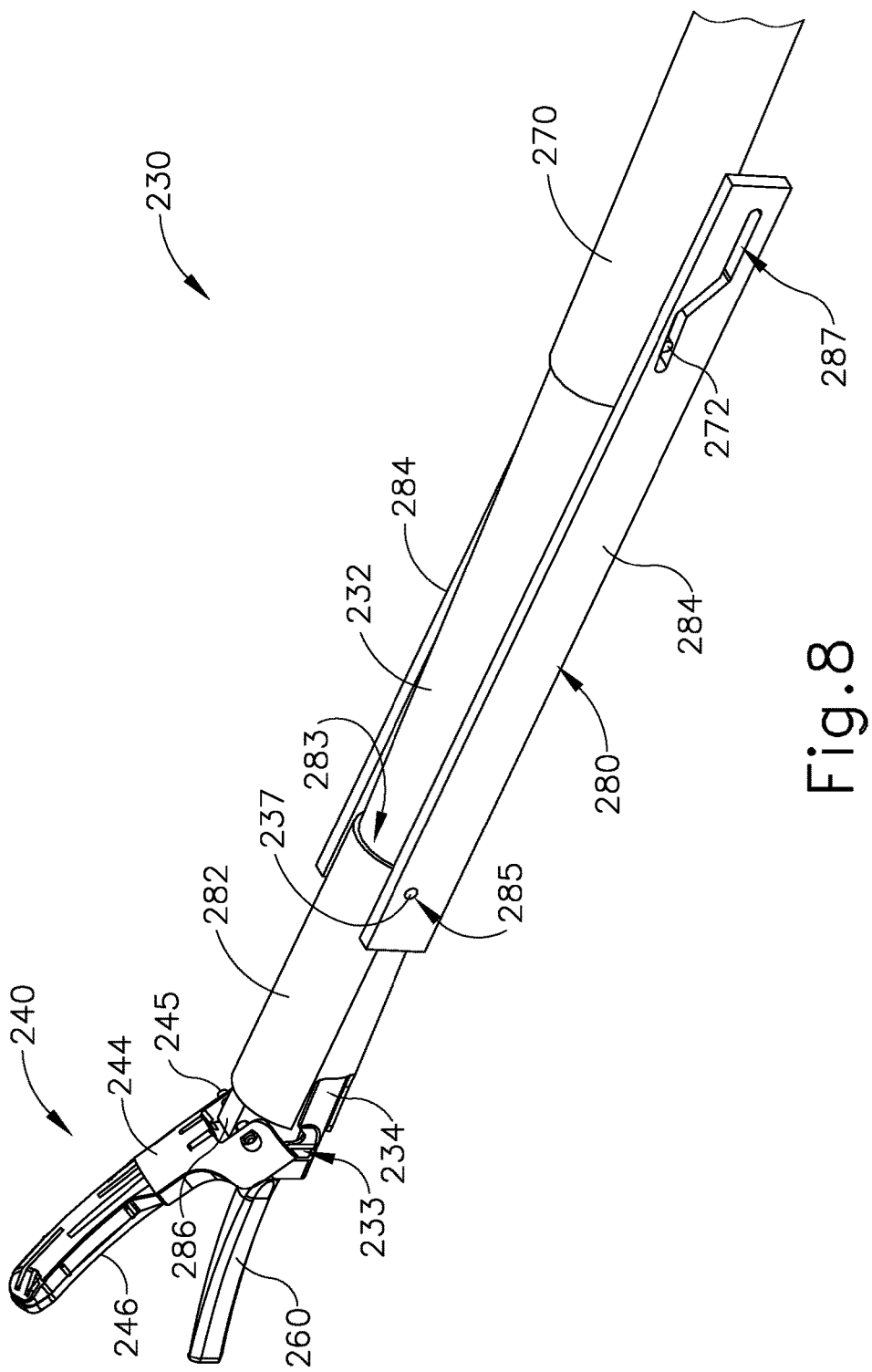
FIG. 8 depicts a perspective view of a shaft assembly and end effector of the instrument of FIG. 6.
Figure 11:
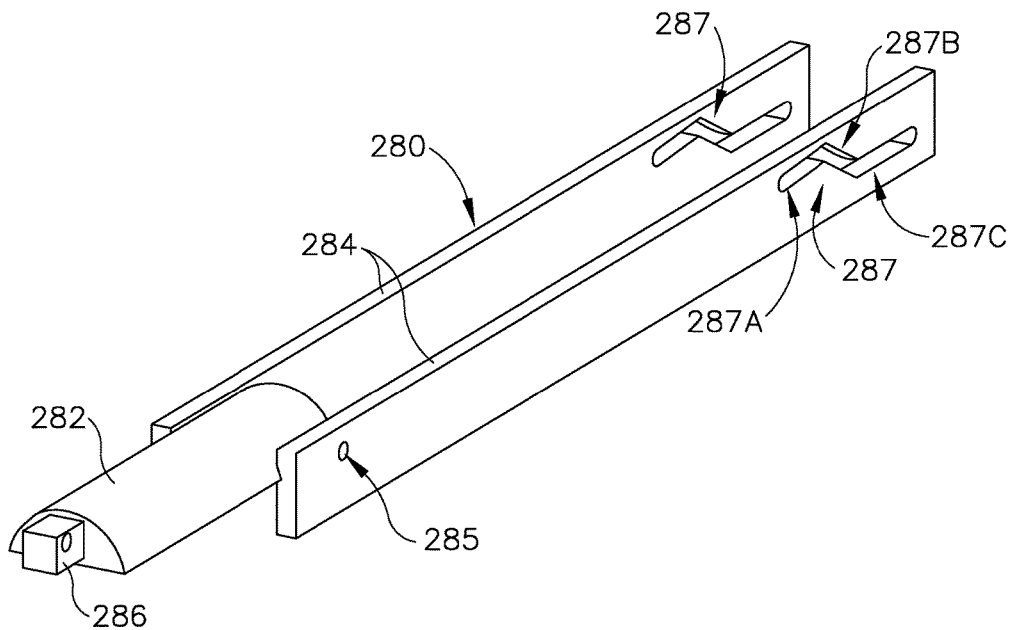
FIG. 11 depicts a perspective view of a pivot arm of the shaft assembly and end effector of FIG. 8.
Figure 12:
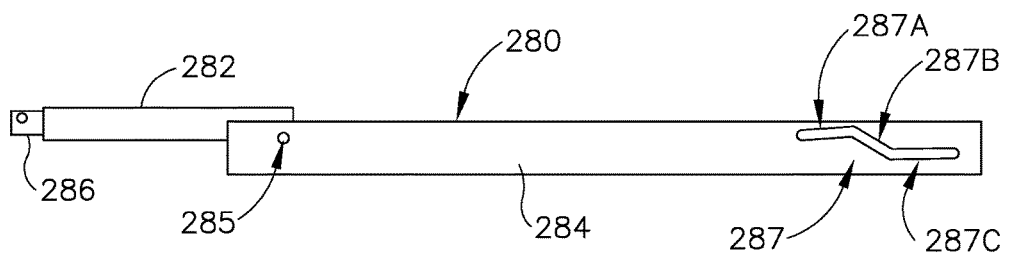
FIG. 12 depicts a side elevational view of the pivot arm of FIG. 11.
Figure 14:
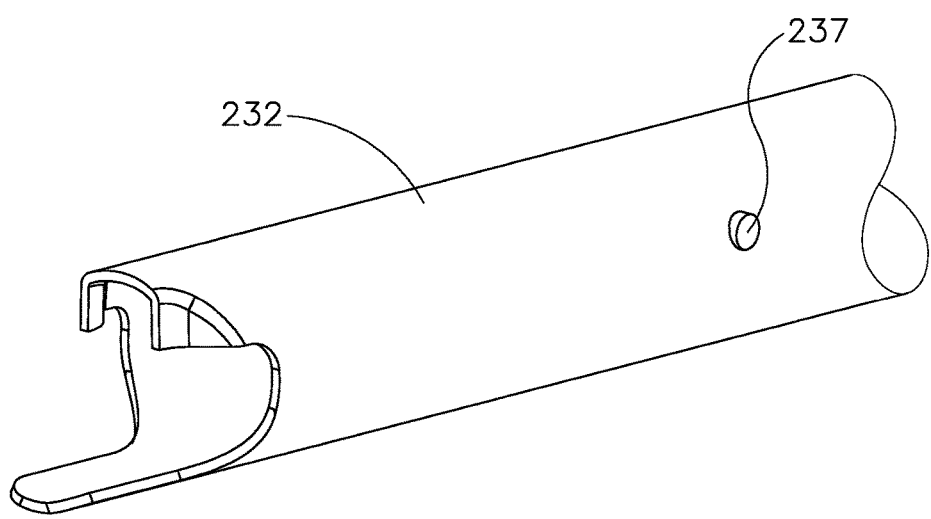
FIG. 14 depicts a perspective view of a distal portion of an outer sheath of the shaft assembly of FIG. 8.
Figure 15:
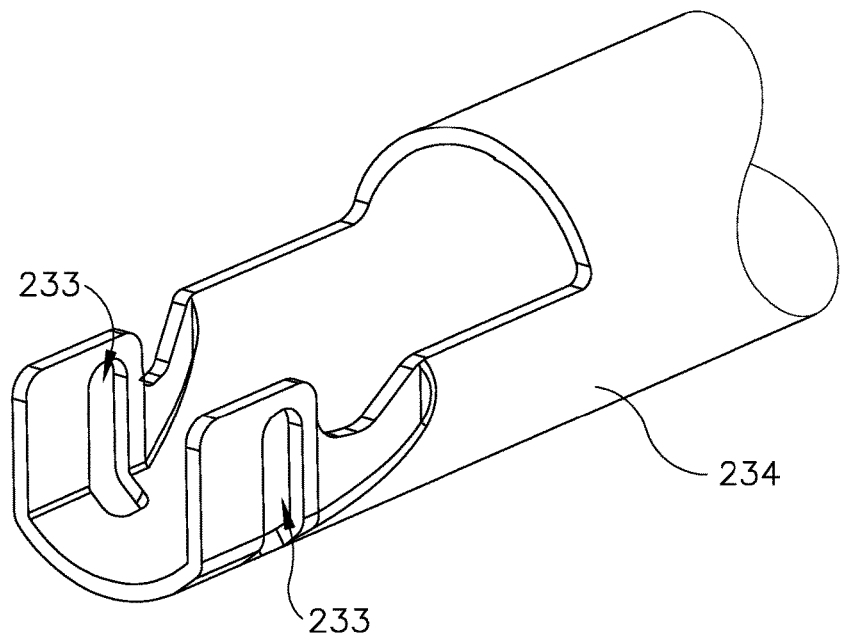
FIG. 15 depicts a perspective view of a distal portion of an inner tube of the shaft assembly of FIG. 8.

As best seen in FIGS. 11 and 12, pivot arm assembly (280) comprises a semi-cylindrical member (282) and a pair of elongate-plate members (284). Elongate-plate members (284) extend proximally from a proximal end of semi-cylindrical member (282) parallel to one another such that a gap is defined between interior surfaces of elongate-plate members (284). Shaft assembly (230) is configured to be received within this gap such that elongate-plate members (284) are at least partially disposed about outer sheath (232) and pivot tube (270). Pivot arm assembly (280) further includes a pair of pinholes (285) formed in a distal portion of elongate-plate members (284). As best seen in FIG. 14, outer sheath (232) comprises a pair of pins (237) extending transversely from an exterior surface of outer sheath (232). Pins (237) are configured to be pivotably received within pinholes (285) of elongate-plate members (284) such that pivot arm assembly (280) is pivotably coupled with outer sheath (232) and such that pivot arm assembly (280) is operable to rotate about pins (237) of outer sheath (232). As best seen in FIG. 8, pivot arm assembly (280) is coupled with outer sheath (232) such that semi-cylindrical member (282) is positioned adjacent to a top surface of outer sheath (232). A proximal portion of semi-cylindrical member (282) comprises a semi-circular recess (283) formed therein such that at least a portion of outer sheath (232) may be received within semi-cylindrical member (282) as pivot arm assembly (280) rotates about pins (237).

Figure 13:
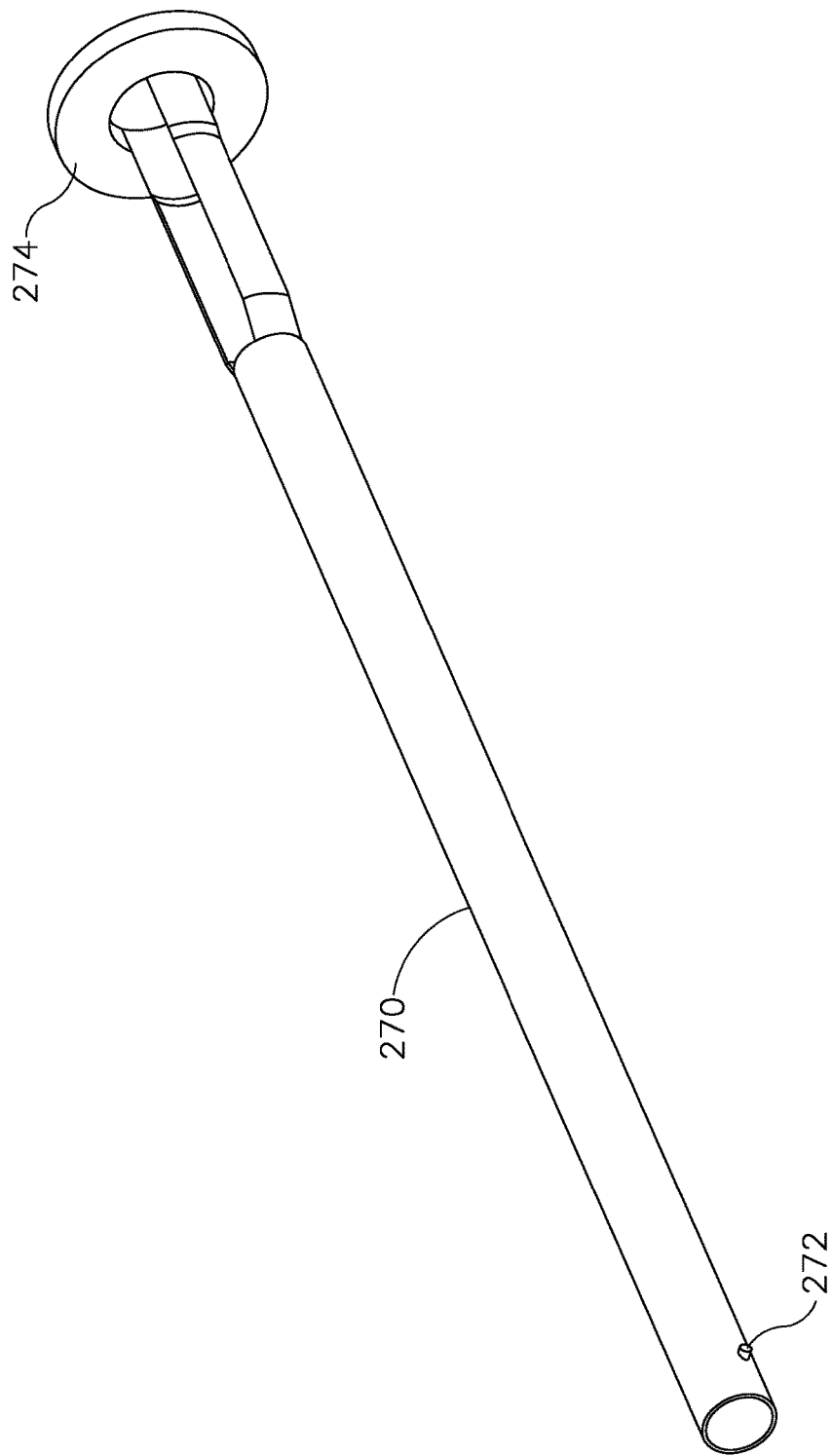
FIG. 13 depicts a perspective view of a pivot tube of the shaft assembly of FIG. 8.

Pivot arm assembly (280) further includes a pair of slots (287) formed in a proximal portion of elongate-plate members (284). As best seen in FIG. 13, pivot tube (270) comprises a pair of pins (272) extending from an exterior surface of pivot tube (270). Pins (272) are slidably and pivotably received within slots (287) of elongate-plate members (284) such that pivot arm assembly (280) is pivotably and slidably coupled with pivot tube (270). As best seen in FIG. 12, slots (287) include a distal portion (287A), a proximal portion (287C), and an intermediate portion (287B). Portions (287A, 287B, 287C) together provide a dogleg configuration. Distal portion (287A) is formed in a top portion of elongate-plate members (284) and is slightly angled obliquely relative to the longitudinal axis of elongate-plate members (284) such that, as will be discussed in more detail below, with pivot arm assembly (280) oriented at a similar angle, distal portion (287A) is substantially horizontal. Proximal portion (287C) is formed in a bottom portion of elongate-plate members (284) and is also slightly angled obliquely relative to the longitudinal axis of elongate-plate members (284) such that, as will be discussed in more detail below, with pivot arm assembly (280) oriented at a similar angle, proximal portion (287C) is substantially horizontal. Finally, intermediate portion (287B) is also angled obliquely relative to the longitudinal axis of elongate-plate members (284) and provides for angular transition between a proximal end of distal portion (287A) and a distal end of proximal portion (287C).

As will be discussed in more detail below, pivot tube (270) is operable to translate longitudinally about outer sheath (232), relative to outer sheath (232) and handle assembly (220), so as to cause translation of pins (272) within slots (287) to thereby selectively rotate pivot arm assembly (280) about pins (237) of outer sheath (232). In particular, proximal longitudinal translation of pivot tube (270) relative to outer sheath (232) and handle assembly (220) causes counter-clockwise rotation of pivot arm assembly (280) about pins (237) of outer sheath (232); and distal longitudinal translation of pivot tube (270) relative to outer sheath (232) and handle assembly (220) causes clockwise rotation of pivot arm assembly (280) about pins (237) of outer sheath (232).

Pivot arm assembly (280) further comprises a projection (286) extending distally from a distal end of semi-cylindrical member (282). Clamp arm (244) is pivotably coupled with projection (286) of pivot arm assembly (280) via pin (245) such that, as discussed above, rotation of pivot arm assembly (280) about pins (237) of outer sheath (232) causes nearly or mostly vertical translation of clamp arm (244) within slot (233). In particular, counter-clockwise rotation of pivot arm assembly (280) about pins (237) of outer sheath (232) causes clamp arm (244) to translate nearly or mostly vertically downwardly toward ultrasonic blade (260); and clockwise rotation of pivot arm assembly (280) about pins (237) of outer sheath (232) causes clamp arm (244) to translate nearly or mostly vertically upwardly away from ultrasonic blade (260). It should therefore be understood that proximal longitudinal translation of pivot tube (270) relative to outer sheath (232) and handle assembly (220) causes counter-clockwise rotation of pivot arm assembly (280) about pins (237) of outer sheath (232), which in turn causes clamp arm (244) to translate nearly or mostly vertically downwardly toward ultrasonic blade (260); and distal longitudinal translation of pivot tube (270) relative to outer sheath (232) and handle assembly (220) causes clockwise rotation of pivot arm assembly (280) about pins (237) of outer sheath (232), which in turn causes clamp arm (244) to translate nearly or mostly vertically upwardly away from ultrasonic blade (260). Again, the movement of clamp arm (244) is not exactly vertical because clamp arm (244) is actually pivoting about pins (237), though the motion may appear to be vertical because pins (237) are spaced so far proximal of clamp arm (244).

Figure 16:
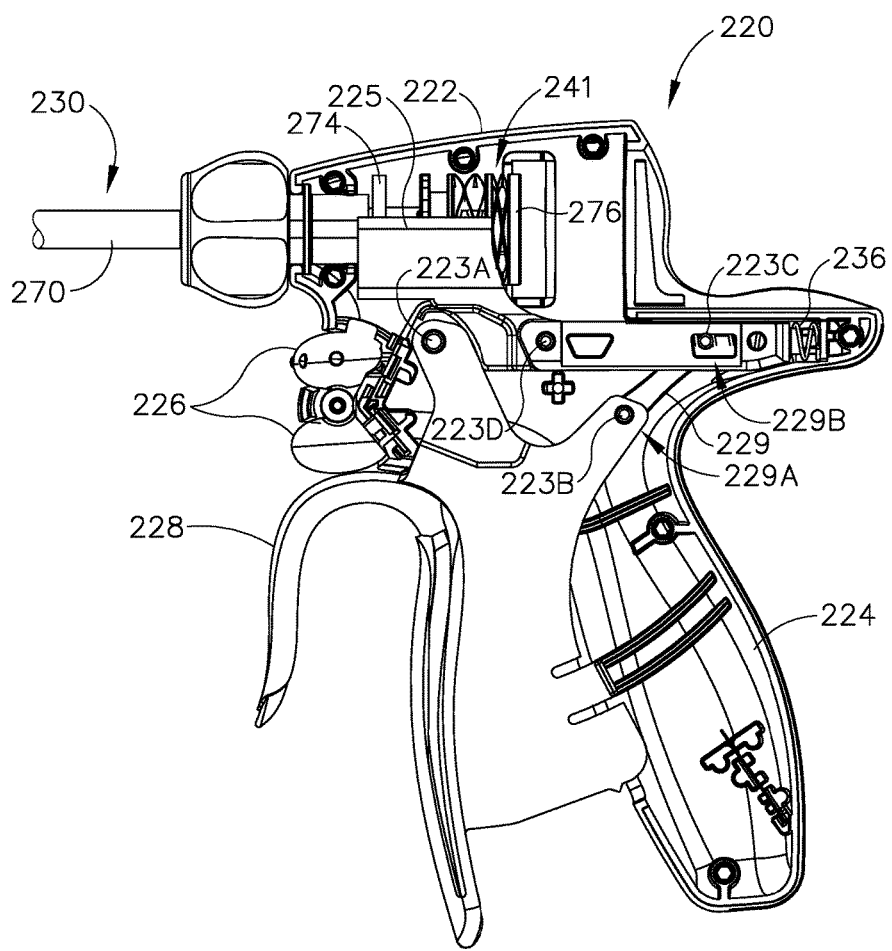
FIG. 16 depicts a side elevational view of a handle assembly of the instrument of FIG. 6 with a housing shroud removed.

As shown in FIG. 16, trigger (228) is pivotably coupled to handle assembly (220) via a pin (223A) such that trigger (228) is operable to rotate about pin (223A). As will be described in more detail below, trigger (228) is coupled with a yoke (225) via a linkage (229) such that rotation of trigger (228) about pin (223A) causes longitudinal translation of yoke (225). A first end (229A) of linkage (229) is rotatably coupled with a proximal portion of trigger (228) via a pin (223B). A second end (229B) of linkage (229) is rotatably coupled with a proximal portion of yoke (225) via a pin (223C). Pin (223C) passes completely through the proximal portion of yoke (225) and second end (229B) of linkage (229) such that ends of pin (223C) extend from opposite sides of yoke (225). These ends of pin (223C) are slidably and rotatably disposed within slots (not shown) formed in interior surfaces of body (222) of handle assembly (220). A pin (223D) passes completely through a distal portion of yoke (225) such that ends of pin (223D) extend from opposite sides of yoke (225). These ends of pin (223D) are also slidably and rotatably disposed within the slots formed in the interior surfaces of body (222). Pins (223C, 223D) are thus configured to longitudinally translate within these slots in body (222). This slidability of pins (223C, 223D) enables yoke (225) to longitudinally translate within body (222) between a proximal longitudinal position and a distal longitudinal position. Because the proximal portion of trigger (228) is coupled with yoke (225) via linkage (229), pivoting of trigger (228) toward and away from pistol grip (224) will cause longitudinal translation of yoke (225) within body (222). In particular, pivoting of trigger (228) toward pistol grip (224) will cause proximal longitudinal translation of yoke (225); and pivoting of trigger (228) away from pistol grip (224) will cause distal longitudinal translation of yoke (225).

A distal portion of yoke (225) engages a flange (274) of pivot tube (270) such that longitudinal translation of yoke (225) causes concurrent longitudinal translation of pivot tube (270). The distal portion of yoke (225) further engages an integral flange (276) of inner tube (234) via a plurality of wave springs (241) that are disposed between yoke (225) and flange (276) of inner tube (234) such that longitudinal translation of yoke (225) causes concurrent longitudinal translation of pivot tube (270). As discussed above, inner tube (234) is longitudinally translatable within outer sheath (232), such that inner tube (234) is configured to longitudinally translate concurrently with yoke (225). Also as discussed above, pivot tube (270) is longitudinally translatable about outer sheath (232), such that pivot tube (270) is configured to longitudinally translate concurrently with yoke (225). Furthermore, because pivoting of trigger (228) toward pistol grip (224) causes proximal longitudinal translation of yoke (225), it should be understood that pivoting of trigger (228) toward pistol grip (224) will cause proximal longitudinal translation of inner tube (234) and pivot tube (270) relative to outer sheath (232) and handle assembly (220). Similarly, because pivoting of trigger (228) away from pistol grip (224) causes distal longitudinal translation of yoke (225), it should be understood that and that pivoting of trigger (228) away from pistol grip (224) will cause distal longitudinal translation of inner tube (234) and pivot tube (270) relative to outer sheath (232) and handle assembly (220). Because longitudinal translation of inner tube (234) causes rotation of clamp arm (244) toward and away from blade (260) as discussed above, it should be understood that pivoting of trigger (228) toward pistol grip (224) will cause clamp arm (244) to move toward ultrasonic blade (260). Similarly, pivoting of trigger (228) away from pistol grip (224) will cause clamp arm (244) to move away from ultrasonic blade (260). Finally, because longitudinal translation of pivot tube (270) causes rotation of pivot arm assembly (280) as discussed above, it should be understood that pivoting of trigger (228) toward pistol grip (224) will cause counter-clockwise rotation of pivot arm assembly (280) about pins (237). Similarly, pivoting of trigger (228) away from pistol grip (224) will cause clockwise rotation of pivot arm assembly (280) about pins (237).

However, as will be discussed in more detail below, longitudinal translation of inner tube (234) is limited by pin (231)—which secures waveguide (202) within shaft assembly (230) via outer sheath (232)—such that pivoting of trigger (228) toward pistol grip (224) beyond a predetermined point does not cause proximal longitudinal translation of inner tube (234). In particular, pin (231) passes through a longitudinal slot (239) formed in inner tube (234) (best seen in FIG. 10) such that inner tube (234) is operable to translate no more than the length of slot (239).

Figure 7:
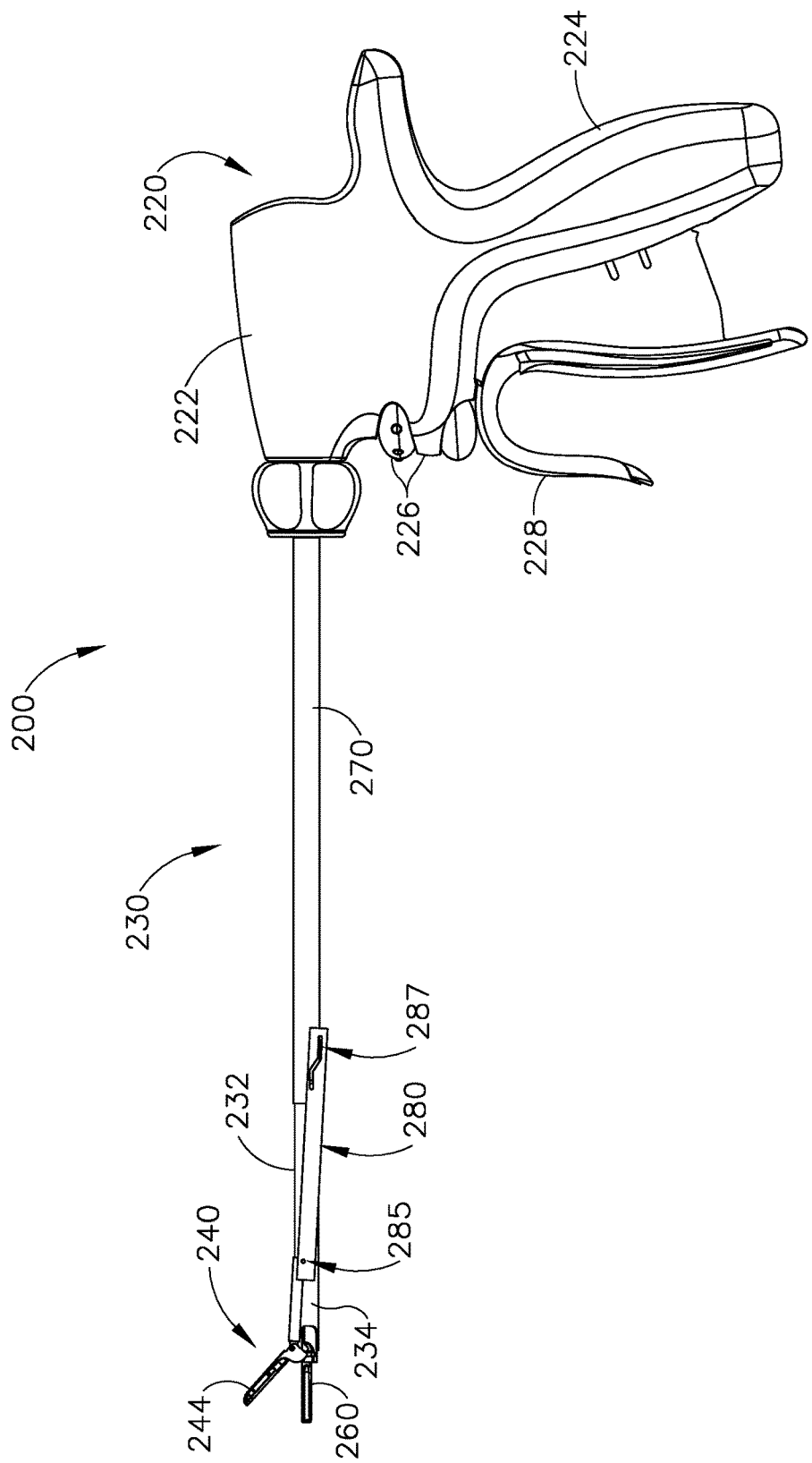
FIG. 7 depicts a side elevational view of the instrument of FIG. 6.

In some versions, one or more resilient members are used to bias clamp arm (244), pivot arm assembly (280), and/or trigger (228) to the open position shown in FIG. 7. For instance, as best seen in FIG. 16, a spring (236) is positioned within a proximal end of body (222) of handle assembly (220). Spring (236) bears against body (222) and a proximal end of yoke (225) to thereby bias yoke (225) toward the distal position. Biasing of yoke (225) toward the distal position causes inner tube (234) and pivot tube (270) to be biased distally and further causes trigger (228) to be biased away from pistol grip (224).

Figure 17A:
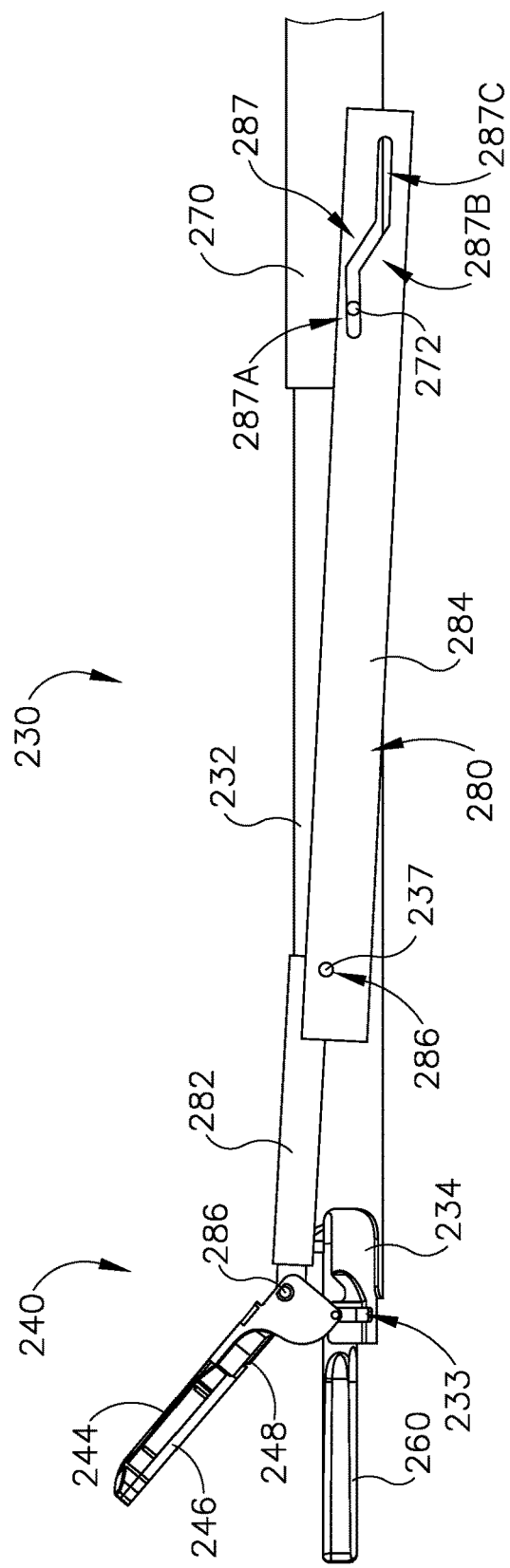
FIG. 17A depicts a side elevational view of the shaft assembly and end effector of FIG. 8 with the pivot tube of FIG. 13 in a first longitudinal position, with the pivot arm of FIG. 11 in a first rotational position, with the inner tube of FIG. 15 in a first longitudinal position, and with a clamp arm of the end effector in a first vertical position and a first rotational position.

FIGS. 17A-19C show the operation of instrument (200). FIG. 17A shows end effector (240) and shaft assembly (230) in an initial position. In this position, inner tube (234) is in a distal longitudinal position relative to outer sheath (232) and handle assembly (220) such that clamp arm (244) is in an open position. Also in this initial position, pivot tube (270) is in a distal longitudinal position relative to outer sheath (232) and handle assembly (220) such that pins (272) are positioned within a distal end of distal portion (287A) of slots (287), such that pivot arm assembly (280) is in a first rotational position. As best seen in FIG. 18A, with pivot arm assembly (280) in the first rotational position, pins (235) of clamp arm (244) are in an upward vertical position within slots (233) of inner tube (234).

Figure 19A:
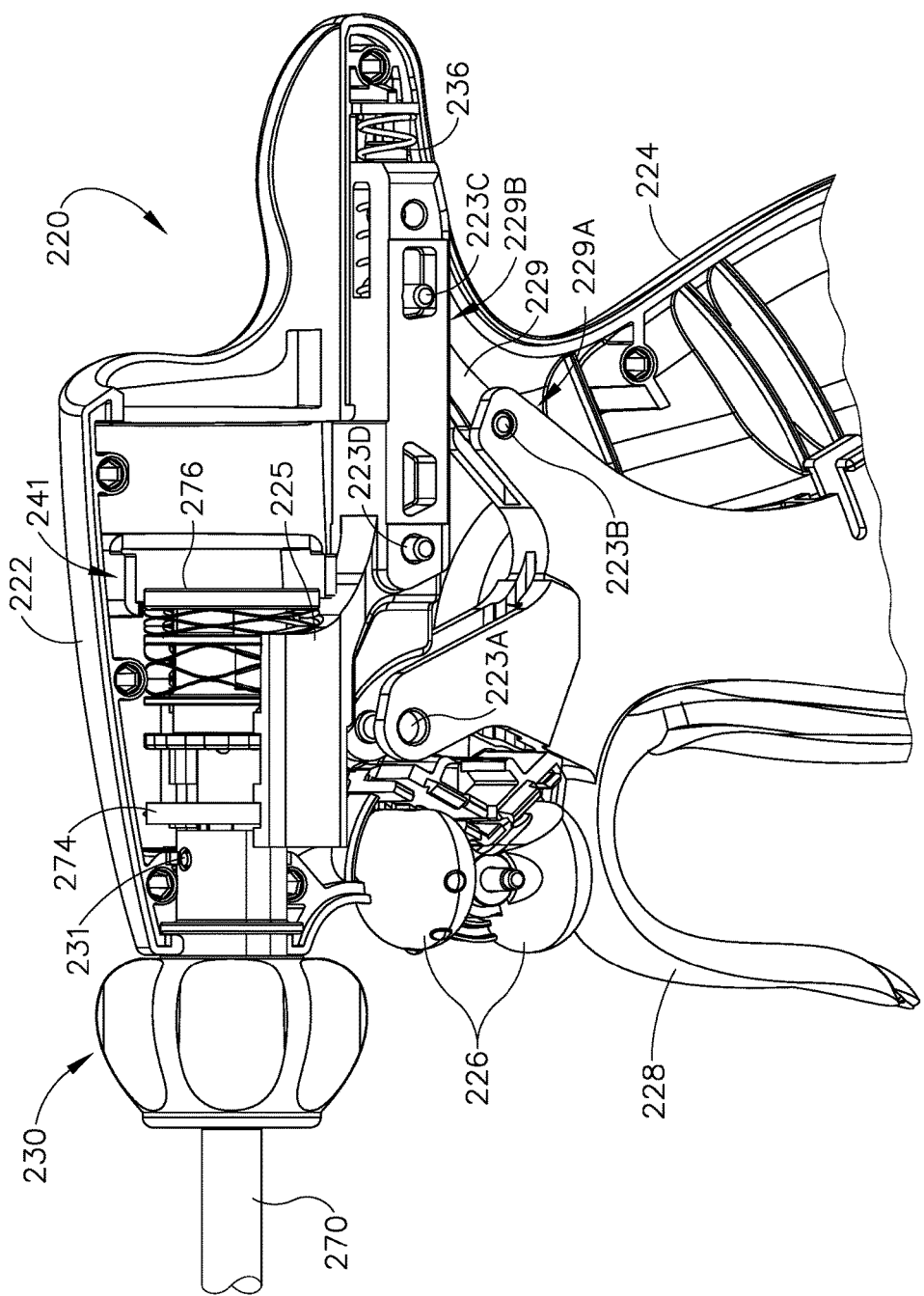
FIG. 19A depicts a side perspective view of the handle assembly of FIG. 16 with a housing shroud removed, with a trigger of the handle assembly in a first rotational position, with the inner tube of FIG. 15 in the first longitudinal position, and with the clamp arm of FIG. 17A in the first vertical position and the first rotational position.
Figure 19B:
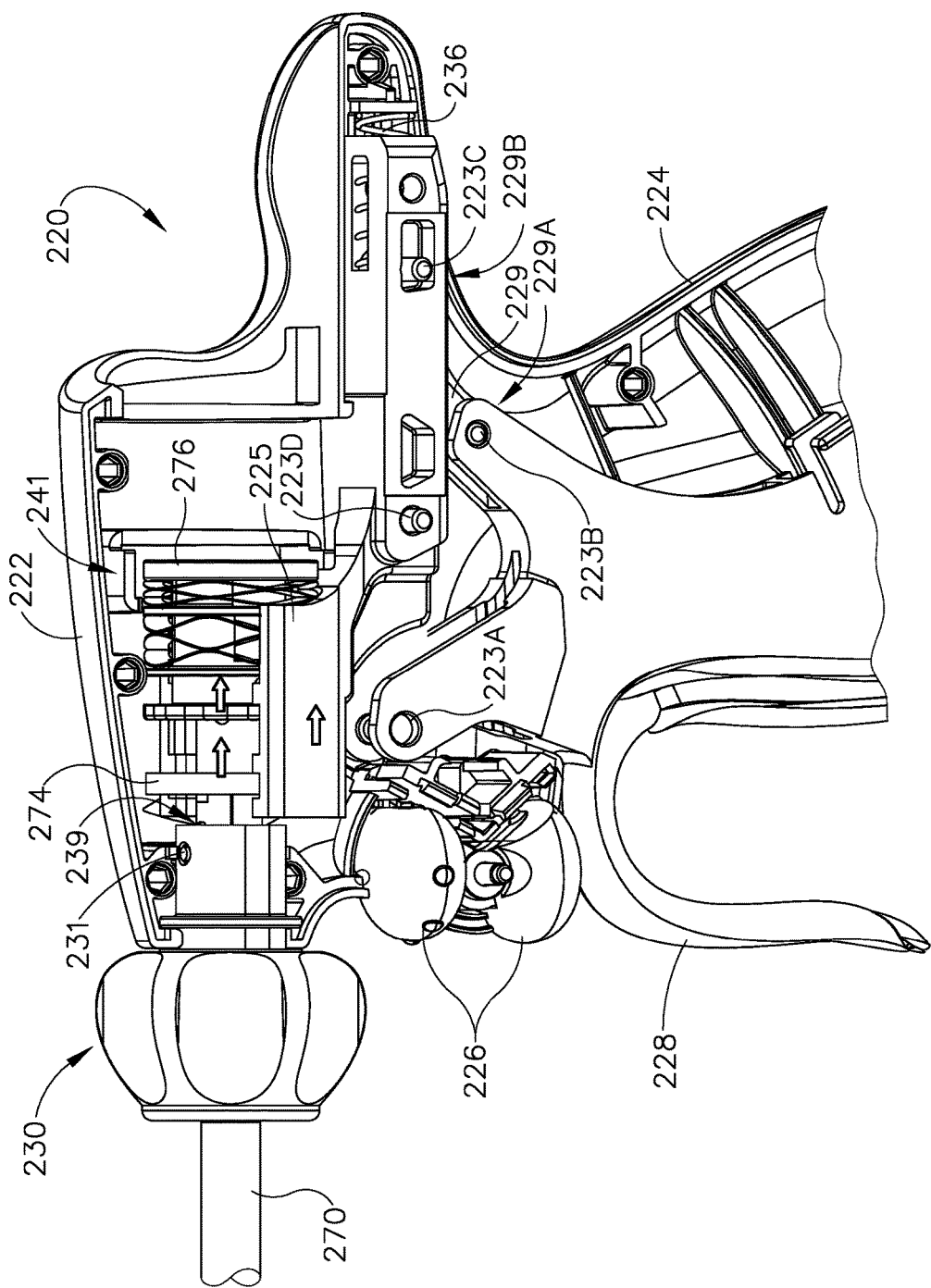
FIG. 19B depicts a side perspective view of the handle assembly of FIG. 16 with a housing shroud removed, with the pivot tube of FIG. 13 and the inner tube of FIG. 15 moved to the second longitudinal positions by rotation of the trigger of FIG. 19A to a second rotational position.

FIG. 19A shows shaft assembly (230) and handle assembly (220) in the initial position. In this position, trigger (228) is in a first rotational position away from pistol grip (224) such that yoke (225) is in a distal longitudinal position. As trigger (228) is rotated toward pistol grip (224) to a second rotational position, yoke (225) is translated longitudinally proximally as shown in FIG. 19B. As discussed above, proximal longitudinal translation of yoke (225) causes proximal longitudinal translation of inner tube (234) and pivot tube (270) relative to outer sheath (232) and relative to handle assembly (220). As pivot tube (270) is translated longitudinally proximally by rotation of trigger (228) from the first rotational position (FIG. 19A) to the second rotational position (FIG. 19B), pins (272) of pivot tube (270) translate within slots (287) from the distal end of distal portion (287A) to the proximal end of distal portion (287A). As shown in FIG. 17A, and as discussed above, distal portion (287A) is slightly angled relative to elongate-plate members (284) such that distal portion (287A) is substantially horizontal with pivot arm assembly (280) in the first rotational position. It should therefore be understood that as pivot tube (270) is translated longitudinally proximally by rotation of trigger (228) through a first range of motion from the first rotational position (FIG. 19A) to the second rotational position (FIG. 19B), pins (272) translate within distal portion (287A) of slots (287) without causing substantial rotation of pivot arm assembly (280). Because rotation of pivot arm assembly (280) causes nearly or mostly vertical translation of clamp arm (244), it should be appreciated that clamp arm (244) remains in the upward vertical position within slot (233) of inner tube (234) as trigger (228) rotates through the first range of motion from the first rotational position (FIG. 19A) to the second rotational position (FIG. 19B).

As inner tube (234) is translated longitudinally proximally by rotation of trigger (228) from the first rotational position (FIG. 19A) to the second rotational position (FIG. 19B), inner tube (234) causes clamp arm (244) to pivot toward ultrasonic blade (260) into a partially closed, or "seal-only," position. In this "seal-only" position, clamp arm (244) is oriented substantially parallel to blade (260). Because, as discussed above, clamp arm (244) remains in the upward vertical position within slot (233) of inner tube (234) a gap (G) remains between clamp pads (246, 248) and blade (260), as best seen in FIG. 18B. Gap (G) between clamp pads (246, 248) and blade (260) is configured to minimize a clamping pressure applied to tissue captured between clamp arm (244) and blade (260) such that blade (260) is operable to seal or weld the tissue, but not cut the tissue in this position. It should be appreciated that handle assembly (220), shaft assembly (230), and/or end effector (240) may include features that are configured to provide tactile or auditory feedback to the operator to signal that clamp arm (244) has reached this "seal-only" position. Furthermore, as inner tube (234) is translated longitudinally proximally by rotation of trigger (228) through the first range of motion from the first rotational position (FIG. 19A) to the second rotational position (FIG. 19B), pin (231) translates within slot (239) of inner tube (234) from a proximal end of slot (239) to a distal end of slot (239) such that inner tube (234) is inoperable to translate further proximally. Thus, because inner tube (234) is inoperable to translate further longitudinally proximally, it should be understood that clamp arm (244) is inoperable to pivot further toward ultrasonic blade (260) at this stage. It should also be appreciated that wave springs (241) will accommodate further longitudinal translation of yoke (225).

Figure 19C:
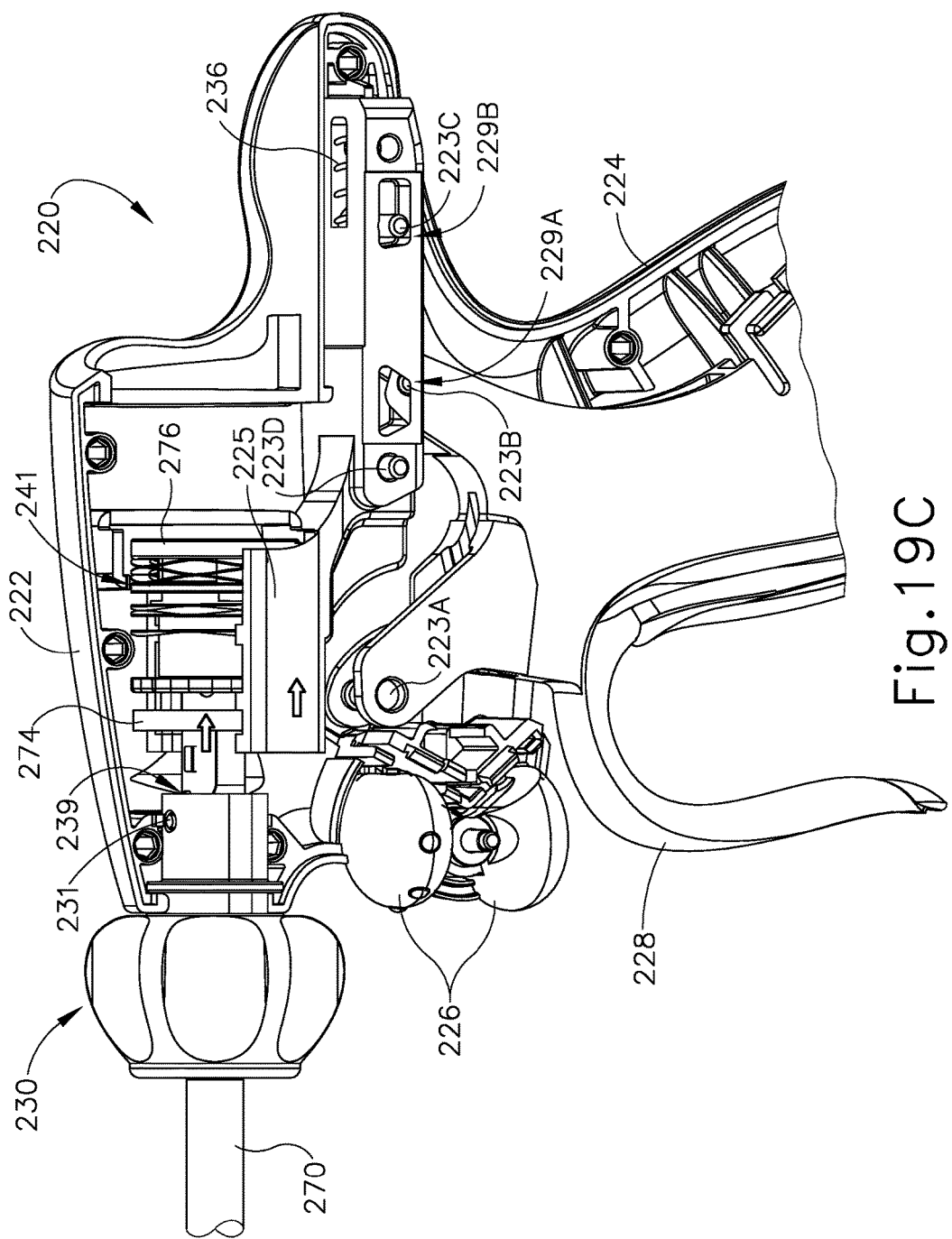
FIG. 19C depicts a side perspective view of the handle assembly of FIG. 16 with a housing shroud removed with the pivot tube of FIG. 13 moved to the third longitudinal position by rotation of the trigger of FIG. 19A to a third rotational position.

As trigger (228) is rotated further toward pistol grip (224) through a second range of motion to a third rotation position, yoke (225) is further translated longitudinally proximally as shown in FIG. 19C. Further proximal longitudinal translation of yoke (225) causes further proximal longitudinal translation of pivot tube (270) relative to outer sheath (232) and handle assembly (220). As pivot tube (270) is further translated longitudinally proximally, pins (272) translate proximally within intermediate portion (287B) of slots (287) between the proximal end of distal portion (287A) and the distal end of proximal portion (287C). As pins (272) translate within slots (287), pivot arm assembly (280) is rotated counter-clockwise about pins (237) into a second rotational position as shown in FIG. 17C. As pivot arm assembly (280) is rotated counter-clockwise about pins (237), clamp arm (244) is translated nearly or mostly vertically downwardly into the downward vertical position as pins (235) travel downwardly within slots (233) of inner tube (234) into a completely closed, or "cut-and-seal," position. In particular, clamp arm (244)—while remaining oriented substantially parallel to blade (260)—is translated nearly or mostly vertically downwardly toward blade (260) so as to increase pressure applied to tissue captured between clamp arm (244) and blade (260) such that blade (260) is operable to substantially simultaneously cut and seal or weld the tissue. It should be appreciated that handle assembly (220), shaft assembly (230), and/or end effector (240) may include features that are configured to provide tactile or auditory feedback to the operator to signal that clamp arm (244) has reached this "seal-and-cut" position.

As shown in FIG. 17C, and as discussed above, proximal portion (287C) is slightly angled relative to elongate-plate members (284) such that proximal portion (287C) is substantially horizontal with pivot arm assembly (280) in the second rotational position. It should therefore be understood that as pivot tube (270) is further translated longitudinally proximally by rotation of trigger (228) beyond the third rotational position (FIG. 19C), pins (272) translate within proximal portion (287C) of slots (287) without causing substantial rotation of pivot arm assembly (280). Because rotation of pivot arm assembly (280) causes vertical translation of clamp arm (244), it should be appreciated that clamp arm (244) remains in the downward vertical position if trigger (228) rotates beyond the third rotational position (FIG. 19C).

When the operator relaxes their grip on trigger (228) or otherwise moves trigger (228) away from grip (224), trigger (228) may eventually return to the position shown in FIG. 19A. As trigger (228) travels through this range of motion, pivot arm assembly (280) rotates clockwise back from the position shown in FIG. 17C to the position shown in FIG. 17B, returning clamp arm (244) from the downward position shown in FIG. 18C to the upward position shown in FIG. 18B. In addition, inner tube (234) translates distally from the position shown in FIGS. 17B-17C to the position shown in FIG. 17A, returning clamp arm (244) back to the fully open position shown in FIG. 18A.

B. Exemplary Ultrasonic Surgical Instrument with Shortened Pivot Arm

Figure 20:
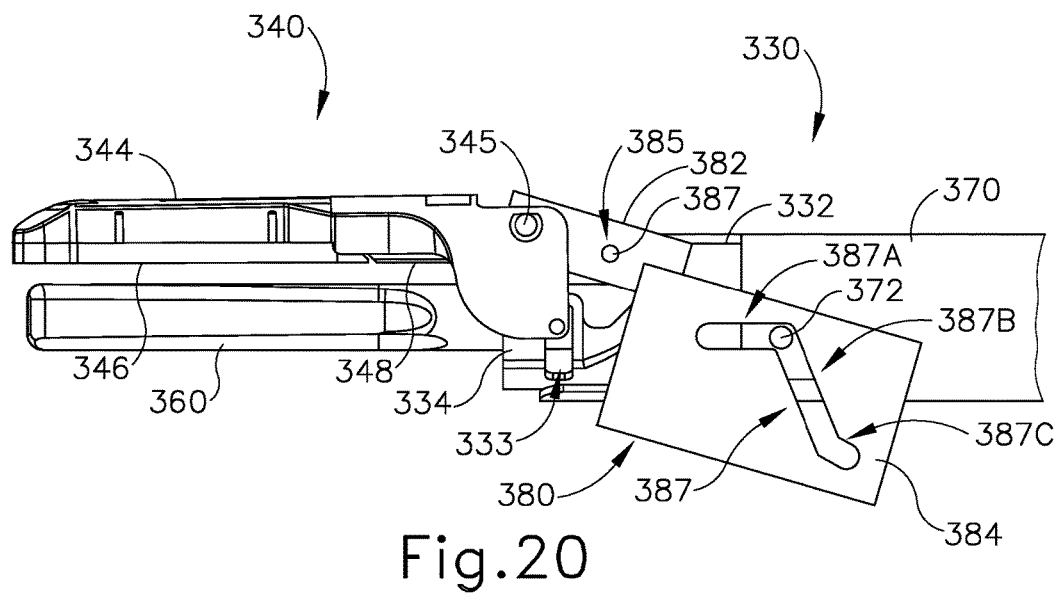
FIG. 20 depicts a detailed side elevational view of an exemplary alternative shaft assembly and end effector operable for use with the instrument of FIG. 6.

FIG. 20 depicts an exemplary shaft assembly (330) and end effector (340) that may be readily incorporated into instrument (200) in place of shaft assembly (230) and end effector (240). Shaft assembly (330) and end effector (340)

are configured to operate substantially similar to shaft assembly (230) and end effector (240) discussed above except for the differences discussed below. In particular, shaft assembly (330) and end effector (340) are configured to selectively clamp tissue between a clamp arm (344) and an ultrasonic blade (360) of end effector (340) in a "seal-only" operation, in which blade (360) is operable to seal or weld tissue without cutting the tissue; and in a "cut-and-seal" operation, in which blade (360) is operable to cut tissue and seal or weld tissue substantially simultaneously.

Shaft assembly (330) of the present example comprises an outer sheath (332), an inner tube (334), a pivot tube (370), and a pivot arm assembly (380). Inner tube (334) is slidably disposed within outer sheath (332). As with shaft assembly (230) discussed above, inner tube (334) is operable to translate longitudinally within outer sheath (332) relative to outer sheath (332) to selectively pivot clamp arm (344) toward and away from blade (360). Pivot tube (370) is slidably disposed about outer sheath (332) such that pivot tube (370) is operable to translate longitudinally about outer sheath (332) relative to outer sheath (332). Pivot arm assembly (380) is pivotably coupled with outer sheath (332). Pivot arm assembly (380) is further pivotably and slidably coupled with pivot tube (370). Pivot tube (370) of the present example, however, is substantially longer than pivot tube (270) discussed above; and pivot arm assembly (380) of the present example is substantially shorter than pivot arm assembly (280) discussed above. Thus, pivot arm assembly (380) is coupled with pivot tube (370) at a distal end of shaft assembly (230). As with pivot tube (270) discussed above, pivot tube (370) is operable to translate longitudinally about outer sheath (332) relative to outer sheath (332) to selectively rotate pivot arm assembly (380) about outer sheath (332) to thereby translate clamp arm (344) nearly or mostly vertically toward and away from blade (360) via a slot (333) formed within a distal end of inner tube (334). It should there be understood that, as with shaft assembly (230) and end effector (240) discussed above, a combination of rotation and nearly or mostly vertical translation of clamp arm (344) relative to blade (360) is configured to selectively change instrument (300) between a "seal-only" operation and a "cut-and-seal" operation.

End effector (340) of the present example comprises clamp arm (344) and ultrasonic blade (360). Clamp arm (344) includes a primary clamp pad (346) and a secondary clamp pad (348) that are secured to an underside of clamp arm (344), facing blade (360). Clamp arm (344) is operable to selectively pivot toward and away from blade (360) to selectively clamp tissue between clamp pads (346, 348) and blade (360). As will be discussed in more detail below, clamp arm (344) is pivotably coupled with a distal end of pivot arm assembly (380) via a pin (345) such that clamp arm (344) is operable to rotate about the distal end of pivot arm assembly (380). A distal end of inner tube (334) is rotatably and slidably coupled with a proximal end of clamp arm (344) via a pair of pins (335) that are disposed within respective slots (333) that are formed in a distal end of inner tube (334) such that longitudinal translation of inner tube (334) relative to sheath (332) causes rotation of clamp arm (344) about the distal end of pivot arm assembly (380) toward and away from ultrasonic blade (360) to thereby clamp tissue between clamp pads (346, 348) and ultrasonic blade (360) to cut and/or seal the tissue. In particular, proximal longitudinal translation of inner tube (334) relative to outer sheath (332) causes clamp arm (344) to rotate about the distal end of pivot arm assembly (380) via pin (345) toward ultrasonic blade (360); and distal longitudinal translation of inner tube (334) relative to outer sheath (332) causes clamp arm (344) to rotate about the distal end of pivot arm assembly (380) via pin (345) away from ultrasonic blade (360).

As mentioned above, the distal end of inner tube (334) is slidably coupled with the proximal end of clamp arm (344) via pins (335) disposed within slots (333) such that clamp arm (344) is operable to translate vertically within slot (333) between an upward vertical position and a downward vertical position. As will be discussed in more detail below, rotation of pivot arm assembly (380) causes vertical translation of clamp arm (344) toward ultrasonic blade (360) to thereby clamp tissue between clamp pads (346, 348) and ultrasonic blade (360) to cut and/or seal the tissue. In particular, counter-clockwise rotation of pivot arm assembly (380) about outer sheath (332) causes clamp arm (344) to translate vertically downwardly toward ultrasonic blade (360); and clockwise rotation of pivot arm assembly (380) about outer sheath (332) causes clamp arm (344) to translate vertically upwardly away from ultrasonic blade (360).

As with pivot arm assembly (280) discussed above, pivot arm assembly (380) comprises a semi-cylindrical member (382) and a pair of elongate-plate members (384). Elongate-plate members (384) extend proximally from a proximal end of semi-cylindrical member (382) and parallel to one another such that a gap is defined between interior surfaces of elongate-plate members (384). Shaft assembly (330) is configured to be received within this gap such that elongate-plate members (384) are at least partially disposed about outer sheath (332) and pivot tube (370). Pivot arm assembly (380) further comprises a pair of pinholes (385) formed in a proximal portion of semi-cylindrical member (382). Outer sheath (332) comprises a pair of pins (337) extending transversely from an exterior surface of a distal end of outer sheath (332). Pins (337) are pivotably received within pinholes (385) of semi-cylindrical member (382) such that pivot arm assembly (380) is pivotably coupled with the distal end of outer sheath (332) and such that pivot arm assembly (380) is operable to rotate about pins (337) of outer sheath (332).

Pivot arm assembly (380) further includes a pair of slots (387) formed in a proximal portion of elongate-plate members (384). Pivot tube (370) comprises a pair of pins (372) extending from an exterior surface of pivot tube (370). Pins (372) are slidably and pivotably received within slots (387) of elongate-plate members (384) such that pivot arm assembly (380) is pivotably and slidably coupled with pivot tube (370). Slots (387) include a distal portion (387A), a proximal portion (387C), and an intermediate portion (387B). Distal portion (387A) is formed in a top portion of elongate-plate members (384) and is slightly angled obliquely relative to elongate-plate members (384) such that, with pivot arm assembly (380) oriented at a similar angle, distal portion (387A) is substantially horizontal. Proximal portion (387C) is formed in a bottom portion of elongate-plate members (384) and is also slightly angled obliquely relative to elongate-plate members (384) such that, with pivot arm assembly (380) oriented at a similar angle, proximal portion (387C) is substantially horizontal. Finally, intermediate portion (387B) is also angled relative to elongate-plate members (384) and provides for angular transition between a proximal end of distal portion (387A) and a distal end of proximal portion (387C). As with pivot tube (270) discussed above, pivot tube (370) is operable to translate longitudinally about outer sheath (332) relative to outer sheath (332) so as to cause translation of pins (372) within slots (387) to thereby selectively rotate pivot arm assembly (380) about pins (337) of outer sheath (332). In particular, proximal longitudinal translation of pivot tube (370) relative to outer sheath (332) causes counter-clockwise rotation of pivot arm assembly (380) about pins (337) of outer sheath (332); and distal longitudinal translation of pivot tube (370) relative to outer sheath (332) causes clockwise rotation of pivot arm assembly (380) about pins (337) of outer sheath (332).

Clamp arm (344) is pivotably coupled with a distal end of semi-cylindrical member (382) of pivot arm assembly (380) via pin (345) such that, as discussed above, rotation of pivot arm assembly (380) about pins (337) of outer sheath (332) causes nearly or mostly vertical translation of clamp arm (344) within slot (333). In particular, counter-clockwise rotation of pivot arm assembly (380) about pins (337) of outer sheath (332) causes clamp arm (344) to translate nearly or mostly vertically downwardly toward ultrasonic blade (360); and clockwise rotation of pivot arm assembly (380) about pins (337) of outer sheath (332) causes clamp arm (344) to translate nearly or mostly vertically upwardly away from ultrasonic blade (360). It should therefore be understood that proximal longitudinal translation of pivot tube (370) relative to outer sheath (332) causes counter-clockwise rotation of pivot arm assembly (380) about pins (337) of outer sheath (332), which in turn causes clamp arm (344) to translate nearly or mostly vertically downwardly toward ultrasonic blade (360); and distal longitudinal translation of pivot tube (370) relative to outer sheath (332) causes clockwise rotation of pivot arm assembly (380) about pins (337) of outer sheath (332), which in turn causes clamp arm (344) to translate nearly or mostly vertically upwardly away from ultrasonic blade (360). Again, the movement of clamp arm (344) is not exactly vertical because clamp arm (344) is actually pivoting about pins (337), though the motion may appear to be vertical because pins (337) are spaced so far proximal of clamp arm (344).

Figure 21:
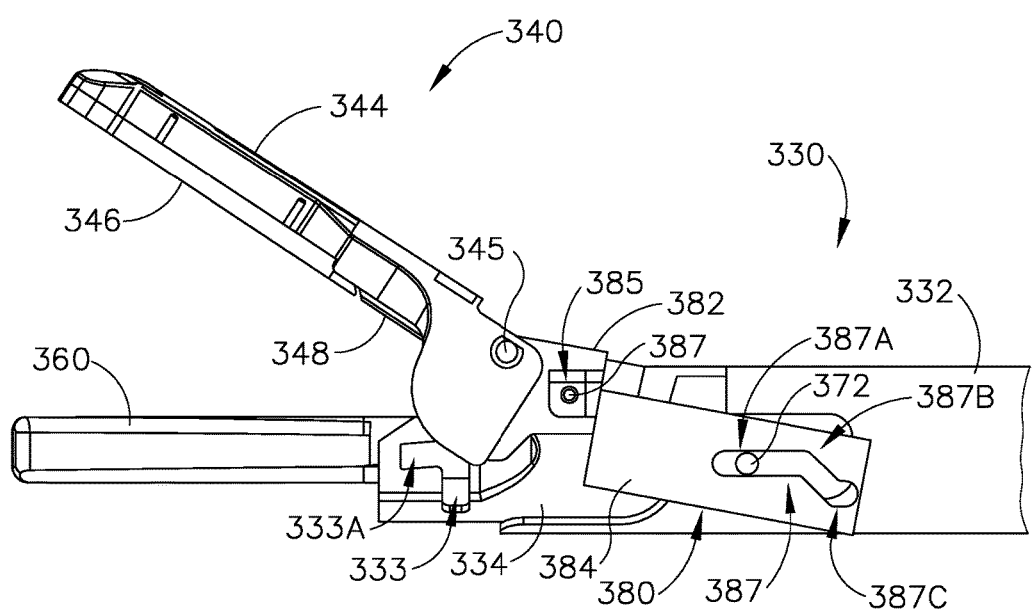
FIG. 21 depicts a detailed side elevational view of another exemplary alternative shaft assembly and end effector operable for use with the instrument of FIG. 6.

As shown in FIG. 21, shaft assembly (330) and end effector (340) may be reconfigured such that pivot arm assembly (380) is coupled directly with inner tube (334), and such that pivot tube (370) is omitted altogether. Inner tube (334) of the present example comprises a pair of pins (372) extending from an exterior surface of inner tube (334). Pins (372) are pivotably received within slots (387) of elongate-plate members (384) such that pivot arm assembly (380) is pivotably and slidably coupled with inner tube (334). As with pivot tube (370) discussed above, inner tube (334) is operable to translate longitudinally about within sheath (332) relative to outer sheath (332) so as to cause translation of pins (372) within slots (387) to thereby selectively rotate pivot arm assembly (380) about pins (337) of outer sheath (332). In particular, proximal longitudinal translation of inner tube (334) relative to outer sheath (332) causes counter-clockwise rotation of pivot arm assembly (380); and distal longitudinal translation of inner tube (334) relative to outer sheath (332) causes clockwise rotation of pivot arm assembly (380). Thus, it should be that inner tube (334) is operable to translate longitudinally within outer sheath (332) relative to outer sheath (332) to selectively pivot clamp arm (344) toward and away from blade (360) and nearly or mostly vertically translate clamp arm (344) toward and away from blade (360). In particular, inner tube (334) is operable to translate longitudinal within outer sheath (332) through a first range of longitudinal motion to pivot clamp arm (344) toward and away from blade (360); and then through a second range of longitudinal motion to nearly or mostly vertically translate clamp arm (344) toward and away from blade (360).

As shown in FIG. 21, slot (333) of inner tube (334) of the present example comprises a distal portion (333A). Distal portion (333A) is angled slightly obliquely relative to inner tube (334). As inner tube (334) translates longitudinally proximally through the first range of motion, clamp arm (344) pivots toward blade (360) and pins (372) translate within distal portion (387A) of slots (387). As inner tube (334) is further translated longitudinally proximally through the second range of longitudinal motion, clamp arm (344) translates nearly or mostly vertically downwardly within slot (333) into distal portion (333A) toward blade (360) as pins (372) translate within intermediate portion (387B) of slots (387) to thereby cause counter-clockwise rotation of pivot arm (360). As clamp arm (344) translates nearly or mostly vertically downwardly within slot (333) into distal portion (333A), distal portion (333A) permits proximal longitudinal translation of inner tube (334) without causing further rotation of clamp arm (344).

It should be understood from the foregoing that, regardless of whether instrument (200) incorporates shaft assembly (230) and end effector (240) of FIGS. 6-19C, shaft assembly (330) and end effector (340) of FIG. 20, or shaft assembly (330) and end effector (340) of FIG. 21, instrument (200) may operate in a "seal-only" mode when trigger (228) is pivoted toward grip (224) through a first range of motion; and then in a "cut-and-seal" mode when trigger (228) is further pivoted toward grip (224) through a second range of motion. Thus, instrument (200) is either in the "seal-only" mode or the "cut-and-seal" mode based on the particular pivotal position of trigger (228) relative to grip (224). In some versions, instrument (200) transitions from the "seal-only" mode to the "cut-and-seal" mode in a substantially seamless fashion, such that the user may freely and uninterruptedly continue pivoting trigger (228) toward grip (224) through the second range of motion after completing the first range of motion. In some other versions, instrument (200) may include one or more detents and/or other features that are operable to provide tactile, audible, and/or visual feedback to indicate a transition from the first range of motion to the second range of motion (which would further indicate a transition from the "seal-only" mode to the "cut-and-seal" mode).

In addition or in the alternative, instrument (200) may include a lockout feature that requires further operator input in order to enable trigger (228) to move through the second range of motion after completing the first range of motion. By way of example only, instrument (200) may effectively block further pivotal movement of trigger (228) at the end of the first range of motion; and may require the operator to press an additional trigger or button, etc. in order to unlock trigger (228) to thereby enable trigger (228) to move through the second range of motion. In some versions, handle assembly (220) includes a toggle button that is operable to transition instrument (200) between two states. In some such versions, trigger (228) is only able to pivot through the first range of motion in the first state. Upon reaching the end of the first range of motion, trigger (228) may be blocked from pivoting further. If the operator actuates the toggle button, the block is removed, such that trigger (228) may move freely through both the first range of motion and the second range of motion. Other suitable ways in which instrument (200) may provide a transition from the "seal-only" mode to the "cut-and-seal" mode will be apparent to those of ordinary skill in the art in view of the teachings herein.

C. Exemplary Ultrasonic Surgical Instrument with Translatable Sled

Figure 22:
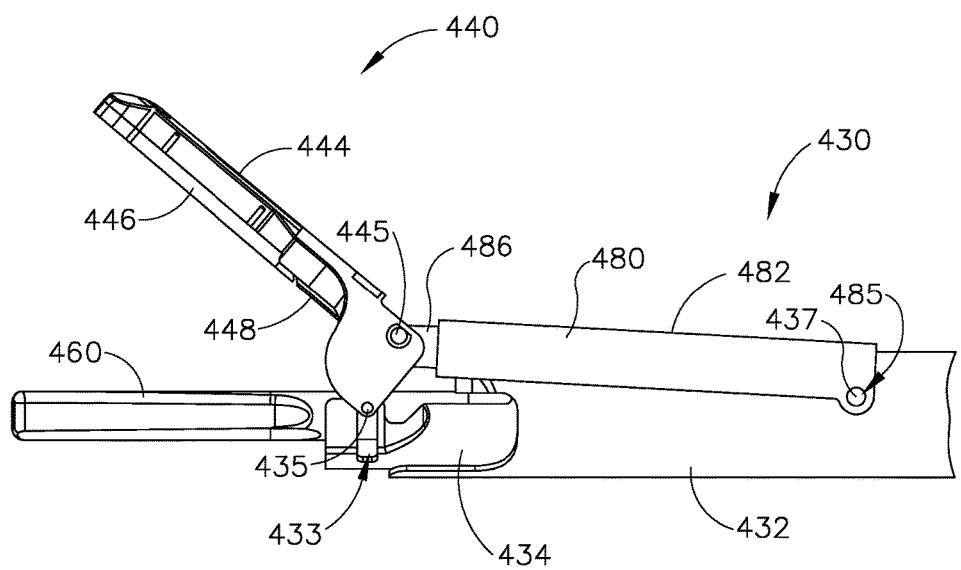
FIG. 22 depicts a detailed side elevational view of yet another exemplary alternative shaft assembly and end effector operable for use with the instrument of FIG. 6.
Figure 23A:
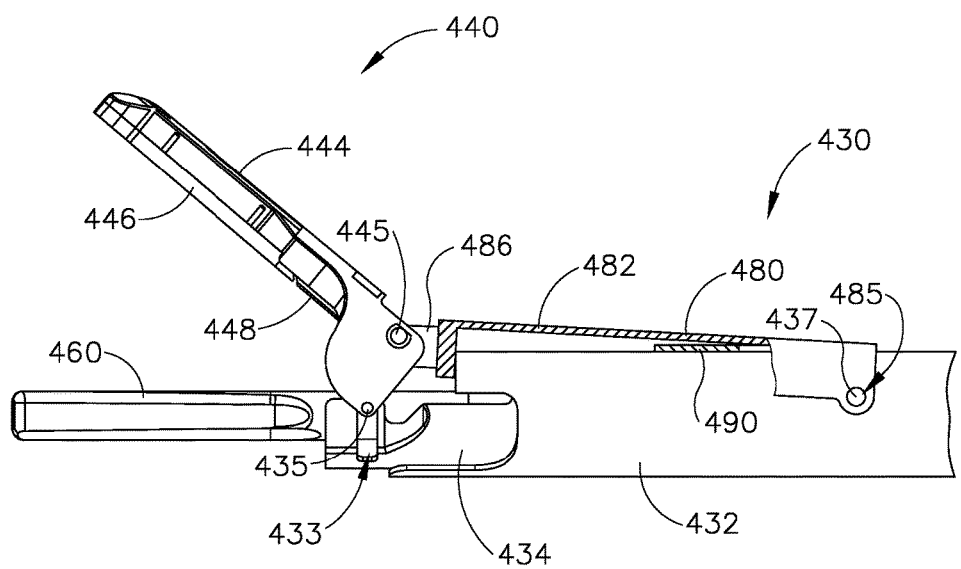
FIG. 23A depicts a detailed side elevational view of the shaft assembly and end effector of FIG. 22, with a portion of a pivot arm omitted to show a sled, with the sled of the shaft assembly in a first longitudinal position, and with a clamp arm of the end effector in a first vertical position.
Figure 23B:
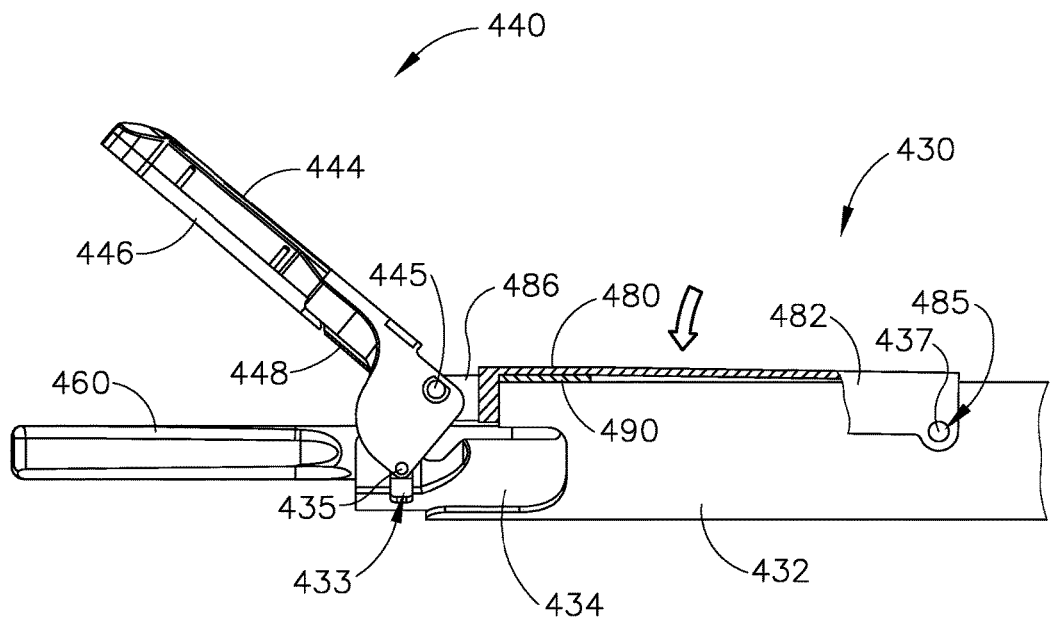
FIG. 23B depicts a detailed side elevational view of the shaft assembly and end effector of FIG. 22, with a portion of a pivot arm omitted to show a sled, with the clamp arm of FIG. 23A moved to a second vertical position by movement of the sled of FIG. 23A to a second longitudinal position.

FIGS. 22-23B depict an exemplary alternative shaft assembly (430) and end effector (440) that may be readily incorporated into instrument (200) in place of shaft assembly (230) and end effector (240). Shaft assembly (430) and end effector (440) are configured to operate substantially similar to shaft assemblies (230, 330) and end effectors (240, 340) discussed above except for the differences discussed below. In particular, shaft assembly (430) and end effector (440) are configured to selectively clamp tissue between a clamp arm (444) and an ultrasonic blade (460) of end effector (440) in a "seal-only" operation, in which blade (460) is operable to seal or weld tissue without cutting the tissue; and in a "cut-and-seal" operation, in which blade (460) is operable to cut tissue and seal or weld tissue substantially simultaneously.

Shaft assembly (430) of the present example comprises an outer sheath (432), an inner tube (434), a pivot arm (480), and a translatable sled (490). Inner tube (434) is slidably disposed within outer sheath (432). As with shaft assemblies (230, 330) discussed above, inner tube (434) is operable to translate longitudinally within outer sheath (432) relative to outer sheath (432) to selectively pivot clamp arm (444) toward and away from blade (460) about a pin (445). Pivot arm (480) is pivotably coupled with outer sheath (432) via pin (437). As with pivot arms (280, 380) discussed above, pivot arm (480) is operable to selectively rotate about pin (437) relative to outer sheath (432) to thereby translate clamp arm (444) vertically toward and away from blade (460). It should therefore be understood that, as with shaft assemblies (230, 330) and end effectors (240, 340) discussed above, a combination of rotation and nearly or mostly vertical translation of clamp arm (444) relative to blade (460) provides both a "seal-only" mode of operation and a "cut-and-seal" mode of operation.

End effector (440) of the present example comprises clamp arm (444) and ultrasonic blade (460). Clamp arm (444) includes a primary clamp pad (446) and a secondary clamp pad (448) that are secured to an underside of clamp arm (444), facing blade (460). Clamp arm (444) is operable to selectively pivot toward and away from blade (460) to selectively clamp tissue between clamp pads (446, 448) and blade (460). As will be discussed in more detail below, clamp arm (444) is pivotably coupled with a distal end of pivot arm (480) via pin (445) such that clamp arm (444) is operable to rotate about the distal end of pivot arm (480) via pin (445). A distal end of inner tube (434) is rotatably and slidably coupled with a proximal end of clamp arm (444) via pins (435), which are disposed within respective slots (433) at the distal end of inner tube (434) such that longitudinal translation of inner tube (434) causes rotation of clamp arm (444) about the distal end of pivot arm (480) toward and away from ultrasonic blade (460) to thereby clamp tissue between clamp pads (446, 448) and ultrasonic blade (460) to cut and/or seal the tissue. In particular, proximal longitudinal translation of inner tube (434) relative to outer sheath (432) and handle assembly (420) causes clamp arm (444) to rotate about pin (445) at the distal end of pivot arm (480) toward ultrasonic blade (460); and distal longitudinal translation of inner tube (434) relative to outer sheath (432) and handle assembly (420) causes clamp arm (444) to rotate about pin (445) at the distal end of pivot arm (480) away from ultrasonic blade (460).

As mentioned above, the distal end of inner tube (434) is slidably coupled with the proximal end of clamp arm (444) via pins (435) disposed within slots (433) such that clamp arm (444) is operable to rotate between an upward position and a downward position. As will be discussed in more detail below, rotation of pivot arm (480) causes nearly or mostly vertical translation of pins (435) relative to slots (433) to thereby clamp tissue between clamp pads (446, 448) and ultrasonic blade (460) to cut and/or seal the tissue. In particular, counter-clockwise rotation of pivot arm (480) about outer sheath (432) causes clamp arm (444) to translate nearly or mostly vertically downwardly toward ultrasonic blade (460) as pins (435) travel downwardly in slots (433); and clockwise rotation of pivot arm (480) about outer sheath (432) causes clamp arm (444) to translate nearly or mostly vertically upwardly away from ultrasonic blade (460) as pins (435) travel upwardly in slots (433).

Pivot arm (480) of the present example comprises a semi-cylindrical member (482). Semi-cylindrical member (482) has a hollow interior formed therein such that at least a portion of outer sheath (432) may be received within semi-cylindrical member (482). Pivot arm (480) also includes a pair of pinholes (485) formed in a proximal portion of semi-cylindrical member (482). Outer sheath (432) comprises a pair of pins (437) extending transversely from an exterior surface of outer sheath (432). Pins (437) are pivotably received within pinholes (485) of semi-cylindrical member (482) such that pivot arm (480) is pivotably coupled with outer sheath (432) and such that pivot arm (480) is operable to rotate about pins (437) of outer sheath (432). Pivot arm (480) is coupled with outer sheath (432) such that semi-cylindrical member (482) is positioned adjacent to a top surface of outer sheath (432).

As shown in FIGS. 23A and 23B, a translatable sled (490) is disposed within the hollow interior of semi-cylindrical member (482) between an interior surface of semi-cylindrical member (482) and an exterior top surface of outer sheath (432). Sled (490) is configured to translate longitudinally within the hollow interior of semi-cylindrical member (482) between a proximal longitudinal position (FIG. 23A) and a distal longitudinal position (FIG. 23B). As will be discussed in more detail below, longitudinal translation of sled (490) causes rotation of pivot arm (480) about pins (437) of outer sheath (432). In particular, distal longitudinal translation of a pivot tube (not shown) relative to outer sheath (432) causes counter-clockwise rotation of pivot arm (480) about pins (437) of outer sheath (432); and proximal longitudinal translation of the pivot tube relative to outer sheath (432) and handle assembly (420) causes clockwise rotation of pivot arm (480) about pins (437) of outer sheath (432). It should be understood that pivot arm (480) may be rotatably biased counter-clockwise to the position shown in FIG. 23B. By way of example only, such a bias may be provided by a coil spring and/or leaf spring interposed between an interior surface of semi-cylindrical member (482) and an exterior top surface of outer sheath (432), by one or more torsion springs positioned about pins (437), and/or by one or more other features. Various suitable ways in which pivot arm (480) may be rotatably biased counter-clockwise to the position shown in FIG. 23B will be apparent to those of ordinary skill in the art in view of the teachings herein.

Pivot arm (480) further comprises a projection (486) extending distally from a distal end of semi-cylindrical member (482). Clamp arm (444) is pivotably coupled with projection (486) of pivot arm (480) via pin (445) such that, as discussed above, rotation of pivot arm (480) about pins (437) of outer sheath (432) causes nearly or mostly vertical translation of pins (435) within slots (433), thereby causing nearly or mostly vertical translation of clamp arm (444) relative to ultrasonic blade (460). In particular, counter-clockwise rotation of pivot arm (480) about pins (437) of outer sheath (432) causes clamp arm (444) to translate nearly or mostly vertically downwardly toward ultrasonic blade (460); and clockwise rotation of pivot arm (480) about pins (437) of outer sheath (432) causes clamp arm (444) to translate nearly or mostly vertically upwardly away from ultrasonic blade (460). It should therefore be understood that distal longitudinal translation of sled (490) relative to outer sheath (432) and handle assembly (420) is causes counterclockwise rotation of pivot arm (480) about pins (437) of outer sheath (432), which in turn causes clamp arm (444) to translate nearly or mostly vertically downwardly toward ultrasonic blade (460); and proximal longitudinal translation of sled (490) relative to outer sheath (432) and handle assembly (420) causes clockwise rotation of pivot arm (480) about pins (437) of outer sheath (432), which in turn causes clamp arm (444) to translate nearly or mostly vertically upwardly away from ultrasonic blade (460).

In some versions, sled (490) is coupled with trigger (228) such that pivotal movement of trigger (228) causes longitudinal movement of sled (490). For instance, in some such versions, trigger (228) may move through a first range of motion to retract inner tube (434) proximally, thereby pivoting clamp arm (444) toward ultrasonic blade (460). Sled (490) may remain stationary during this first range of motion of trigger (228). As trigger (228) is moved through a second range of motion, inner tube (434) may remain stationary and sled (490) may be driven proximally, such that pivot arm (480) drives clamp arm (444) downwardly along a nearly or mostly vertical linear path toward ultrasonic blade (460). Thus, an instrument (200) with shaft assembly (430) and end effector (440) may be either in the "seal-only" mode or the "cut-and-seal" mode based on the particular pivotal position of trigger (228) relative to grip (224). Such an instrument may transition between such modes in the same manner as described above with respect to instrument (200) incorporating shaft assembly (230) and end effector (240) of FIGS. 6-19C, shaft assembly (330) and end effector (340) of FIG. 20, or shaft assembly (330) and end effector (340) of FIG. 21.

As yet another merely illustrative alternative, some versions may provide only pivotal movement of clamp arm (444) about pin (445) in response to pivotal movement of trigger (228) relative to pistol grip (224). In some such versions, a separate actuator (e.g., slider, pivoting trigger, button, etc.) may be provided to selectively drive sled (490) between the proximal position (FIG. 23A) and the distal position (FIG. 23B). Various suitable features that may be used to selectively drive sled (490) will be apparent to those of ordinary skill in the art in view of the teachings herein. Similarly, various suitable ways in which an instrument (200) that incorporates shaft assembly (430) and end effector (440) may provide a transition from the "seal-only" mode to the "cut-and-seal" mode will be apparent to those of ordinary skill in the art in view of the teachings herein.

D. Exemplary Ultrasonic Surgical Instrument with Four-Bar Linkage

Figure 24A:
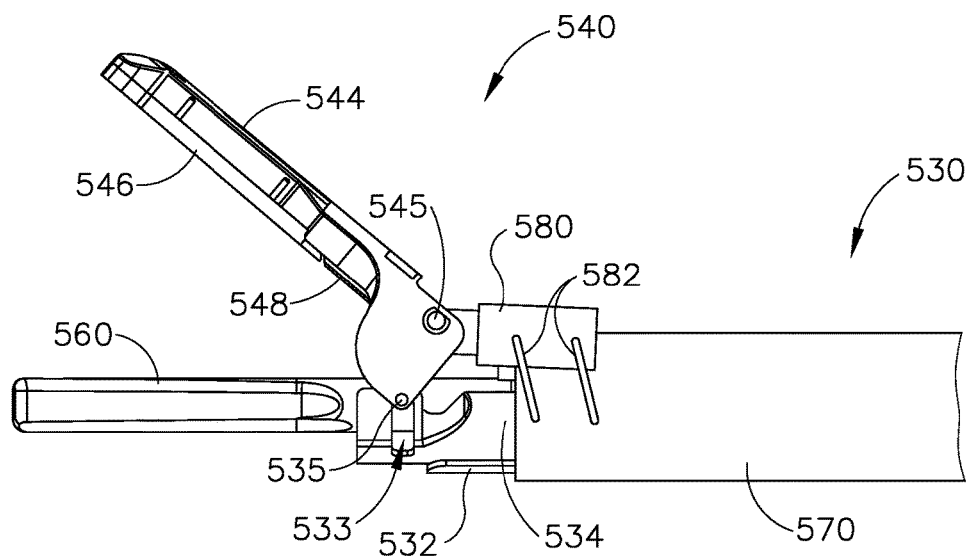
FIG. 24A depicts a side elevational view of yet another exemplary shaft assembly and end effector operable for use with the instrument of FIG. 6 with a pivot tube of the shaft assembly in a first longitudinal position, with a four-bar linkage in a first position, with an inner tube of the shaft assembly in a first longitudinal position, and with a clamp arm of the end effector in a first vertical position and a first rotational position.
Figure 24B:
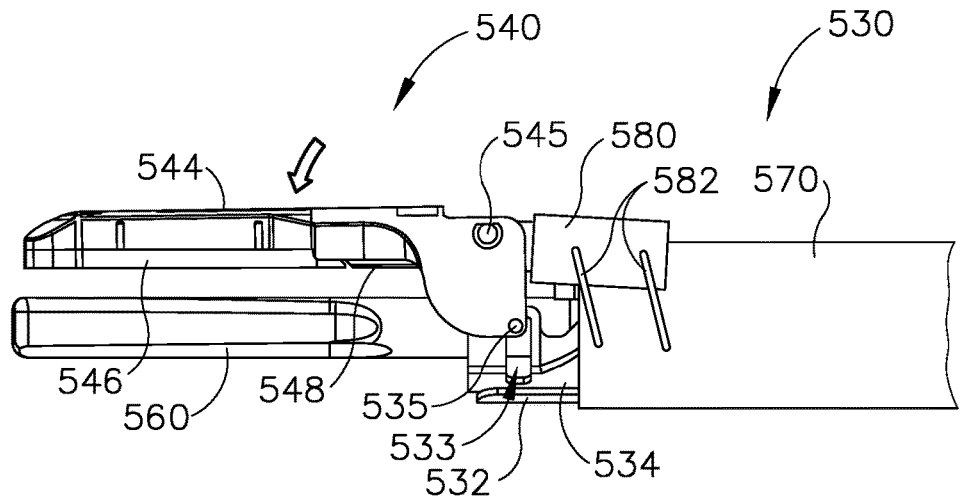
FIG. 24B depicts a side elevational view of the shaft assembly and end effector of FIG. 24A with the clamp arm of FIG. 24A moved to a second rotational position by movement of the inner tube of FIG. 24A to a second longitudinal position.
Figure 24C:
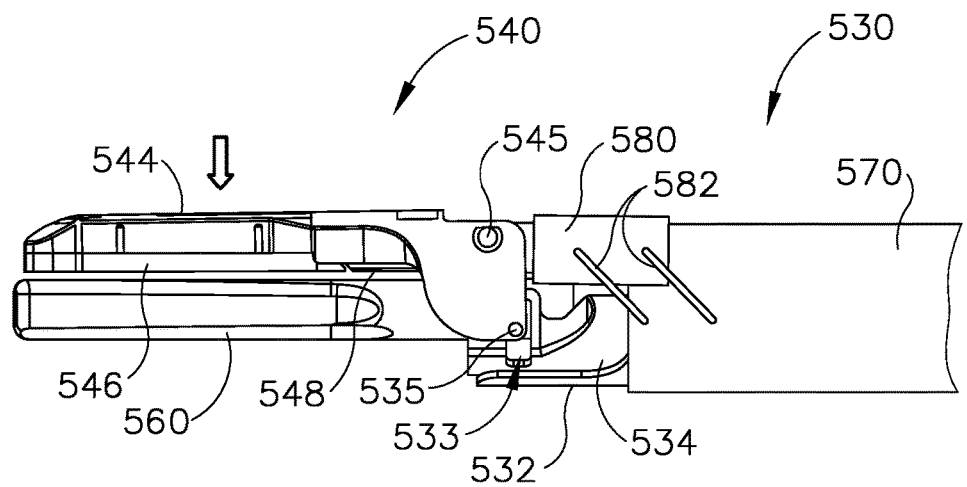
FIG. 24C depicts a side elevational view of the shaft assembly and end effector of FIG. 24A with the clamp arm of FIG. 24A moved to a second vertical position by movement of four-bar linkage to a second position by movement of the pivot tube of FIG. 24A to a second longitudinal position.

FIGS. 24A-24C depict another exemplary alternative shaft assembly (530) and end effector (540) that may be readily incorporated into instrument (200) in place of shaft assembly (230) and end effector (240). Shaft assembly (530) and end effector (540) are configured to operate substantially similar to shaft assemblies (230, 330, 430) and end effectors (240, 340, 440) discussed above except for the differences discussed below. In particular, shaft assembly (530) and end effector (540) are configured to selectively clamp tissue between a clamp arm (544) and an ultrasonic blade (560) of end effector (540) in a "seal-only" operation, in which blade (560) is operable to seal or weld tissue without cutting the tissue; and a "cut-and-seal" operation, in which blade (560) is operable to cut tissue and seal or weld tissue substantially simultaneously.

Shaft assembly (530) of the present example comprises an outer sheath (532), an inner tube (534), a pivot tube (570), and a pivot arm (580). Inner tube (534) is slidably disposed within outer sheath (532). As with shaft assemblies (230, 330, 430) discussed above, inner tube (534) is operable to translate longitudinally within outer sheath (532) relative to outer sheath (532) to selectively pivot clamp arm (544) toward and away from blade (560). Pivot tube (570) is slidably disposed about outer sheath (532) such that pivot tube (570) is operable to translate longitudinally about outer sheath (532) relative to outer sheath (532). Pivot arm (580) is pivotably coupled with pivot tube (570) via a four-bar linkage (582). While only two bars are shown in four-bar linkage (582), it should be understood that an identical pair of bars would be positioned on the opposite side of pivot tube (570) and pivot arm (580). As with pivot tube (270) discussed above, pivot tube (570) is operable to translate longitudinally about outer sheath (532) relative to outer sheath (532) to selectively rotate pivot arm (580) via four-bar linkage (582) to thereby translate clamp arm (544) vertically toward and away from blade (560) via pins (535) that are disposed within respective slots (533) formed within a distal end of inner tube (534). It should there be understood that a combination of rotation and vertical translation of clamp arm (544) relative to blade (560) provides both a "seal-only" mode of operation and a "cut-and-seal" mode of operation.

End effector (540) of the present example comprises clamp arm (544) and ultrasonic blade (560). Clamp arm (544) includes a primary clamp pad (546) and a secondary clamp pad (548) that are secured to an underside of clamp arm (544), facing blade (560). Clamp arm (544) is operable to selectively pivot toward and away from blade (560) about a pin (545) to selectively clamp tissue between clamp pads (546, 548) and blade (560). As will be discussed in more detail below, clamp arm (544) is pivotably coupled with a distal end of pivot arm (580) via pin (545) such that clamp arm (544) is operable to rotate about the distal end of pivot arm (580). A distal end of inner tube (534) is rotatably and slidably coupled with a proximal end of clamp arm (544) via pins (535) disposed within a respective slots (533) formed in a distal end of inner tube (534) such that longitudinal translation of inner tube (534) causes rotation of clamp arm (544) about the distal end of pivot arm (580) toward and away from ultrasonic blade (560) to thereby clamp tissue between clamp pads (546, 548) and ultrasonic blade (560) to cut and/or seal the tissue. In particular, proximal longitudinal translation of inner tube (534) relative to outer sheath (532) causes clamp arm (544) to rotate about pin (545) at the distal end of pivot arm (580) toward ultrasonic blade (560); and distal longitudinal translation of inner tube (534) relative to outer sheath (532) causes clamp arm (544) to rotate about pin (545) at the distal end of pivot arm (580) away from ultrasonic blade (560).

As mentioned above, the distal end of inner tube (534) is slidably coupled with the proximal end of clamp arm (544) via pins (535) disposed within slots (533) such that clamp arm (544) is operable to transition between an upward vertical and a downward position. As will be discussed in more detail below, rotation of pivot arm (580) causes vertical translation of pins (535) relative to slots (533), thereby causing clamp arm (544) to clamp tissue between clamp pads (546, 348) and ultrasonic blade (560) to cut and/or seal the tissue. In particular, counter-clockwise rotation of pivot arm (580) about outer sheath (532) causes clamp arm (544) to translate vertically downwardly toward ultrasonic blade (560); and clockwise rotation of pivot arm (580) about outer sheath (532) causes clamp arm (544) to translate vertically upwardly away from ultrasonic blade (560). As shown in FIGS. 24A-24C, as inner tube (534) is translated longitudinally proximally relative to outer sheath (532), clamp arm (544) is pivoted into the "seal-only" position as shown in FIG. 24B. As pivot tube (570) is translated longitudinally proximally relative to outer sheath (532), four-bar linkage (582) translates pivot arm (580) downwardly toward blade (560) at the distal end of shaft assembly (530) to thereby vertically translate clamp arm (544) toward blade (560) within slot (533) into the "cut-and-seal" position. Pivot arm (580) is constrained from moving longitudinally proximally or distally by one or more features (not shown) in outer sheath (532).

In some versions, pivot tube (570) is coupled with trigger (228) such that pivotal movement of trigger (228) causes longitudinal movement of pivot tube (570). For instance, in some such versions, trigger (228) may move through a first range of motion to retract inner tube (534) proximally, thereby pivoting clamp arm (544) toward ultrasonic blade (560). Pivot tube (570) may remain stationary during this first range of motion of trigger (228). As trigger (228) is moved through a second range of motion, inner tube (534) may remain stationary and pivot tube (570) may be driven proximally, such that pivot arm (580) drives clamp arm (544) downwardly along a vertical linear path toward ultrasonic blade (560). Thus, an instrument (200) with shaft assembly (530) and end effector (540) may be either in the "seal-only" mode or the "cut-and-seal" mode based on the particular pivotal position of trigger (228) relative to grip (224). Such an instrument may transition between such modes in the same manner as described above with respect to instrument (200) incorporating shaft assembly (230) and end effector (240) of FIGS. 6-19C, shaft assembly (330) and end effector (340) of FIG. 20, or shaft assembly (330) and end effector (340) of FIG. 21.

As yet another merely illustrative alternative, some versions may provide only pivotal movement of clamp arm (544) about pin (545) in response to pivotal movement of trigger (228) relative to pistol grip (224). In some such versions, a separate actuator (e.g., slider, pivoting trigger, button, etc.) may be provided to selectively drive pivot tube (570) between the distal position (FIGS. 24A-24B) and the proximal position (FIG. 24B). Various suitable features that may be used to selectively drive pivot tube (570) will be apparent to those of ordinary skill in the art in view of the teachings herein. Similarly, various suitable ways in which an instrument (200) that incorporates shaft assembly (530) and end effector (540) may provide a transition from the "seal-only" mode to the "cut-and-seal" mode will be apparent to those of ordinary skill in the art in view of the teachings herein.

E. Exemplary Handle Assembly with Additional Mode Selection Switch

Figure 25:
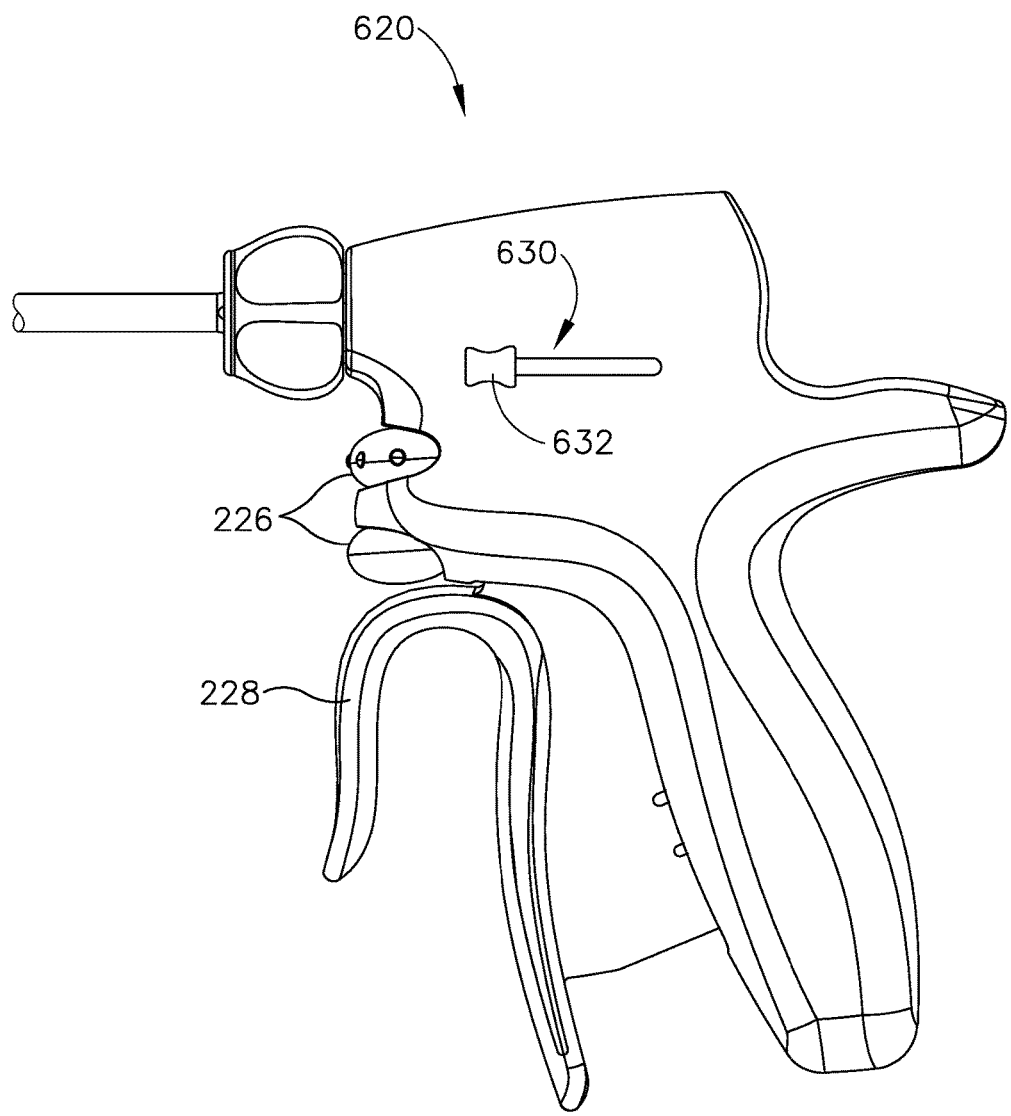
FIG. 25 depicts a side elevational view of an exemplary alternative handle assembly operable for use with the instrument of FIG. 6.

FIG. 25 depicts an exemplary alternative handle assembly (620) that may be readily incorporated into instrument (200) for use with any of the shaft assemblies (230, 330, 430, 530) and/or end effectors (240, 340, 440, 540) discussed above. Handle assembly (620) of this example is configured to operate substantially similar to handle assembly (220) discussed above except for the differences discussed below. Handle assembly (620) of the present example, however, comprises a switch assembly (630). Switch assembly (630) is configured to vertically or nearly vertically translate a clamp arm (not shown) between a "seal-only" operation and a "cut-and-seal" operation in addition to or in lieu of translation and rotation caused by trigger (228). Switch assembly (630) comprises a slider (632) that is longitudinally translatable between a proximal longitudinal position and a distal longitudinal position. Longitudinal translation of slider (632) between the proximal longitudinal position and the distal longitudinal position causes movement of the clamp arm between the "seal-only" operation and the "cut-and-seal" operation. For example, proximal longitudinal translation of slider (632) may move the clamp arm downwardly from the "seal-only" operation to the "cut-and-seal" operation; and distal longitudinal translation of switch assembly (630) may translate the clamp arm upwardly from the "cut-and-seal" operation to the "seal-only" operation. Various suitable components and features that may be used to provide translational and rotational movement of a clamp arm downwardly in response to longitudinal movement of slider (632) will be apparent to those of ordinary skill in the art in view of the teachings herein.

As one merely illustrative variation, switch assembly (630) may be configured such that slider (632) moves along a vertical path. For instance, switch assembly (630) may provide upward movement of the clamp arm away from the ultrasonic blade in response to upward movement of slider (632); and downward movement of the clamp arm away from the ultrasonic blade in response to downward movement of slider (632). Alternatively, switch assembly (630) may provide upward movement of the clamp arm away from the ultrasonic blade in response to downward movement of slider (632); and downward movement of the clamp arm away from the ultrasonic blade in response to upward movement of slider (632). As another merely illustrative example, handle assembly (620) may comprise a motor that is operable to transition the clamp arm between a "seal-only" operation and a "cut-and-seal" operation in addition to or in lieu of vertical translation caused by a trigger (228) and/or switch assembly (630). Such a motor may be actuated by, for example, one of buttons (226) or some other user input feature. Still other suitable features that may be provided to transition the clamp arm between a "seal-only" operation and a "cut-and-seal" operation will be apparent to those of ordinary skill in the art in view of the teachings herein.

As yet another merely illustrative example, handle assembly (620) may comprise a switch assembly (640) that is operable to selectively limit proximal longitudinal translation of an inner tube (634) as shown in FIGS. 26A-26D. Inner tube (634) is configured to operate substantially similar to inner tubes (134, 234, 334, 434, 534) described above except for the differences discussed below. In particular, inner tube (634) is operable to translate longitudinally within an outer sheath (632) relative to outer sheath (632) to selectively pivot a clamp arm (not shown) toward and away from an ultrasonic blade (not shown). In particular, proximal longitudinal translation of inner tube (634) relative to outer sheath (632) causes pivoting of the clamp arm toward the blade and distal longitudinal translation of inner tube (634) relative to outer sheath (632) causes pivoting of the clamp arm away from the blade. Thus, it should be appreciated that by limiting proximal longitudinal translation of inner tube (634), switch assembly (640) will limit pivoting of the clamp arm toward the blade.

Figure 26A:
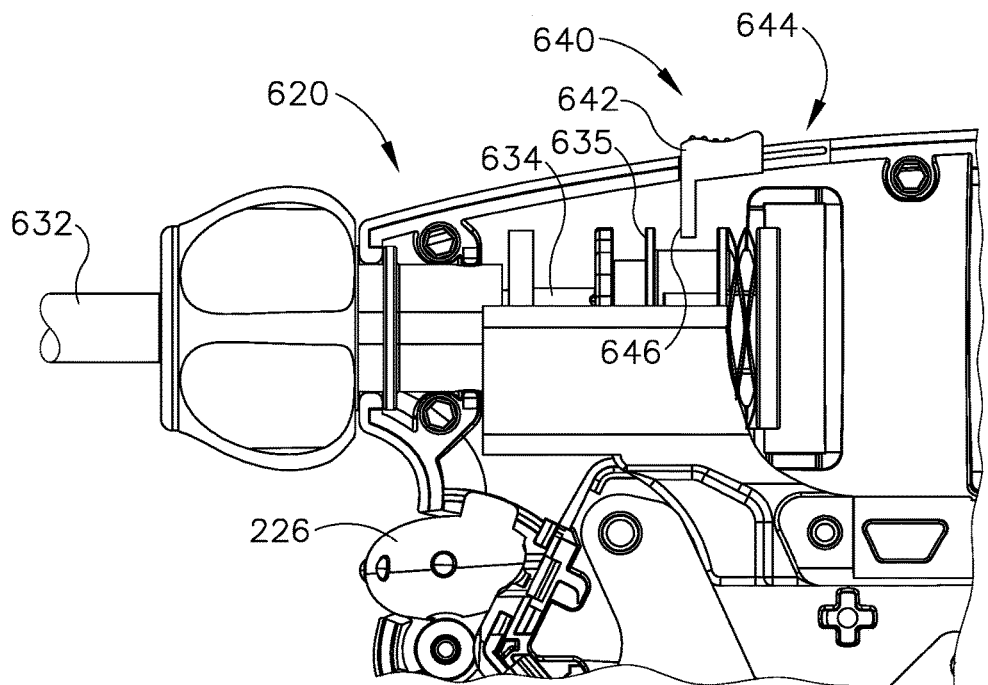
FIG. 26A depicts a side elevational view of the handle assembly of FIG. 25 with a housing shroud removed and having an exemplary switch assembly, with a switch of the switch assembly in a distal position, and with an inner tube of the handle assembly in a first longitudinal position.
Figure 26B:
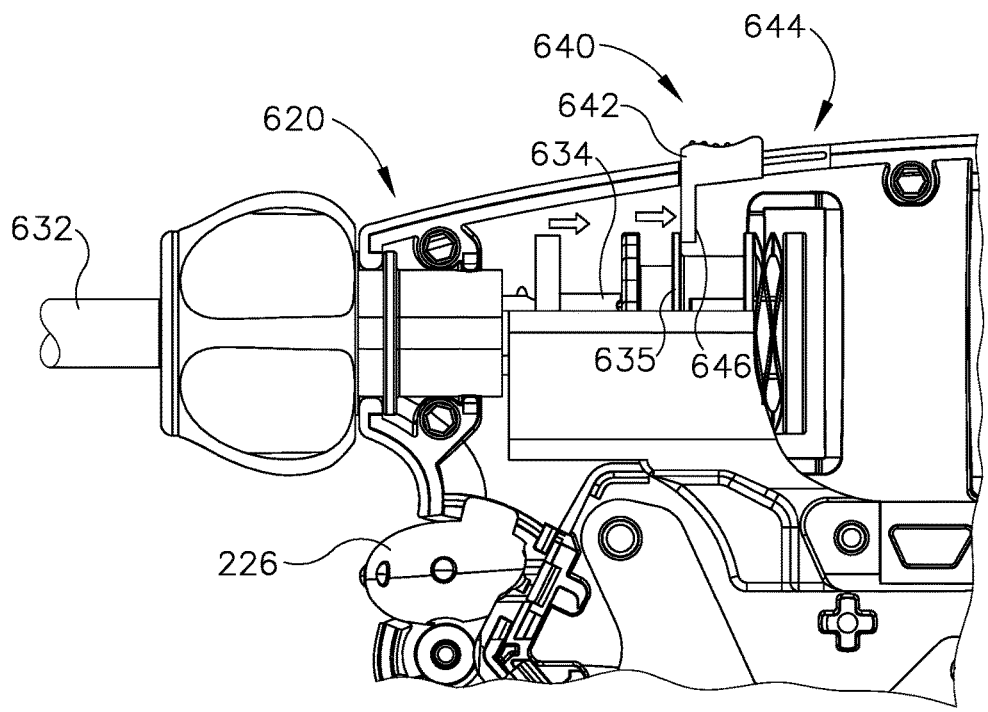
FIG. 26B depicts a side elevational view of the handle assembly of FIG. 25 with a housing shroud removed and having the switch assembly of FIG. 26A, with the switch of FIG. 26A in the distal position, and with the inner tube of FIG. 26A moved into a second longitudinal position into contact with the switch.
Figure 26C:
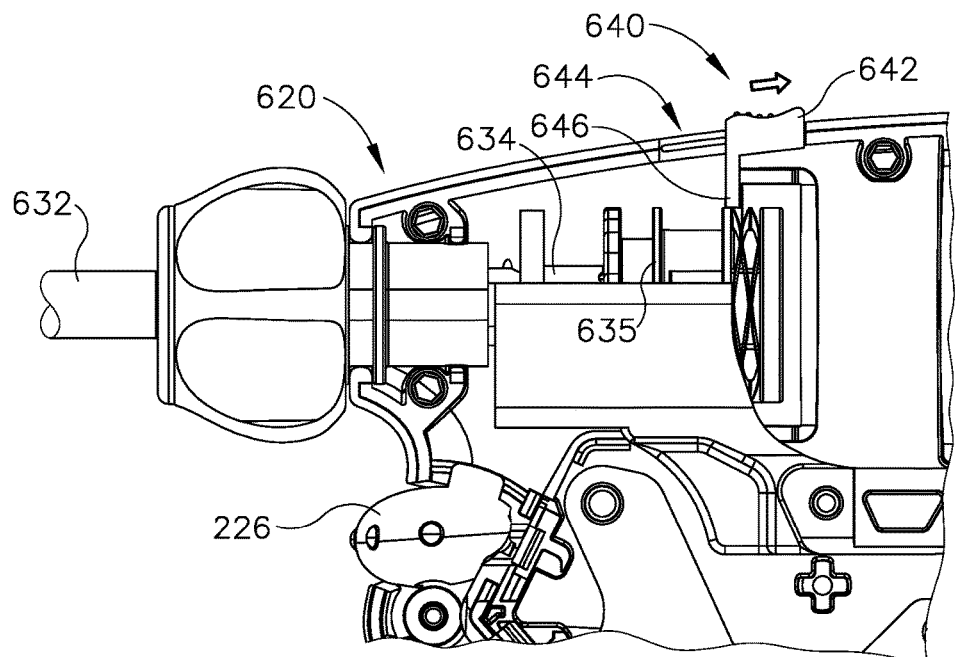
FIG. 26C depicts a side elevational view of the handle assembly of FIG. 25 with a housing shroud removed and having the switch assembly of FIG. 26A, with the switch of FIG. 26A moved into a proximal position, and with the inner tube of FIG. 26A in the second longitudinal position.
Figure 26D:
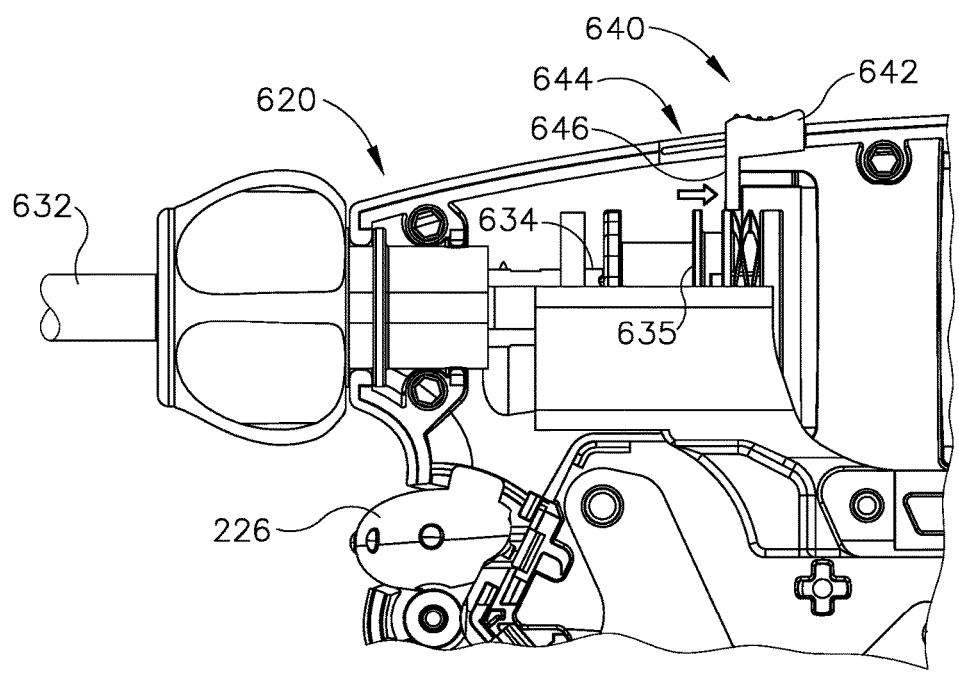
FIG. 26D depicts a side elevational view of the handle assembly of FIG. 25 with a housing shroud removed and having the switch assembly of FIG. 26A, with the switch of FIG. 26A in the proximal position, and with the inner tube of FIG. 26A moved into a third longitudinal position into contact with the switch.

FIGS. 26A-26D show the operation of switch assembly (640). Switch assembly (640) comprises a switch (642) that is slidably disposed within a slot (644) formed in a top surface of handle assembly (620). As will be described in more detail below, switch (642) is operable to slide within slot (644) between a distal position (FIGS. 26A and 26B) and a proximal position (FIGS. 26C and 26D). FIG. 26A shows switch (642) in the distal position within slot (644). As shown in FIG. 26B, as inner tube (634) is translated longitudinally proximally relative to outer sheath (632) so as to pivot the clamp arm toward the blade into a partially closed, or "seal-only," position, an integral flange (635) at the proximal end of inner tube (634) engages a distal arm (646) of switch (642) to thereby prevent further proximal longitudinal translation of inner tube (634). This prevents further pivoting of the clamp arm toward the blade. As shown in FIG. 26C, switch (642) may be slid proximally within slot (644) to the proximal position. With switch (642) in the proximal position, distal arm (646) is positioned to permit further proximal translation of flange (635). Inner tube (634) may thus be further translated longitudinally proximally relative to outer sheath (632) as shown in FIG. 26D so as to further pivot the clamp arm toward the blade into the completely closed, or "cut-and-seal," position. It should be appreciated that switch (642) may be slid within slot (644) into any desired position between the distal position and the proximal position so as to limit pivoting of the clamp arm to any desired position between the partially closed position and the completely closed position.

In some variations of the example shown in FIGS. 26A-26D, switch (642) is used in an instrument that has a pivot tube such as any of the various pivot tubes (270, 370, 470, 570) described herein. For instance, switch (642) may be positioned and configured such that distal arm (646) selectively engages an integral proximal flange (e.g., flange (274)) of pivot tube (270, 370, 470, 570) to thereby selectively restrict proximal movement of pivot tube (270, 370, 470, 570). When switch (642) is in a distal position, distal arm (646) may restrict proximal motion of pivot tube (270, 370, 470, 570) such that the instrument is only operable in a "seal-only" mode. When switch (642) is in a proximal position, distal arm (646) may prevent pivot tube (270, 370, 470, 570) to move fully proximally, thereby enabling operation in a "cut-and-seal" mode. Other suitable ways in which switch (642) may be incorporated into an instrument will be apparent to those of ordinary skill in the art in view of the teachings herein.

F. Exemplary Ultrasonic Surgical Instrument with Segmented Clamp Arm

FIGS. 27A-28B depict an exemplary alternative shaft assembly (730) and end effector (740) that may be readily incorporated into instrument (100, 200) in place of shaft assembly (130, 230) and end effector (140, 240). End effector (740) of this example includes a first clamp arm (742), a second clamp arm (746), and an ultrasonic blade (760). First clamp arm (742) has a first pair of legs (741). Legs (741) straddle a proximal end of ultrasonic blade (760), such that one leg (741) is positioned at one lateral side of ultrasonic blade (760) while the other leg (741) is positioned at the other lateral side of ultrasonic blade (760). Each leg (741) also has a sloped face (743). Second clamp arm (742) also has a second pair of legs (744). Legs (744) also straddle a proximal end of ultrasonic blade (760), such that one leg (744) is positioned at one lateral side of ultrasonic blade (760) while the other leg (744) is positioned at the other lateral side of ultrasonic blade (760). Clamp arm (746) is positioned laterally inwardly from clamp arm (742); and legs (744) are positioned laterally inwardly from legs (741). Ultrasonic blade (760) is substantially similar to ultrasonic blade (160, 260) mentioned above.

Figure 27B:
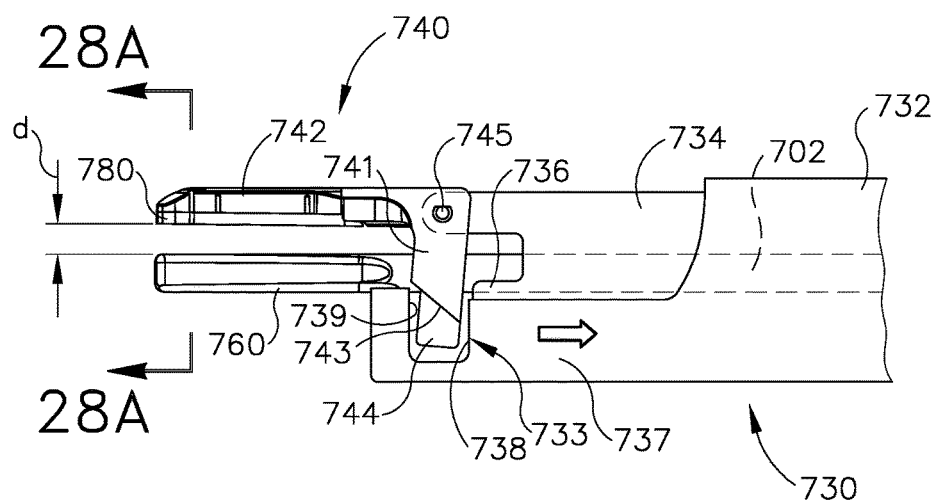
FIG. 27B depicts a side elevational view of the end effector and shaft assembly of FIG. 27A, with the end effector in a first closed position.
Figure 27C:
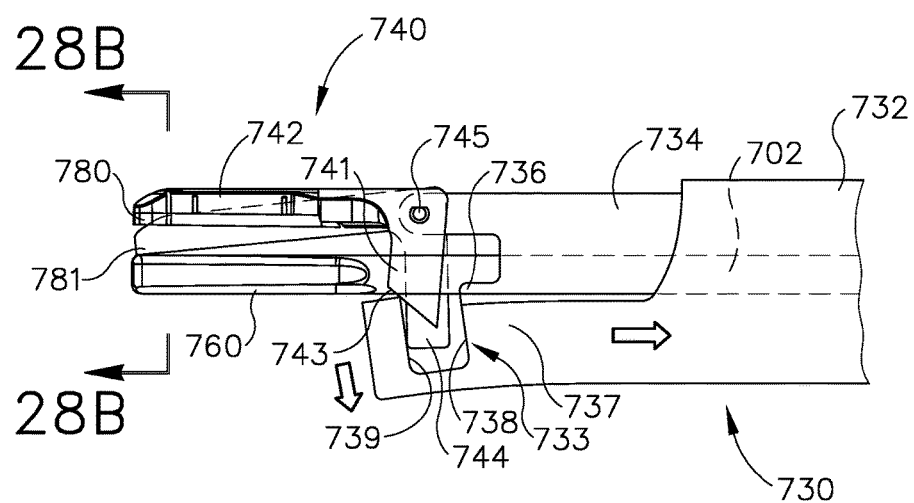
FIG. 27C depicts a side elevational view of the end effector and the shaft assembly of FIG. 27A, with the end effector in a second closed position.

Similar to clamp arm (144, 244), first clamp arm (742) and second clamp arm (746) each include a clamp pad (780, 781) facing toward ultrasonic blade (760). Additionally, first clamp arm (742) and second clamp arm (746) may are coupled with trigger (128) such that first clamp arm (742) and second clamp arm (746) are pivotable toward ultrasonic blade (760) in response to pivoting of trigger (128) toward pistol grip (124); and such that first clamp arm (742) and second clamp arm (746) are pivotable away from ultrasonic blade (760) in response to pivoting of trigger (128) away from pistol grip (124). As will be described in greater detail below, first clamp arm (742) and second clamp arm (744) are configured to pivot together toward blade (760) to a first closed position, defining a gap distance (d) as shown in FIGS. 27B and 28A. Additionally, second clamp arm (744) is configured to pivot further toward blade (760) to a second closed position while first clamp arm (742) remains in the first closed position, as shown in FIGS. 27C and 28B.

Shaft assembly (730) of the present example comprises an outer sheath (732) having a resilient distal end (737), an inner tube (734) having a distally projecting stop (736), and a waveguide (702) disposed within inner tube (734). Shaft assembly (730) is substantially similar to shaft assembly (130) described above, except for the differences discussed below. Therefore, waveguide (702) may communicate ultrasonic vibrations from transducer assembly (112) to ultrasonic blade (760).

While inner tube (134) is slidably disposed within outer sheath (132) of shaft assembly (130), outer sheath (732) of the current example is slidable relative to inner tube (734) of shaft assembly (730). Therefore, outer sheath (732) is operable to translate longitudinally relative to inner tube (734) to selectively pivot first clamp arm (742) and second clamp arm (746) while inner tube (734) remains stationary. Of course, inner tube (734) may alternatively be configured to translate longitudinally relative to outer sheath (732) to selectively pivot first clamp arm (742) and second clamp arm (746).

Figure 28B:
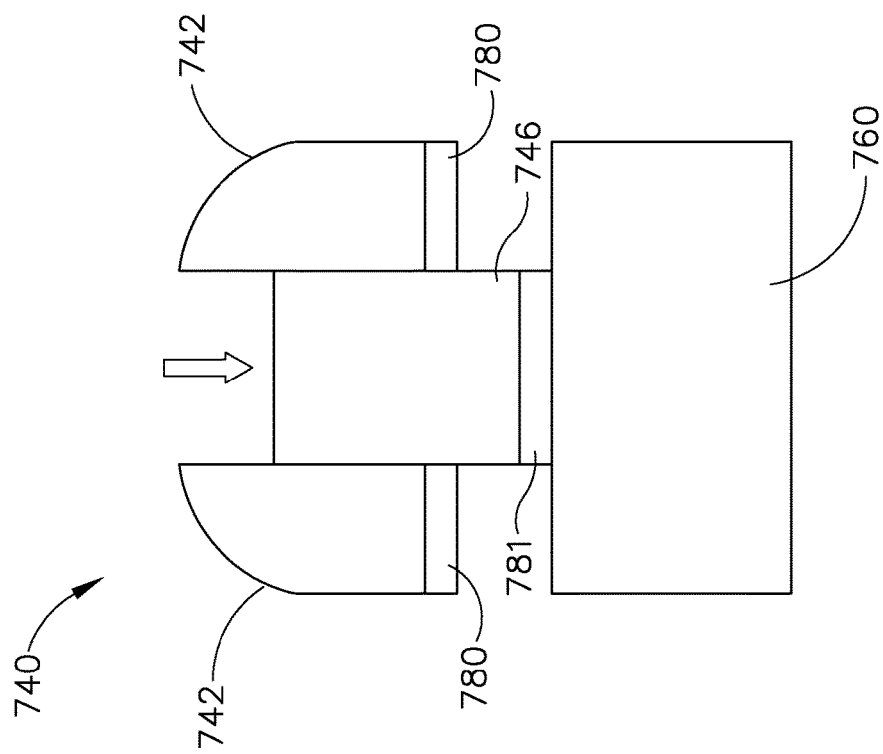
FIG. 28B depicts a cross-sectional front view of the end effector of FIG. 27A taken along line 28B-28B of FIG. 27C.
Figure 28A:
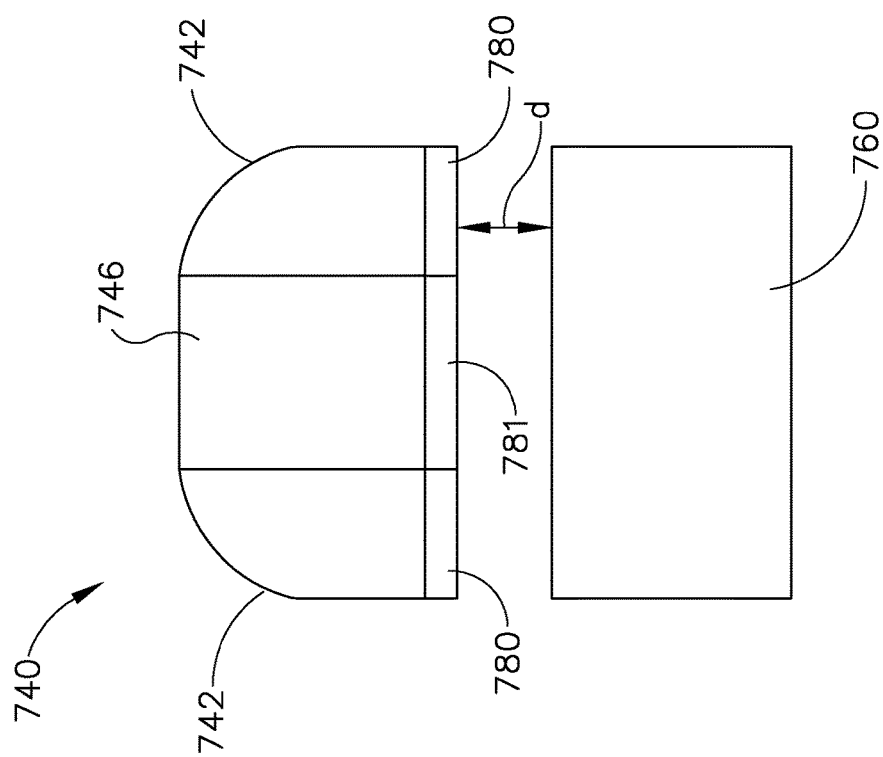
FIG. 28A depicts a cross-sectional front view of the end effector of FIG. 27A taken along line 28A-28A of FIG. 27B.

As shown in FIGS. 28A-28B, first clamp arm (742) is fork shaped to define a recess (747) that receives second clamp arm (746). Second clamp arm (746) is free to move along a vertical plane within recess (747). Both first clamp arm (742) and second clamp arm (746) are pivotally coupled to inner tube (734) via pin (745). While first clamp arm (742) is currently shown with a fork shape, it should be noted that this is merely optional, as first clamp arm (742) could be a single arm directly adjacent to second clamp arm (746). As another merely illustrative example, first clamp arm (742) may be U-shaped, with the bend of the "U" being distal to the distal end of second clamp arm (746). Other suitable configurations that may be used to form first clamp arm (742) will be apparent to one having ordinary skill in the art in view of the teachings herein.

Each first leg (741) and each second leg (744) extend from pin (745) toward and within a respective slot (733) defined by resilient distal end (737) of outer sheath (732). Each second leg (744) extends past sloped face (743) of the corresponding first leg (741). Slot (733) includes a proximal face (738) and a distal face (739). Distal translation of outer sheath (732) may cause proximal face (738) of slot (733) to contact first leg (741) and second leg (744) simultaneously, thereby rotating first clamp arm (742) and second clamp arm (746) away from ultrasonic blade (760).

As seen in FIGS. 27A-27B, proximal translation of outer sheath (732) may cause distal face (739) of slot (733) to contact first leg (741) and second leg (744), thereby rotating first clamp arm (742) and second clamp arm (746) simultaneously toward ultrasonic blade (760) to a first closed position shown in FIGS. 27B and 28A. With clamp arms (742, 746) positioned as shown in FIG. 27B and FIG. 28A, distal face (739) of slot (733) forces first leg (741) in contact with stop (736). Stop (736) is configured to prevent first leg (741) from further pivotal movement. Stop (736) is nevertheless dimensioned to not interfere with rotation of second leg (744). With clamp arms (742, 746) positioned as shown in FIG. 27B and FIG. 28A, second leg (744) is aligned with first leg (741), such that clamp pads (780, 781) are coplanar with each other, and such that both clamp pads (780, 781) are oriented parallel to ultrasonic blade (760). This positioning of clamp arms (742, 746) provides gap distance (d) between ultrasonic blade (760) and clamp pads (780, 781). By way of example only, gap distance (d) may be dimensioned around 0.010 inches. Alternatively, any other suitable gap distance (d) may be provided.

Gap distance (d), similar to gap (G) described above, is configured to minimize a clamping pressure applied to tissue captured between clamp arms (742, 746) and blade (760) such that blade (760) is operable to seal or weld the tissue, but not cut the tissue in this position. It should be appreciated that handle assembly (120), shaft assembly (730), and/or end effector (740) may include features that are configured to provide tactile and/or auditory feedback to the operator to signal that clamp arms (742, 746) have reached this "seal-only" position. By way of example only, such feedback features may comprise detents, etc. Additionally or alternatively, handle assembly (120) may include a lockout that holds trigger (128) at the pivotal position associated with gap distance (d) between achieved between ultrasonic blade (760) and clamp pads (780, 781). The associated lockout with trigger (128) may be removed by an additional user input or may be automatically controlled by several mechanisms or means, such as a retractable pin or solenoid selectively allowing further proximal movement of outer sheath (732).

As seen in FIG. 27C, outer sheath (732) may translate further in the proximal direction. During such proximal movement, distal face (739) of slot (733) may contact sloped face (743) of first leg (741). Because first leg (741) is prevented from further rotation due to contact with stop (736) of inner tube (734), resilient distal end (737) of outer sheath (732) deforms downwardly due to camming contact with sloped face (743) of first leg (741). Distal face (739) still remains in contact with second leg (744) of second clamp arm (746). Therefore, second clamp arm (746) is pivoted further toward ultrasonic blade (760) as shown in FIGS. 27C and 28B. At this position, second clamp arm (746) is configured to further compress tissue, increasing clamping pressure applied to tissue captured between clamp arm (746) and blade (760) such that blade (760) is operable to cut and seal tissue in this position. Thus, as outer sheath (732) translates proximally through a first range of motion (from the position shown in FIG. 27A to the position shown in FIG. 27B), end effector (740) transitions to a "seal only" mode of operation; and as outer sheath (732) translates proximally through a second range of motion (from the position shown in FIG. 27B to the position shown in FIG. 27C), end effector (740) transitions to a "seal and cut" mode of operation.

When the operator releases trigger (128), outer sheath (732) may translate distally. During such distal motion of outer sheath (732), resilient distal end (737) may return to its original shape, as shown in FIGS. 27A-27B, once distal face (739) is no longer in contact with sloped face (743) of first leg (741). Therefore, an operator may manipulate shaft assembly (730) multiple times between positions shown in FIGS. 27A-27C without affecting the structural integrity of shaft assembly (730). It should also be understood that proximal face (738) may bear against legs (741, 744) during distal motion of outer sheath (732), thereby driving clamp arms (742, 746) back to the open position.

G. Exemplary Ultrasonic Surgical Instrument with Slidable Clamp Arm Stop

Figure 29A:
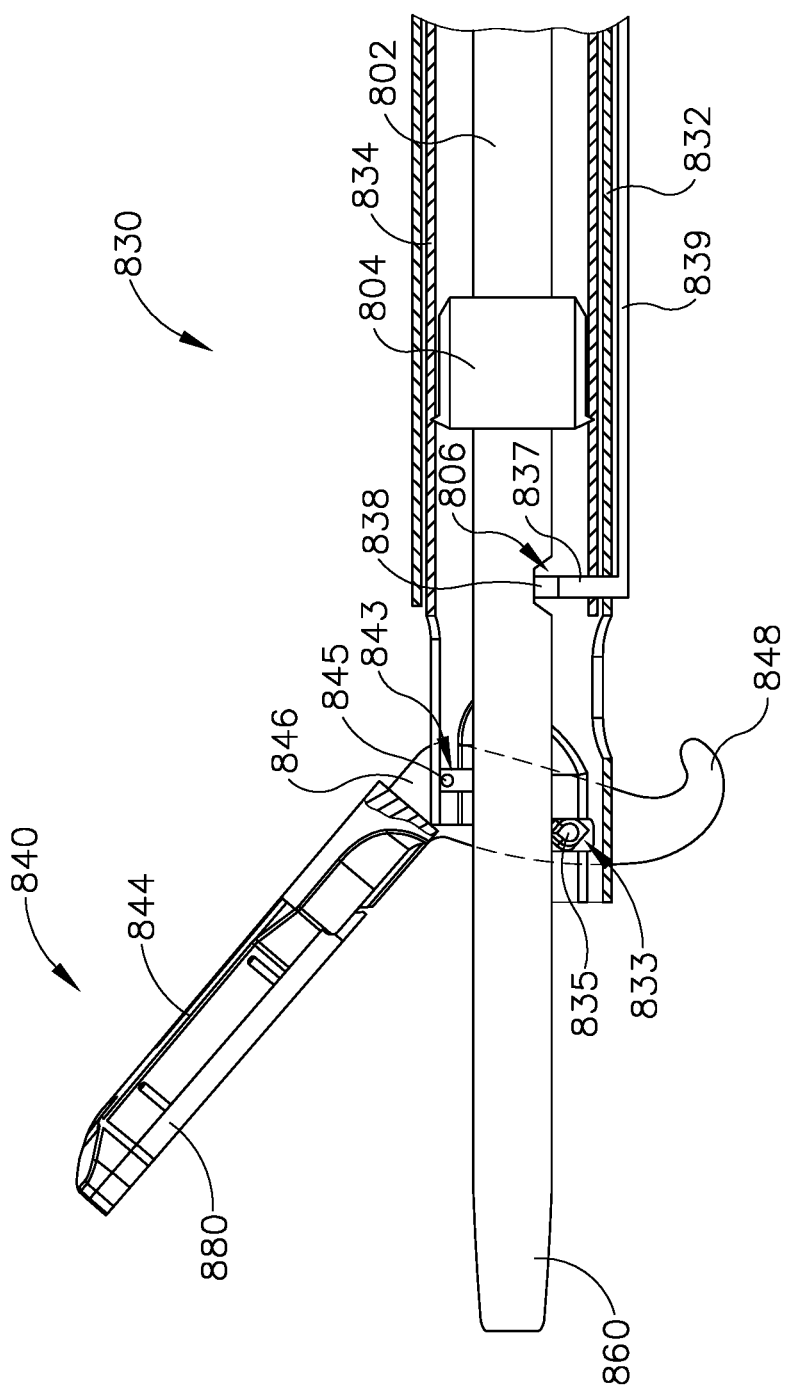
FIG. 29A depicts a cross-sectional side view of another exemplary alternative end effector and another exemplary alternative shaft assembly that may be incorporated in the instrument of FIG. 2, with the end effector in an open position.

FIGS. 29A-29C depict an exemplary alternative shaft assembly (830) and end effector (840) that may be readily incorporated into instrument (100, 200) in place of shaft assembly (130, 230) and end effector (140, 240). End effector (840) of this example includes a pivotable clamp arm (844) and an ultrasonic blade (860). Ultrasonic blade (860) is substantially similar to ultrasonic blade (160, 260) mentioned above. Similar to clamp arm (144, 244), clamp arm (844) includes a clamp pad (880) facing towards ultrasonic blade (860). Additionally, clamp arm (844) may be coupled with trigger (128) such that clamp arm (844) is pivotable toward ultrasonic blade (860) in response to pivoting of trigger (128) toward pistol grip (124); and such that clamp arm (844) is pivotable away from ultrasonic blade (860) in response to pivoting of trigger (128) away from pistol grip (124).

As will be described in greater detail below, clamp arm (844) is configured to pivot toward blade (860) to a first closed position, defining a gap distance (d) as shown in FIG. 29C. Additionally, clamp arm (844) is configured to pivot further toward blade (860) to a second closed position as shown in FIG. 29B.

Shaft assembly (830) includes an outer sheath (832), an inner tube (834) disposed within outer sheath (832), a waveguide (802) disposed within inner tube (834), a seal (804), and a moveable clamp arm stop (839) having a distal projection (837) with clamp pad material (838). Similar to shaft assembly (730), Outer sheath (832) of the current example is slidable relative to inner tube (834) of shaft assembly (830).

The distal end of inner tube (834) defines a slot (843). Clamp arm (844) further includes a leg (846) that is pivotally coupled to slot (843) of inner tube (834) via pin (845). Pin (845) is free to vertically translate within slot (843). A distal end of outer sheath (832) also defines a slot (833). Slot (833) of outer sheath (832) is rotatably coupled with leg (846) of clamp arm (844) below ultrasonic blade (860) via a pin (835) such that longitudinal translation of outer sheath (832) relative to inner tube (834) causes rotation of clamp arm (844) about pin (845) toward and away from ultrasonic blade (860) to thereby clamp tissue between clamp arm (844) and ultrasonic blade (860) to cut and/or seal the tissue. In particular, proximal longitudinal translation of outer sheath (832) relative to inner tube (834) and handle assembly (120) causes clamp arm (844) to move toward ultrasonic blade (860); and distal longitudinal translation of outer sheath (832) relative to inner tube (834) and handle assembly (120) causes clamp arm (844) to move away from ultrasonic blade (860).

Moveable clamp arm stop (839) is longitudinally slidable relative to outer sheath (832), inner tube (834), and waveguide (802). Distal projection (837) of moveable clamp arm stop (839) extends through outer sheath (832) and inner tube (834). As shown in FIGS. 29A-29B, clamp pad material (838) of moveable clamp arm stop (839) is configured to fit within a recess (806) defined by waveguide (802) when moveable clamp arm stop (839) is in a first position. Moveable clamp arm stop (839) may slide in the distal direction out of recess (806) to a second position as shown in FIG. 29C. When moveable clamp arm stop (839) slides out of recess (806), clamp pad material (838) makes contact with the outer diameter of waveguide (802). As will be described in greater detail below, moveable clamp arm stop (839) is configured to prevent clamp arm (844) from fully closing relative to blade (860).

FIG. 29A shows clamp arm (844) in an open position. When clamp arm (844) is in an open position, outer sheath (832) is in a distal position. Additionally, pin (845) is in a raised position within slot (843). When movable stop (839) is in the first position, as shown in FIG. 29B, proximal translation of outer sheath (832) relative to inner tube (834) rotates clamp arm (844) about pin (845) unobstructed so that clamp arm (844) is in a completely closed position. In other words, stop (839) does not interfere with pivotal movement of clamp arm (844) when stop (839) is in the first position. Since pin (845) is free to vertically translate within slot (843), rotation of clamp arm (844) forces pin (845) in the downward direction to the bottom of slot (843). Clamp pad (880) is thus positioned adjacent to blade (860) without a gap between clamp pad (880) and blade (860). At this position, clamp arm (844) is configured to grasp tissue with a clamping pressure applied to tissue captured between clamp arm (844) and blade (860) such that end effector (840) is operable to cut and seal tissue in this position.

As mentioned above, moveable clamp arm stop (839) may translate from a first longitudinal position, where clamp pad material (838) extends within recess (806), to a second longitudinal position, where clamp pad material (838) contacts the outer diameter of waveguide (802). FIG. 29C shows stop (839) in the second position. As shown in FIG. 29C, movable stop (839) is configured to limit the range of rotation of clamp arm (844) via contact between movable clamp arm stop (839) and nub (848) of clamp arm (844) when clamp arm stop (839) is in the second longitudinal position. Movable clamp arm stop (839) is positioned such that contact with nub (848) occurs when pin (845) is in between the top and bottom of slot (843). Because pin (845) in located between the top and bottom of slot (843), clamp arm (844) and blade (860) define gap distance (d).

Gap distance (d), similar to gap (G) described above, is configured to minimize a clamping pressure applied to tissue captured between clamp arm (844) and blade (860) such that blade (860) is operable to seal or weld the tissue, but not cut the tissue in this position. Therefore, depending on the location of moveable clamp arm stop (839), closing of clamp arm (844) may grasp tissue such that blade (860) is operable to only seal tissue or cut and seal tissue. It should be understood that any suitable user input feature may be used to drive stop (839) between the first and second positions. Various suitable features that may be used to drive stop (839) between the first and second positions will be apparent to those of ordinary skill in the art in view of the teachings herein.

H. Exemplary Ultrasonic Surgical Instrument with Rotatable Clamp Arm Stop

FIGS. 30A-31B depict another exemplary alternative shaft assembly (930) and end effector (940) that may be readily incorporated into instrument (100, 200) in place of shaft assembly (130, 230) and end effector (140, 240). End effector (940) of this example includes a pivotable clamp arm (944) and an ultrasonic blade (960). Ultrasonic blade (960) is substantially similar to ultrasonic blade (160, 260) mentioned above. Similar to clamp arm (144, 244), clamp arm (944) includes a clamp pad (980) facing toward ultrasonic blade (960). Additionally, clamp arm (944) may be coupled with trigger (128) such that clamp arm (944) is pivotable toward ultrasonic blade (960) in response to pivoting of trigger (128) toward pistol grip (124); and such that clamp arm (944) is pivotable away from ultrasonic blade (960) in response to pivoting of trigger (128) away from pistol grip (124).

As will be described in greater detail below, clamp arm (944) is configured to pivot toward blade (960) to a first closed position, defining a gap distance (d) as shown in FIG. 30C. Additionally, clamp arm (944) is configured to pivot further toward blade (960) to a second closed position as shown in FIG. 30B.

Shaft assembly (930) includes an outer sheath (892), an inner tube (934) disposed within outer sheath (932), a waveguide (902) disposed within inner tube (934), a seal (804), and a clamp arm stop (906) fixed to waveguide (902). In particular, clamp arm stop (906) is in the form of a projection extending laterally and unitarily from waveguide (902). Similar to shaft assembly (730, 830), outer sheath (932) of the current example is slidable relative to inner tube (934) of shaft assembly (930). Outer sheath (932) also includes a lateral opening (936) that is sized to receive a nub (948) of clamp arm (944) when clamp arm (944) rotates to a closed position.

The distal end of inner tube (934) defines a slot (943). A leg (946) of clamp arm (944) is pivotally coupled to slot (943) of inner tube (934) via pin (945). Pin (945) is free to vertically translate within slot (943). A distal end of outer sheath (932) defines a slot (933). Slot (933) of outer sheath (932) is rotatably coupled with leg (946) of clamp arm (944) below ultrasonic blade (960) via a pin (935) such that longitudinal translation of outer sheath (932) relative to inner tube (934) causes rotation of clamp arm (944) about pin (945) toward and away from ultrasonic blade (960) to thereby clamp tissue between clamp arm (944) and ultrasonic blade (960) to cut and/or seal the tissue. In particular, proximal longitudinal translation of outer sheath (932) relative to inner tube (934) and handle assembly (120) causes clamp arm (944) to move toward ultrasonic blade (960); and distal longitudinal translation of outer sheath (932) relative to inner tube (934) and handle assembly (120) causes clamp arm (944) to move away from ultrasonic blade (960).

Figure 30A:
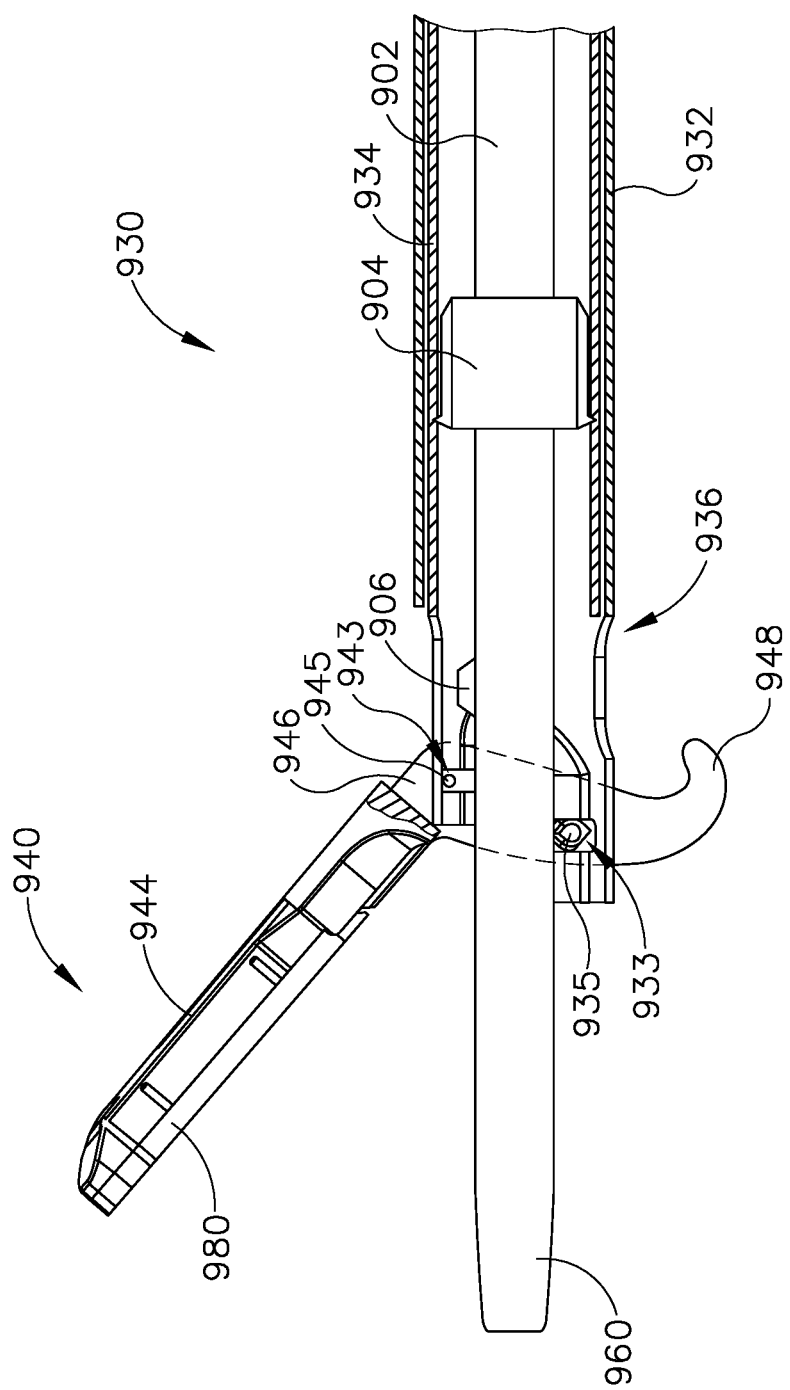
FIG. 30A depicts a cross-sectional side view of another exemplary alternative end effector and another exemplary alternative shaft assembly that may be incorporated into the instrument of FIG. 2, with the end effector in an open position.

Clamp arm stop (906) is fixed along waveguide (902) such that clamp arm stop (960) is longitudinally aligned with opening (936). As shown in FIGS. 31A-31B, waveguide (902) may rotate about its own longitudinal axis. Rotation of waveguide (902) allows clamp arm stop (906) to be positioned adjacent to opening (936), as shown in FIGS. 30C and 31B, or away from lateral opening (936), as shown in FIGS. 30A and 31A. As will be described in greater detail below, moveable clamp arm stop (906) is configured to prevent clamp arm (944) from fully closing relative to blade (960) based on the angular position of waveguide (902).

FIG. 30A shows clamp arm (944) in an open position. When clamp arm (944) is in an open position, outer sheath (932) is in a distal position. Additionally, pin (945) is in a raised position within slot (943). When clamp arm stop (906) is in a position facing away from opening (936), as shown in FIGS. 30B and 31A, proximal translation of outer sheath (932) relative to inner tube (934) rotates clamp arm (944) about pin (945) unobstructed so that clamp arm (944) is in a completely closed position. In other words, stop (906) does not interfere with pivotal movement of clamp arm (944) when stop (906) is in the first position. Since pin (945) is free to vertically translate within slot (943), rotation of clamp arm (944) forces pin (945) in the downward direction to the bottom of slot (943). Clamp pad (980) is thus positioned adjacent to blade (960) without a gap between clamp pad (980) and blade (960). At this position, clamp arm (944) is configured to grasp tissue with a clamping pressure applied to tissue captured between clamp arm (944) and blade (960) such that end effector (940) is operable to cut and seal tissue in this position.

As mentioned above, waveguide (902) may rotate about the longitudinal axis of waveguide (902) between a first angular position (FIGS. 30A-30B) and a second angular position (FIG. 30C). With waveguide (902) in the first angular position, stop (906) faces away from opening (936). With waveguide (902) in the second angular position, stop (906) faces toward opening (936). As shown in FIGS. 30C and 31B, stop (906) is configured to limit the range of rotation of clamp arm (944) via contact between clamp arm stop (906) and nub (948) of clamp arm (944) when waveguide (902) is in the second angular position. Clamp arm stop (906) is positioned such that contact with nub (948) occurs when pin (945) is in between the top and bottom of slot (943). Because pin (945) is located between the top and bottom of slot (943), clamp pad (980) and blade (960) define gap distance (d).

Gap distance (d), similar to gap (G) described above, is configured to minimize a clamping pressure applied to tissue captured between clamp arm (944) and blade (960) such that blade (960) is operable to seal or weld the tissue, but not cut the tissue in this position. Therefore, depending on the location of clamp arm stop (906), closing of clamp arm (944) may grasp tissue such that blade (960) is operable to only seal tissue or cut and seal tissue. It should be understood that any suitable user input feature may be used to drive waveguide (902) between the first angular position and the second angular position. Various suitable features that may be used to drive waveguide (902) between the first angular position and the second angular position will be apparent to those of ordinary skill in the art in view of the teachings herein.

I. Exemplary Ultrasonic Surgical Instrument with Slidable Internal Tissue Gap Stop FIGS. 32A-34 depict another exemplary alternative shaft assembly (1030) and end effector (1040) that may be readily incorporated into instrument (100, 200) in place of shaft assembly (130, 230) and end effector (140, 240). End effector (1040) includes a pivotable clamp arm (1044) and an ultrasonic blade (1060). Ultrasonic blade (1060) is substantially similar to ultrasonic blade (160, 260) mentioned above. Similar to clamp arm (144, 244), clamp arm (1044) may include a clamp pad (1080) facing toward ultrasonic blade (1060). Additionally, clamp arm (1044) may be coupled with trigger (128) such that clamp arm (1044) is pivotable toward ultrasonic blade (1060) in response to pivoting of trigger (128) toward pistol grip (124); and such that clamp arm (1044) is pivotable away from ultrasonic blade (1060) in response to pivoting of trigger (128) away from pistol grip (124).

Figure 32A:
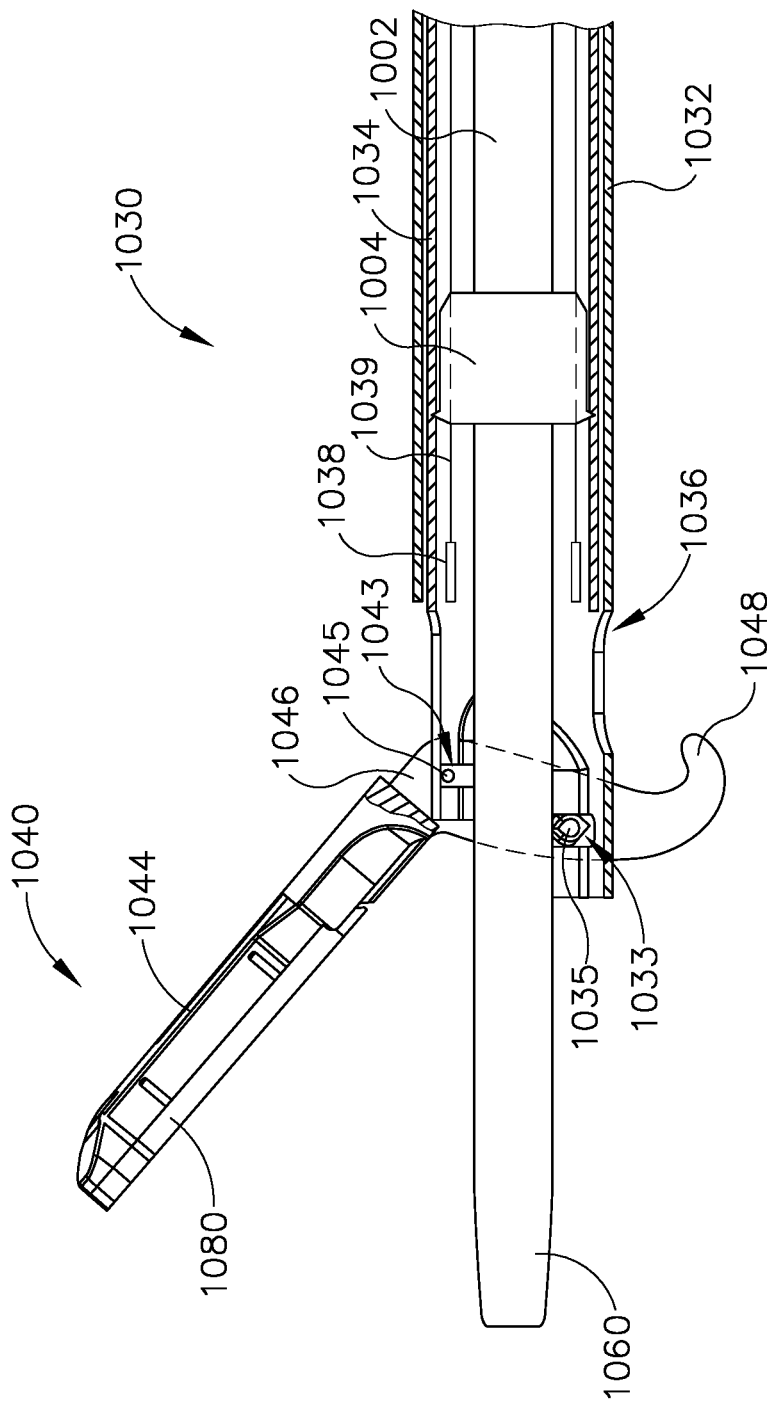
FIG. 32A depicts a cross-sectional side view of another exemplary alternative end effector and another exemplary alternative shaft assembly that may be incorporated into the surgical instrument of FIG. 2.
Figure 32B:
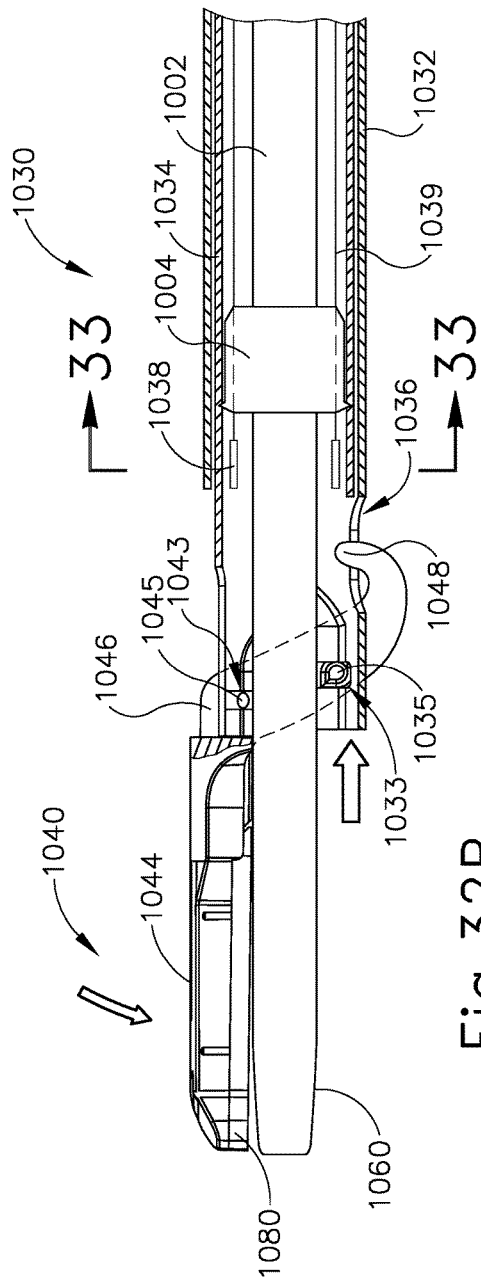
FIG. 32B depicts a cross-sectional side view of the end effector and shaft assembly of FIG. 32A, with the end effector in a first closed position.
Figure 32C:
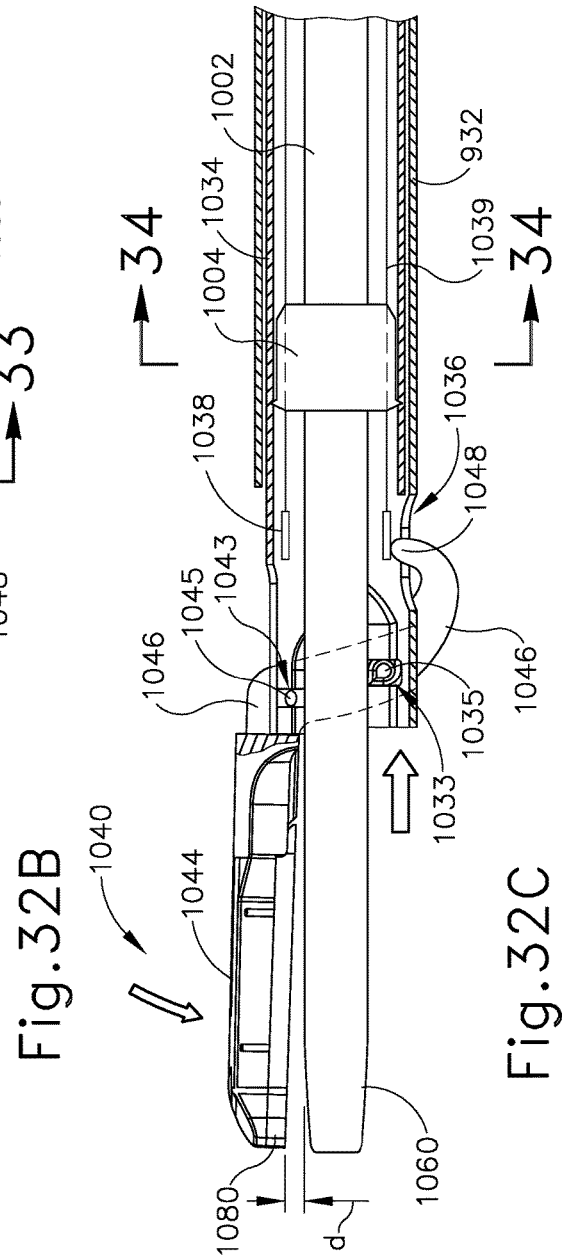
FIG. 32C depicts a cross-sectional side view of the end effector and shaft assembly of FIG. 32A, with the end effector in a second closed position.

As will be described in greater detail below, clamp arm (1044) is configured to pivot toward blade (1060) to a first closed position, defining a gap distance (d) as shown in FIG. 32C. Additionally, clamp arm (1044) is configured to pivot further toward blade (1060) to a second closed position as shown in FIG. 32B.

Shaft assembly (1030) includes an outer sheath (1032), an inner tube (1034) disposed within outer sheath (1032), a waveguide (1002) disposed within inner tube (1034), a seal (1004), and a moveable clamp arm stop (1038) connected to rods (1039) extending through seal (1004). Similar to shaft assembly (730, 830, 930), Outer sheath (1032) of the current example is slidable relative to inner tube (1034) of shaft assembly (1030). Outer sheath (1032) also includes a lateral opening (1036) that is sized to receive a nub (1048) of clamp arm (1044) when clamp arm (1044) rotates to a closed position.

The distal end of inner tube (1034) defines a slot (1043). A leg (1046) of clamp arm (1044) is pivotally coupled to slot (1043) of inner tube (1034) via pin (1045). Pin (1045) is free to vertically translate within slot (1043). A distal end of outer sheath (1032) defines a slot (1033). Slot (1033) of outer sheath (1032) is rotatably coupled with leg (1046) of clamp arm (1044) below ultrasonic blade (1060) via a pin (1035) such that longitudinal translation of outer sheath (1032) relative to inner tube (1034) causes rotation of clamp arm (1044) about pin (1045) toward and away from ultrasonic blade (1060) to thereby clamp tissue between clamp arm (1044) and ultrasonic blade (1060) to cut and/or seal the tissue. In particular, proximal longitudinal translation of outer sheath (1032) relative to inner tube (1034) and handle assembly (120) causes clamp arm (1044) to move toward ultrasonic blade (1060); and distal longitudinal translation of outer sheath (1032) relative to inner tube (1034) and handle assembly (120) causes clamp arm (1044) to move away from ultrasonic blade (1060).

Figure 34:
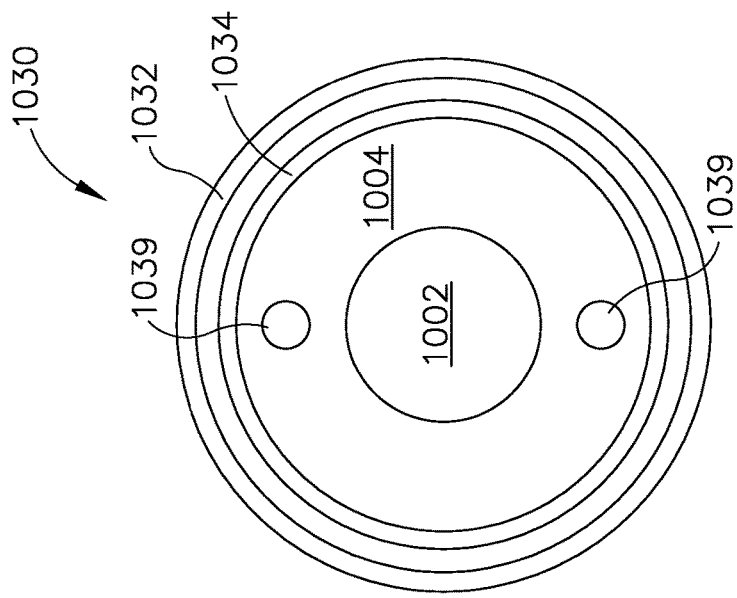
FIG. 34 depicts a cross-sectional front view of the shaft assembly of FIG. 32A taken along line 34-34 of FIG. 32C.
Figure 33:
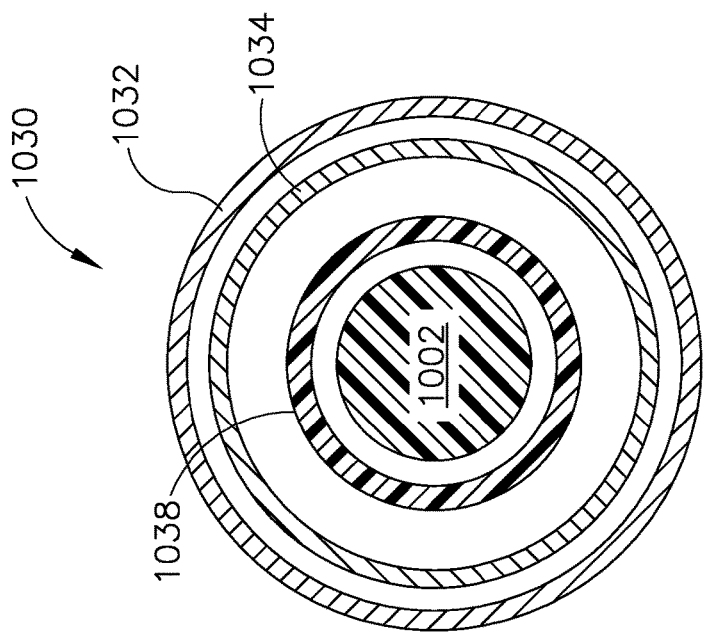
FIG. 33 depicts a cross-sectional front view of the shaft assembly of FIG. 32A taken along line 33-33 of FIG. 32B.

As best seen in FIG. 33, clamp arm stop (1038) is in the form of a rigid annular member that is coaxially disposed around waveguide (1002). As best seen in FIG. 34, rods (1039) extend through seal (1004). Additionally, rods (1039) are slidable relative to seal (1004). Therefore, clamp arm stop (1038) is slidable relative to outer sheath (1032), inner tube (1034), and waveguide (1002) via rods (1039). As seen in FIGS. 32A-32C, clamp arm stop (1038) may slide between a first longitudinal position (FIGS. 32A-32B) and a second longitudinal position (FIG. 32C). In the first longitudinal position, clamp arm stop (1038) is located proximally in relation to lateral opening (1036). In the second longitudinal position, clamp arm stop (1038) is located adjacent to lateral opening (1036). As will be described in greater detail below, clamp arm stop (1038) is configured to prevent clamp arm (1044) from fully closing relative to blade (1060) when clamp arm stop (1038) is in the second longitudinal position.

FIG. 32A shows clamp arm (1044) in an open position. When clamp arm (1044) is in an open position, outer sheath (1032) is in a distal position. Additionally, pin (1045) is in a raised position within slot (1043). When movable stop (1037) is in the first longitudinal position, as shown in FIG. 32B, proximal translation of outer sheath (1032) rotates clamp arm (1044) about pin (1045) unobstructed so that clamp arm (1044) is in a completely closed position. In other words, stop (1038) does not interfere with pivotal movement of clamp arm (1044) when stop (1038) is in the first position. Since pin (1045) is free to vertically translate within slot (1043), rotation of clamp arm (1044) forces pin (1045) in the downward direction to the bottom of slot (1043). Clamp pad (1080) is thus positioned adjacent to blade (1060) without a gap. At this position, clamp arm (1044) is configured to grasp tissue with a clamping pressure applied to tissue captured between clamp arm (1044) and blade (1060) such that end effector (1040) is operable to cut and seal tissue in this position.

As mentioned above, clamp arm stop (1038) may translate from a first longitudinal position, proximal to opening (1036), to a second longitudinal position, adjacent to opening (1036). As shown in FIG. 32C, clamp arm stop (1038) is configured to limit the range of rotation of clamp arm (1044) via contact between clamp arm stop (1038) and nub (1048) of clamp arm (1044) when stop (1038) is in the second longitudinal position. Clamp arm stop (1038) is positioned such that contact with nub (1048) occurs when pin (1045) is in between the top and bottom of slot (1043). Because pin (1045) in located between the top and bottom of slot (1043), clamp arm (1044) and blade (1060) define gap distance (d).

Gap distance (d), similar to gap (G) described above, is configured to minimize a clamping pressure applied to tissue captured between clamp arm (1044) and blade (1060) such that blade (1060) is operable to seal or weld the tissue, but not cut the tissue in this position. Therefore, depending on the location of moveable clamp arm stop (1038), closing of clamp arm (1044) may grasp tissue such that blade (1060) is operable to only seal tissue or cut and seal tissue. It should be understood that any suitable user input feature may be used to drive stop (1038) between the first longitudinal position and the second longitudinal position. Various suitable features that may be used to drive stop (1038) between the first longitudinal position and the second longitudinal position will be apparent to those of ordinary skill in the art in view of the teachings herein.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus for operating on tissue, the apparatus comprising: (a) a body; (b) a shaft assembly, wherein the shaft assembly extends distally from the body, wherein the shaft assembly comprises an acoustic waveguide, wherein the waveguide is configured to acoustically couple with an ultrasonic transducer; (c) an end effector, wherein the end effector comprises: (i) an ultrasonic blade in acoustic communication with the waveguide, and (ii) a clamp arm, wherein the clamp arm is configured to pivot toward and away from the ultrasonic blade, wherein the clamp arm is configured to pivot and stop at a first closed position associated with a first mode of operation, wherein the clamp arm is configured to pivot and stop at a second closed position associated with a second mode of operation.

Example 2

The apparatus of Example 1, wherein the clamp arm is configured to pivot toward and away from the ultrasonic blade about a first pivot point, wherein the clamp arm is configured to pivot from an open position to the first closed position, wherein the clamp arm is further configured to pivot about a second pivot point toward and away from the ultrasonic blade from the first closed position to the second closed position, wherein the second pivot point is proximal to the first pivot point, wherein the clamp arm is parallel to the ultrasonic blade at the first closed position.

Example 3

The apparatus of Example 2, wherein the clamp arm is parallel to the ultrasonic blade at the second closed position.

Example 4

The apparatus of any one or more of Examples 2 through 3, wherein the clamp arm is oriented at an oblique angle relative to the ultrasonic blade at the open position.

Example 5

The apparatus of any one or more of Examples 2 through 5, wherein the shaft assembly further comprises: (i) an outer sheath, and (ii) a first translatable member, wherein the first translatable member is configured to translate longitudinally relative to the outer sheath, wherein the clamp arm is configured to pivot toward and away from the ultrasonic blade along the angular path from the open position to the first closed position in response to longitudinal translation of the first translatable member relative to the outer sheath.

Example 6

The apparatus of Example 5, wherein the first translatable member comprises an inner tube, wherein the inner tube is slidably disposed within the outer sheath.

Example 7

The apparatus of any one or more of Examples 5 through 6, wherein the shaft assembly further comprises a pivot arm, wherein the pivot arm is pivotably coupled with the outer sheath at the second pivot point.

Example 8

The apparatus of Example 7, further comprising a second translatable member, wherein the second translatable member is configured to translate longitudinally relative to the outer sheath, wherein the pivot arm is configured to pivot relative to the outer sheath in response to translation of the second translatable member relative to the outer sheath.

Example 9

The apparatus of Example 8, wherein the second translatable member is disposed about the outer sheath.

Example 10

The apparatus of any one or more of Examples 8 through 9, wherein the second translatable comprises a pin, wherein the pivot arm comprises a slot, wherein the pin is disposed in the slot, wherein the pin and the slot are configured to cooperate to provide the pivotal movement of the pivot arm relative to the outer sheath in response to translation of the second translatable member relative to the outer sheath.

Example 11

The apparatus of any one or more of Examples 7 through 10, wherein the clamp arm comprises a first pivotal coupling and a second pivotal coupling, wherein the clamp arm is coupled with the first translatable member via the first pivotal coupling, wherein the clamp arm is coupled with the pivot arm via the second pivotal coupling.

Example 12

The apparatus of Example 11, wherein the first translatable member has a distal end defining an elongate slot, wherein the first pivotal coupling comprises a pin disposed in the elongate slot, wherein the elongate slot is configured to accommodate movement of the clamp arm toward and away from the ultrasonic blade between the second position and the third position.

Example 13

The apparatus of claim 2, further comprising a translating member, wherein the translating member is operable to translate between a first mode position and a second mode position, wherein the translating member is configured to prevent movement of the clamp arm from the first closed position to the second closed position when the translating member is in the first mode position, wherein the translating member is configured to permit movement of the clamp arm from the first closed position to the second closed position when the translating member is in the second mode position.

Example 14

The apparatus of any one or more of Examples 2 through 13, wherein the shaft assembly further comprises a stop, wherein the stop is configured to move from an inactive position to an active position, wherein the stop is configured to restrict the clamp arm from pivoting to the second closed position in the active position.

Example 15

The apparatus of Example 14, wherein the stop is configured to translate relative to the acoustic waveguide from the inactive position to the active position.

Example 16

The apparatus of any one or more of Examples 14 through 15, wherein the stop if fixed to the waveguide, wherein the waveguide is configured to rotate to move the stop from the inactive position to the active position.

Example 17

An apparatus for operating on tissue, the apparatus comprising: (a) a body; (b) a shaft assembly, wherein the shaft assembly extends distally from the body, wherein the shaft assembly defines a longitudinal axis, wherein the shaft assembly comprises: (i) an acoustic waveguide, wherein the waveguide is configured to acoustically couple with an ultrasonic transducer, (ii) a first translatable member, wherein the first translatable member is configured to translate relative to the body, and (iii) a second translatable member, wherein the second translatable member is configured to translate relative to the body; and (c) an end effector, wherein the end effector comprises: (i) an ultrasonic blade in acoustic communication with the waveguide, and (ii) a clamp arm, wherein the clamp arm is configured to pivot about a first pivot point toward and away from the ultrasonic blade along a first angular path from a first position to a second position in response to translation of the first translatable member relative to the body, wherein the clamp arm is further configured to pivot about a second pivot point toward and away from the ultrasonic blade along a second angular path from the second position to a third position in response to translation of the second translatable member relative to the body.

Example 18

The apparatus of Example 17, wherein the first translatable member comprises a first tube, wherein the second translatable member comprises a second tube, wherein the first and second tubes are coaxially aligned with each other about the longitudinal axis.

Example 19

A method of operating on tissue using an apparatus, wherein the apparatus comprises a shaft assembly and an end effector, wherein the shaft assembly defines a longitudinal axis, wherein the end effector comprises a clamp arm and an ultrasonic blade, the method comprising: (a) positioning the ultrasonic blade near tissue; (b) pivoting the clamp arm about a first pivot point toward the ultrasonic blade to thereby compress the tissue between the clamp arm and the ultrasonic blade, wherein the act of pivoting the clamp arm comprises driving the clamp arm along a first angular path from a first position to a second position; (c) pivoting the clamp arm about a second pivot point toward the ultrasonic blade to thereby further compress the tissue between the clamp arm and the ultrasonic blade, wherein the act of translating the clamp arm comprises driving the clamp arm along a second angular path from the second position to a third position; and (d) activating the ultrasonic blade to vibrate at an ultrasonic frequency, thereby cutting the tissue with the ultrasonic blade.

Example 20

The method of Example 19, wherein the apparatus further comprises a trigger and a grip, wherein the act of pivoting the clamp arm about the first pivot point toward the ultrasonic blade comprises moving the trigger through a first range of motion toward the grip, wherein the act of pivoting the clamp arm about the second pivot point toward the ultrasonic blade comprises moving the trigger through a second range of motion toward the grip.

V. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for operating on tissue, the apparatus comprising:
   (a) a shaft assembly, wherein the shaft assembly comprises:
      (i) an acoustic waveguide, wherein the waveguide is configured to acoustically couple with an ultrasonic transducer,
      (ii) a stationary member, and
      (iii) a first translatable member configured to translate relative to the stationary member; and
   (b) an end effector, wherein the end effector comprises:
      (i) an ultrasonic blade in acoustic communication with the waveguide,
      (ii) a clamp arm, wherein the clamp arm is configured to pivot toward and away from the ultrasonic blade about a first pivot point and a second pivot point, wherein the second pivot point is proximal to the first pivot point, and
      (iii) a pivot arm pivotably coupled with the clamp arm via the first pivot point, wherein the pivot arm is pivotably coupled with the stationary member via the second pivot point,
      wherein the clamp arm is configured to pivot between an open position and a first closed position in response to translation of the first translatable member, wherein the pivot arm is configured to remain in a first angular position when the clamp arm pivots between the open position and the first closed position, wherein the first closed position is associated with a first mode of operation,
      wherein the clamp arm and the pivot arm are configured to pivot about the second pivot point between the first closed position and a second closed position, wherein the second closed position is associated with a second mode of operation.

2. The apparatus of claim 1, wherein the clamp arm is parallel to the ultrasonic blade at the first closed position.

3. The apparatus of claim 2, wherein the clamp arm is parallel to the ultrasonic blade at the second closed position.

4. The apparatus of claim 2, wherein the clamp arm is oriented at an oblique angle relative to the ultrasonic blade at the open position.

5. The apparatus of claim 2, wherein the stationary member further comprises an outer sheath, wherein the clamp arm is configured to pivot toward and away from the ultrasonic blade along an angular path from the open position to the first closed position in response to longitudinal translation of the first translatable member relative to the outer sheath.

6. The apparatus of claim 5, wherein the first translatable member comprises an inner tube, wherein the inner tube is slidably disposed within the outer sheath.

7. The apparatus of claim 5, wherein the shaft assembly further comprises a pivot arm, wherein the pivot arm is pivotably coupled with the outer sheath at the second pivot point.

8. The apparatus of claim 7, further comprising a second translatable member, wherein the second translatable member is configured to translate longitudinally relative to the outer sheath, wherein the pivot arm is configured to pivot relative to the outer sheath in response to translation of the second translatable member relative to the outer sheath.

9. The apparatus of claim 8, wherein the second translatable member is disposed about the outer sheath.

10. The apparatus of claim 8, wherein the second translatable member comprises a pin, wherein the pivot arm comprises a slot, wherein the pin is disposed in the slot, wherein the pin and the slot are configured to cooperate to provide the pivotal movement of the pivot arm relative to the outer sheath in response to translation of the second translatable member relative to the outer sheath.

11. The apparatus of claim 7, wherein the clamp arm comprises a first pivotal coupling and a second pivotal coupling, wherein the clamp arm is coupled with the first translatable member via the first pivotal coupling, wherein the clamp arm is coupled with the pivot arm via the second pivotal coupling.

12. The apparatus of claim 11, wherein the first translatable member has a distal end defining an elongate slot, wherein the first pivotal coupling comprises a pin disposed in the elongate slot, wherein the elongate slot is configured to accommodate movement of the clamp arm toward and away from the ultrasonic blade between the first closed position and the second closed position.

13. The apparatus of claim 2, further comprising a translating member, wherein the translating member is operable to translate between a first mode position and a second mode position, wherein the translating member is configured to prevent movement of the clamp arm from the first closed position to the second closed position when the translating member is in the first mode position, wherein the translating member is configured to permit movement of the clamp arm from the first closed position to the second closed position when the translating member is in the second mode position.

14. The apparatus of claim 1, wherein the shaft assembly further comprises a stop, wherein the stop is configured to move from an inactive position to an active position, wherein the stop is configured to restrict the clamp arm from pivoting to the second closed position in the active position.

15. The apparatus of claim 14, wherein the stop is configured to translate relative to the acoustic waveguide from the inactive position to the active position.

16. The apparatus of claim 14, wherein the stop if fixed to the waveguide, wherein the waveguide is configured to rotate to move the stop from the inactive position to the active position.

17. An apparatus for operating on tissue, the apparatus comprising:

(a) a shaft assembly, wherein the shaft assembly defines a longitudinal axis, wherein the shaft assembly comprises:
  (i) an acoustic waveguide, wherein the waveguide is configured to acoustically couple with an ultrasonic transducer,
  (ii) a first translatable member comprising a first tube, wherein the first translatable member is configured to translate relative to the acoustic waveguide, and
  (iii) a second translatable member comprising a second tube, wherein the first tube and the second tube are coaxially aligned with each other about the longitudinal axis, wherein the second translatable member is configured to translate relative to the acoustic waveguide; and
(b) an end effector, wherein the end effector comprises:
  (i) an ultrasonic blade in acoustic communication with the waveguide, and
  (ii) a clamp arm, wherein the clamp arm is configured to pivot about a first pivot point toward and away from the ultrasonic blade along a first angular path from a first position to a second position in response to translation of the first translatable member relative to the acoustic waveguide, wherein the clamp arm is further configured to pivot about a second pivot point toward and away from the ultrasonic blade along a second angular path from the second position to a third position in response to translation of the second translatable member relative to the body.

18. An apparatus for operating on tissue, the apparatus comprising:
(a) a body;
(b) a shaft assembly, wherein the shaft assembly extends distally from the body, wherein the shaft assembly defines a longitudinal axis, wherein the shaft assembly comprises:
  (i) an acoustic waveguide, wherein the waveguide is configured to acoustically couple with an ultrasonic transducer,
  (ii) a static member comprising first tube,
  (iii) a first translatable member comprising a second tube coaxially disposed with respect to the first tube, wherein the first translatable member is configured to translate relative to the body between a first position and a second position, and
  (iv) a second translatable member configured to translate with the first translatable member between the first position and the second position, wherein the second translatable member is configured to translate relative to the body and the first translatable member between the second position and a third position; and
(c) an end effector, wherein the end effector comprises:
  (i) an ultrasonic blade in acoustic communication with the waveguide, and
  (ii) a clamp arm, wherein the clamp arm is configured to pivot relative to the ultrasonic blade between an open position, a first closed position, and a second closed position, wherein the first translatable member is configured to drive the clamp arm between the open position and the first closed position while translating from the first position to the second position, wherein the second translatable member is configured to drive the clamp arm between the first closed position and the second closed position while translating from the second position to the third position.

19. The apparatus of claim 18, wherein the first tube comprises an outer tube, wherein the second tube comprises an inner tube coaxially disposed within the outer tube.

20. The apparatus of claim 19, wherein the second translating member comprises a pivot tube disposed about the outer tube.

* * * * *